US007169972B2

(12) United States Patent
Stepanova et al.

(10) Patent No.: US 7,169,972 B2
(45) Date of Patent: Jan. 30, 2007

(54) METHODS AND COMPOSITIONS TO MODULATE ETHYLENE SENSITIVITY

(75) Inventors: Anna N. Stepanova, Cary, NC (US); Joseph R. Ecker, Carlsbad, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 541 days.

(21) Appl. No.: 10/142,638

(22) Filed: May 8, 2002

(65) Prior Publication Data

US 2006/0294621 A1    Dec. 28, 2006

Related U.S. Application Data

(60) Provisional application No. 60/289,835, filed on May 9, 2001, provisional application No. 60/289,364, filed on May 8, 2001.

(51) Int. Cl.
*C12N 15/01* (2006.01)
*C12N 15/82* (2006.01)
*A01H 5/00* (2006.01)

(52) U.S. Cl. .................. 800/306; 800/270; 800/298

(58) Field of Classification Search ............ 800/270, 800/278, 293, 294, 298, 306; 536/23.1, 23.6
See application file for complete search history.

(56) References Cited

OTHER PUBLICATIONS

Alonso J.M. et al. Science, Aug. 1, 2003; vol. 301, pp. 653-657.*
Chen Y. et al. Annals of Botany, 2005; vol. 95, pp. 901-915.*
Adams-Phillips L. et al. Plant Molecular Biology; 2004, vol. 54, pp. 387-404.*
Johnson, P.R. and Ecker, J.R. (1998). The ethylene gas signal transduction pathway: a molecular perspective, Annu Rev Genet 32, 227-54.
Morgan PW, D.M. (1997). Ethylene and plant responses to strees, Physiologia Plantarum 100, 620-630.
Lui et al. (1998). Two transcription factors, DREB1 and DREB2, with an EREBP/AP2 DNA binding domain separate two cellular signal transduction pathways in drought-and low-temperature-responsive gene expression, respectively, in Arabidopsis, Plant Cell 10, 1391-406.
Nakashima et al., (2000). Organization and expression of two Arabidopsis DREB2 genes encoding DRE- binding proteins involved in dehydration- and high-salinity-responsive gene expression, Plant Mol Biol 42, 657-65.
Menke et al. (1998). A novel jasmonate- and elicitor-responsive element in the periwinkle secondary metabolite biosynthetic gene Str interacts with a jasmonnate- and elicitor-inducible AP2-domain transcription factor, ORCA2, Embo J. 18, 4455-4463.
Kagaya et al. (1999). RAV1, a novel DNA-binding protein, binds to bipartite recognition sequence through two distinct DNA-binding domains uniquely found in higher plants, Nucleic Acids Res 27, 470-8.
Okamuro et al. (1997) The AP2 domain of APETALA2 defines a large new family of DNA binding proteins in Arabidopsis, Procl Natl Acad Sci USA 94, 7076-7081.
Kieber et al. (1993). CTR1, a negative regulator of the ethylene response pathway in Arabidopsis, encodes a member of the raf family of protein kinases, Cell 72, 427-441.
Stepanova et al. (2000). Ethylene Signaling: from mutants to molecules, Curr Opin Plant Biol 3, 353-360.
Roman et al. (1995). Genetic analysis of ethylene signal transduction in *Arabidopsis thaliana:* five novel mutant loci integrated into a stress response pathway, Genetics 139, 1393-1409.

* cited by examiner

*Primary Examiner*—Russell P. Kallis
(74) *Attorney, Agent, or Firm*—Morrison & Foerster LLP

(57) ABSTRACT

The field of the invention relates to plants and plant genes, including both plant mutants and transgenic plants containing a gene that confers an ethylene insensitive phenotype. Also encompassed by the invention are methods of using the disclosed plant gene to confer an ethylene insensitive phenotype.

12 Claims, 3 Drawing Sheets

| Background | Root length (mm) 0μM ACC | Root length (mm) 10μM ACC | Fold inhibition | Hypocotyl length (mm) 0μM ACC | Hypocotyl length (mm) 10μM ACC | Fold inhibition |
|---|---|---|---|---|---|---|
| Col | 6.51±0.85 | 1.88±0.27 | 3.46 | 9.36±1.13 | 4.72±0.38 | 1.98 |
| Ler | 5.14±1.23 | 2.14±0.50 | 2.40 | 7.86±1.25 | 3.56±0.80 | 2.21 |
| eil1-1 | 5.42±0.85 | 2.55±0.38 | 2.13 | 9.20±0.91 | 5.52±0.49 | 1.67 |
| eil1-2 | 5.78±1.38 | 3.09±0.63 | 1.87 | 8.07±1.44 | 4.99±1.07 | 1.62 |
| ein3-1 | 6.14±1.02 | 4.54±0.98 | 1.35 | 8.72±1.28 | 7.23±0.83 | 1.21 |
| ein2-5 | 6.20±0.88 | 5.83±0.98 | 1.06 | 9.44±1.33 | 8.99±1.67 | 1.05 |
| eil1-1 ein3-1 | 5.79±1.19 | 5.15±0.88 | 1.12 | 8.36±1.40 | 8.23±1.20 | 1.02 |
| eil1-2 ein3-1 | 6.58±1.90 | 6.61±1.59 | 1.00 | 9.24±1.60 | 8.89±1.53 | 1.04 |

B

METHODS AND COMPOSITIONS TO MODULATE ETHYLENE SENSITIVITY

RELATED APPLICATIONS

This application claims priority from both U.S. provisional patent application No. 60/289,364, filed May 8, 2001, and U.S. provisional patent application No. 60/289,835, filed May 9, 2001.

GOVERNMENTAL INTEREST

This invention was made with United States Government support under grant number MCB0049003 awarded by the National Science Foundation and grant number DE-F603-00ER15113 awarded by the Department of Energy. The government may have certain rights in this invention.

BACKGROUND OF THE INVENTION

1. Field of the Invention

The field of the invention relates to plants and plant genes, including both plant mutants and transgenic plants containing a gene that confers an ethylene insensitive phenotype. Also encompassed by the invention are methods of using the disclosed plant gene to confer an ethylene insensitive phenotype.

2. Description of the Related Art

Ethylene is an endogenous plant hormone that affects many aspects of growth and development, such as germination, flower and leaf senescence, fruit ripening, leaf abscission, cell fate determination in root epidermis, root nodulation, sex determination, programmed cell death, and responsiveness to stress and pathogen attack (Abeles et al., 1992; Johnson and Ecker, 1998). The biosynthetic pathway for this hormone is now well-established. First, the amino acid methionine is converted into ethylene via S-adenosyl-methionine ("SAM" or "AdoMet") and 1-aminocyclopropane-1-carboxylic acid (ACC) (Yang and Hoffman, 1984). The key enzymes of ethylene biosynthesis, AdoMet synthase, ACC synthase and ACC oxidase, have now been cloned and characterized (Johnson and Ecker, 1998; Morgan P W, 1997).

Ethylene is involved in regulating many physiological processes. Examples, include responses to pathogens, initiation of fruit ripening, cell wall formation/degradation, leaf epinasty (downward curvature of leaf), inhibition of seedling elongation or seed germination, and the promotion (or inhibition, in some species) of flowering. Ethylene also regulates the abscission of plant organs such as leaves, fruits, and flowers (see, e.g., Taiz and Zeiger, 1991, Plant Physiology, Benjamin/Cummings Publishing Company, Inc., p. 474–482). Therefore, plants having a decreased sensitivity to ethylene may have several agricultural uses. For example, plants having a decreased sensitivity to ethylene may have better storage characteristics. Fruits of such plants may ripen more slowly. This could be an advantage for post-harvest handling of agricultural products, such as processing, packaging, and storage of fruit. There may be less of a loss of fruit crops due to such traditionally damaging problems as rotting, over-ripening, and degradation. It may be possible to better control the ripening rate and ripening characteristics of plants carrying these modified EDF genes. It is possible, as well, to link the modified genes to specific promoters in order to better modulate the expression of the genes so that the response to ethylene is turned off at certain times or in certain tissues, while acting normally in other parts of the plant or at other times in development.

Plants respond to ethylene through a family of integral membrane receptors. In *Arabidopsis*, at least five family members are involved, including: ETHYLENE RECEPTOR1 (ETR1), ETR2, ETHYLENE INSENSITIVE4 (EIN4), ETHYLENE RESPONSE SENSOR1 (ERS1), and ERS2 (Chang et al., 1993; Hua et al., 1995; Hua et al., 1998; Sakai et al., 1998). Ethylene binds to the receptors via a copper cofactor (Rodriguez et al., 1999) and genetic studies suggest that hormone binding inactivates the receptors (Hua and Meyerowitz, 1998). In the absence of ethylene, the receptor are predicted to be functionally active histidine kinases which activate a Raf-like S/T kinase, CONSTITUTIVE TRIPLE RESPONSE1 (CTR1), also a negative regulator of the pathway (Kieber et al., 1993). Genetic studies also predict that EIN2, EIN3, EIN5, and EIN6 (Roman et al., 1995) are positive regulators of the ethylene response.

EIN2 is a metal ion transporter-related integral-membrane protein, whose function is not well-understood (Alonso et al., 1999). The nuclear protein EIN3 and its paralogs, the EIN3-LIKE proteins (EILs), are transcription factors that bind to the promoters of ethylene-response genes such as ETHYLENE RESPONSE FACTOR 1 (ERF1) and initiate a transcriptional cascade leading to the regulation of ethylene target genes (Chao et al., 1997; Solano et al., 1998).

Ethylene and Disease Resistance

Ethylene gas is released upon pathogen infection and is thought to be a part of the plant defense mechanism against the spread of the pathogen. In the past year, several studies have demonstrated that a functional ethylene signaling pathway is required for resistance against some, but not all, pathogens. EIN2 was shown to be essential for pathogen-mediated systemic induction of the basic chitinase PR-3 and a hevein-like gene PR-4 in *Arabidopsis* upon infection with the fungus *Alternaria brassicicola* (Thomma et al., 1999). Local induction of the HEL, CHIB and PDF1.2 genes by a culture filtrate from the virulent Gram-negative bacterium *Erwinia carotovora* subsp. *carotovora* was also severely reduced in the ein2-1 and etr1-1 mutants (Norman-Setterblad et al., 2000). Furthermore, ein2-1 plants exhibited greater susceptibility to infections by *E. carotovora* subsp. *carotovora* (Norman-Setterblad et al., 2000) and the fungus *Botrytis cinerea*, but not to infection by avirulent strains of the fungi *A. brassicicola* and *Peronospora parasitica* (Thomma et al., 1999).

Ethylene Response in Animals

The possession of an ethylene signal transduction pathway is not unique to *Arabidopsis*. Orthologs of all the major signaling components known to be involved in this *Arabidopsis* pathway have been identified in several other plant species (Chang and Shockey, 1999; Johnson and Ecker, 1998) (Ecker, unpublished). Moreover, a bacterial protein that has both sequence homology to the transmembrane domain of ETR1 and ethylene binding properties has been isolated from *Synechocystis* sp. (Rodriguez et al., 1999). Recently, an animal species, Suberites domuncula, has been shown for the first time to respond to ethylene, both physiologically and at the molecular level (Krasko et al., 1999). In this sponge, ethylene can repress starvation-induced apoptotic cell death, and the mRNA levels of at least two genes, SDERR and CaM kinase II, are up-regulated as a result of ethylene exposure (Krasko et al., 1999). Although it is not yet clear whether this animal can sense and respond to ethylene gas via a conventional 'plant-specific' pathway, the fact that gene expression is affected suggests the existence of some sort of perception and transduction pathway for this gas signal.

Thus, what is needed in the art are plants with altered ethylene sensitivity in order to provide more of the effects listed above.

SUMMARY OF THE INVENTION

The invention relates to the plant EDF gene family, and the proteins encoded by them. Embodiments of the invention include mutant plants having one or more mutated forms of the edf genes, which have an altered response to ethylene. The plant's altered ethylene response may be ethylene insensitivity, or an ethylene insensitive root. The altered plant may utilize several altered edf genes, such edf1, edf2, edf3 or edf4, either alone, in combination with each other, or even in combination with other altered gene mutations such as ctr1. In some embodiments, the plant may be *Arabidopsis thaliana*, however, the plant is preferably a crop plant for consumption by humans or animals.

In other embodiments, the invention includes a plant expression vector having one or more of the following polynucleotides: edf1, edf2, edf3, edf4, singly or in combination with each other or with the mutant ctr1 gene. The genes may be linked to a promoter, which may be constitutive, tissue specific, or inducible.

Other embodiments of the invention include a method for producing a transgenic plant with an altered ethylene-dependent phenotype by transforming a plant cell with a plant expression vector comprising the isolated polynucleotide of the above-mentioned vector, followed by regeneration of the transformed plant, and selection for the altered phenotype. Such an altered phenotype may include, for example, ripening, flowering, senescence, browning, and sensitivity to pathogens.

In other embodiments, a desirable altered ethylene-dependent phenotype may be produced by overexpressing EDF1, EDF 2, EDF3, EDF4 genes. Further, these genes may be introduced in a plant in either a sense orientation to inhibit the corresponding expression of the gene. The genes may be oriented in an antisense fashion, such as to produce complementary RNA to the endogenous gene in order to inhibit expression of the gene.

Other embodiments include genetically modified plants plant having exogenous sequences encoding one or more edf genes or sequences of at least 80% homology to edf1, edf2, edf3, or edf4 genes. These genes may be linked to a regulatory nucleic acid sequence. The regulatory sequence may be a promoter, such as a constitutive, inducible, or tissue-specific promoter. The exogenous sequence may include a gene encoding a selectable marker. The plant produced by these methods may be a dicot or a monocot, or a plant seed having at least one exogenous nucleic acid sequence encoding an edf gene.

BRIEF DESCRIPTION OF THE DRAWINGS

FIG. 1 is an EDF/EDL protein alignment. Amino acid sequence comparisons of EDF1, EDF2, EDF3, EDF4, EDL1, and EDL2 are shown. Identical and similar amino acids are indicated by black and gray boxes, respectively. The AP2- and B3-domains are highlighted by the double-sided arrows above the sequences.

FIG. 2A shows T-DNA insertion for EDF1; FIG. 2B shows T-DNA insertion for EDF2; FIG. 2C shows T-DNA insertion for EDF3; and FIG. 2D shows T-DNA insertion for EDF4.

DETAILED DESCRIPTION OF THE PREFERRED EMBODIMENT

Figure 1:
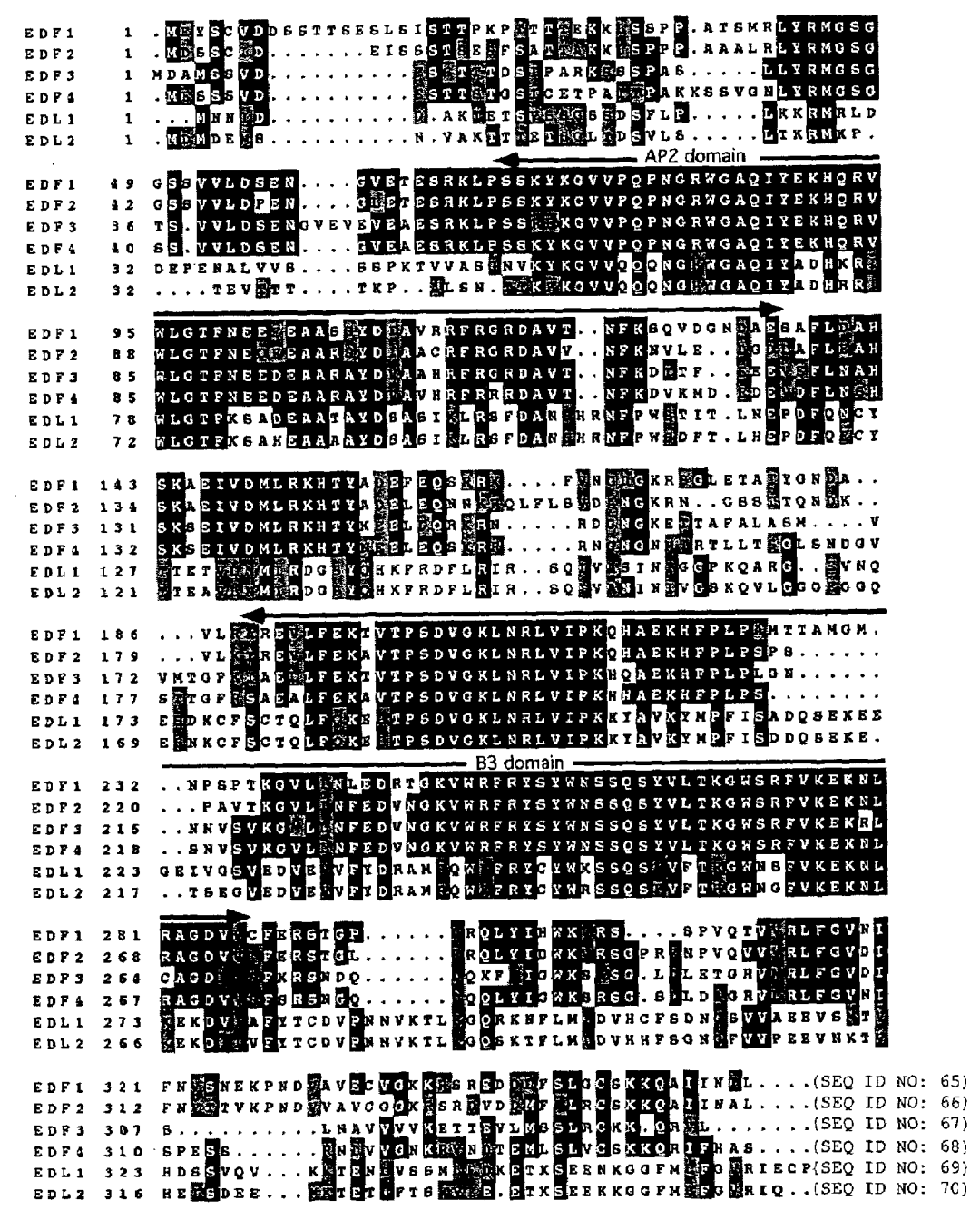
Figure 2:
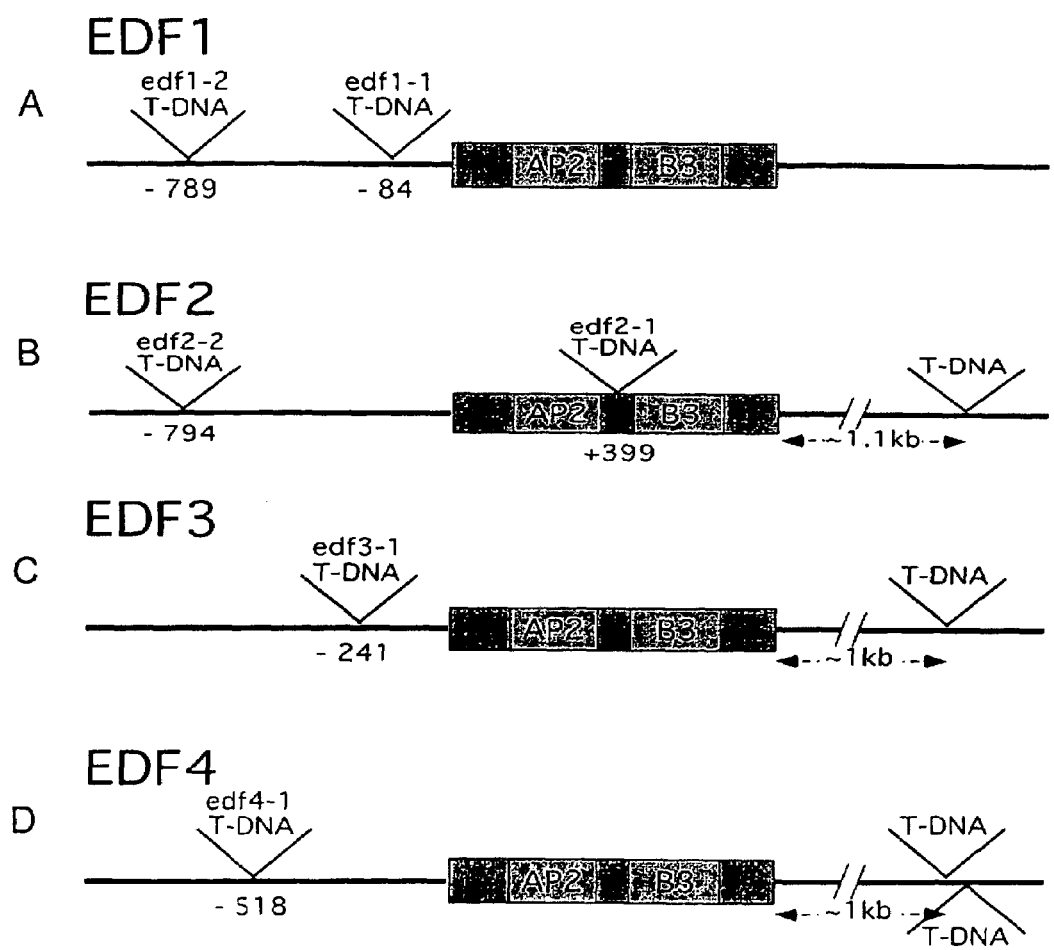
FIGS. 2A–D are a T-DNA insertion diagram. (A) Schematic representation of the four EDF family members with the respective positions of the T-DNA insertions. AP2 and B3 domains are highlighted. The coordinates of the T-DNA insertion sites are indicated with respect to the translation start site.

Genetically Modified Plants Having Modified Levels of EDF Expression and Altered Sensitivity to Ethylene The plant hormone ethylene participates in many developmental processes, yet the molecular mechanisms of its action are only beginning to be uncovered. In order to elucidate the signal transduction events that lead to changes in expression of ethylene-responsive genes, several AP2-domain-containing transcription factors were cloned and characterized. Of particular interest was a small family of novel transcription factors, termed herein as "ETHYLENE-RESPONSE DNA-BINDING FACTORS" (EDFs), that were found to be involved in transcriptional regulation of ethylene-inducible genes and pathways. A protein alignment of four EDF family members, along with related proteins EDL1 and EDL2, is shown in FIG. 1. All four members of the EDF family were found to affect ethylene-inducible expression. As shown herein, mutant plants or transformed plants having inactivated or partially inactivated EDF genes (i.e., edf1, edf2, edf3, or edf4) may have a decreased sensitivity to ethylene. Accordingly, embodiments of the present invention include the genetic modification of EDF proteins and the genes that encode them to alter plant sensitivity and responsiveness to ethylene.

Several lines of evidence disclosed herein clearly indicate that the EDF group of transcription factors may act to upregulate or downregulate many ethylene responsive genes. In fact, entire sets of ethylene-related pathways may be regulated by this family of transcription factors. Indeed, a knowledge of this protein family and its interactions with other ethylene pathway gene products is useful to assist in the designing and creation of plants with new and desirable attributes. Thus, embodiments of the invention include transgenic plants or otherwise modified plants having altered levels of EDF protein family members. For example, one embodiment of the invention is plants with decreased ethylene sensitivity made by transformation or mutagenesis methods to create plants with decreased or inactive forms of EDF proteins. Methods including, but not limited to, antisense technology, sense suppression technology, mutagenesis methods, or other methods, using the information relating to the function of the gene product as described herein, could be used to make such plants.

Plants having reduced EDF activity and thus a reduced sensitivity to ethylene could be useful for the floral industry.

Since ethylene may be involved in floral senescence, these modified plants may have a longer flower longevity. Further, EDF genes could be used to create vegetative crops that do not bolt or flower easily. For example, lettuce, spinach, other leafy vegetables, or certain herbs may have higher yields due to decreased floral initiation. Because ethylene has been implicated in senescence, potted plants made according to the methods described herein may last longer than control plants due to reduced leaf senescence.

One of skill in the art would appreciate that different plants or different agricultural crops may benefit from different types of promoter/EDF gene modifications. For example, in some plants it may be desirable to decrease ethylene sensitivity constitutively using, for example, a CaMV35S promoter linked to the modified EDF gene. Other plants may benefit from decreasing ethylene sensitivity only at fruit ripening, for example, by linking a modified EDF gene to a fruit ripening-specific promoter. It may be useful to create plants that have modified ethylene sensitivity only in the vegetative parts of the plant. In another example, it may be useful to prepare plants having the modified EDF gene so that the ethylene sensitivity is decreased only at high temperatures. Such a scenario may be important in post-harvest storage and transportation of fruit, for example. It may be useful to link an EDF gene to a promoter such that the ethylene insensitivity characteristic is brought about only when the plant is stored in the darkness by operably linking a darkness-inducible promoter to the modified EDF gene. This may be particularly useful for managing long term storage of certain crops between the time of harvest and the time of display for sale. Once the agricultural product is unpacked for market display in the light, for example, the EDF gene would be downregulated, the ethylene insensitivity would decrease, and ripening would resume. Many other options for modifying specific crops as desired can be designed by one of skill in the art.

Alternatively, it may be of interest to produce plants that overexpress one or more members of the EDF gene family. This may cause plants to have increased sensitivity to ethylene, or it may create other desirable plant phenotypes which may be of agronomic importance. The EDF overexpression may be either constitutive, inducible, or tissue-specific.

Further, since ethylene pathways involve the action of many gene products, as detailed herein, it may be useful to engineer plants having modified EDF genes in combination with other modified genes in the ethylene synthesis or response pathway. The other ethylene pathway genes may be inactivated or partially inactivated, for example, by insertional mutation, or point mutation, by antisense technology, or by molecular decoy technology. Alternatively, the other ethylene pathway genes may be conditionally overexpressed or may be preferentially expressed (such as in certain tissues, or in response to certain developmental or environmental cues).

As described herein, ethylene signaling processes may interact with the signaling processes of other hormones, such as auxin. Therefore, mutant or transgenic plants having altered expression of EDF genes may exhibit useful alterations in auxin-related pathways. Further, since ethylene is released upon certain types of pathogen infection, mutant or transformed plants having an altered ethylene sensitivity may be useful to modify responses to pathogens. In fact, since many genes have altered expression characteristics in response to ethylene application, mutant or transgenic plants carrying altered EDF genes to alter ethylene sensitivity may be useful in altering a myriad of physiological roles and morphological phenotypes in plants.

The EDF proteins were found to possess two DNA-binding domains, AP2 and B3-like, that in vitro recognize a bipartite DNA element, RBS. To address the in planta function of EDFs, gain- and loss-of-function strategies were employed. Overexpression studies revealed that a truncated version of EDF1 can trigger constitutive activation and repression of different branches of the ethylene signaling pathway. Knockout mutant analysis suggested that the functions of the EDF genes are largely redundant. Weak ethylene insensitivity of the quadruple edf1 edf2 edf3 edf4 mutant implied the requirement of the EDF gene products for the normal responsiveness to ethylene gas. Addition of the ctr1 mutation to the quadruple edf knockout revealed the ability of the quadruple knockout to partially suppress constitutive ethylene signaling initiated by ctr1.

Microarray technology has been utilized to examine molecular changes induced in plants after exogenous application of ethylene. Gene expression analysis revealed that many aspects of plant growth and metabolism were affected by ethylene gas. Mutations in the edf genes and EDF1/EDF2 overexpression resulted in abnormal expression of a subclass of ethylene-regulated genes. Several genes that possess an RBS in their promoters and show altered expression levels in the mutants represent potential in vivo targets of the EDF proteins. Therefore, modifications of EDF proteins as described herein may affect the expression of many of these ethylene-regulated genes and pathways, which may lead to potentially useful plant phenotypes.

Additionally, two other complementary approaches, transposon mutagenesis and the yeast two-hybrid system, have been employed to identify novel components of the ethylene signaling pathway. Genetic and phenotypic analysis of the resulting mutants and preliminary characterization of EIL1- and EIL2-interacting clones are presented.

Genetic and Molecular Characterization of Ethylene-Regulated Genes: the ETHYLENE RESPONSE DNA-BINDING FACTOR Family Embodiments of the invention relate to recombinant plants engineered to possess various degrees of ethylene insensitivity. In one embodiment, recombinant plants containing mutations in one or more of the EDF1 (SEQ ID NO: 59), EDF2 (SEQ ID NO: 60), EDF3 (SEQ ID NO: 61), or EDF4 (SEQ ID NO: 62) nucleotide sequences possess such ethylene insensitivity. In another embodiment, the ctr1 gene is mutated, either alone or in combination with one or more edf gene mutations to enhance ethylene insensitivity. In another embodiment, gain-of-function recombinant plants are contemplated.

The disclosure below relates, in part, to the identification, isolation, cloning and sequencing of the EDF genes. Thus, in one series of embodiments, the present invention provides isolated nucleic acids including nucleotide sequences comprising or derived from the disclosed edf genes and/or encoding polypeptides comprising or derived from the EDF proteins. The EDF sequences disclosed include the specifically disclosed sequences, and splice variants, allelic variants, synonymous sequences, and homologous or orthologous variants thereof. Thus, for example, the invention provides genomic and cDNA sequences from the EDF1, EDF2, EDF3, EDF4 genes. The disclosure also provides allelic variants and homologous or orthologous sequences. For example, for use in allele specific hybridization screening or PCR amplification techniques, subsets of the edf sequences, including both sense and antisense sequences, and both normal and mutant sequences, as well as intronic, exonic and untranslated sequences, may be employed. Such sequences may comprise a small number of consecutive nucleotides from the sequences which are disclosed or otherwise enabled herein but preferably include at least 8–10, and more preferably 9–25, consecutive nucleotides from an edf sequence or sequences. Various nucleic acid constructs in which edf sequences, either complete or subsets, are operably joined to exogenous sequences to form cloning vectors, expression vectors, fusion vectors, transgenic constructs, and the like, are also disclosed.

Nucleotide Sequences Relating to edf Genes

The nucleotide sequences for EDF1, EDF2, EDF3, EDF4 genes and the proteins encoded thereby, have been identified and been shown to be useful in modulating ethylene resistance in plants. As is discussed more fully below, the edf genes were cloned, sequenced and expressed. Polynucleotide molecules encoding the EDF proteins are provided below.

Polynucleotide molecules encoding EDF proteins include those sequences resulting in minor genetic polymorphisms, differences between strains, and those that contain amino acid substitutions, additions, and/or deletions.

In some instances, one can employ such changes in the sequence of a recombinant EDF protein to substantially decrease or increase the biological activity of a particular edf-encoded protein relative to the activity of the corresponding wild-type edf-encoded protein. Such changes can also be directed towards endogenous edf nucleotide sequences using, for example, various molecular biological techniques to alter the endogenous gene and therefore its protein product.

Nucleotide sequences encoding EDF proteins can be used to identify polynucleotide molecules encoding other proteins with biological functions similar to that of the identified edf genes. Complementary DNA molecules encoding EDF proteins can be obtained by constructing a cDNA library from mRNA. DNA molecules encoding EDF proteins can be isolated from such a library using the sequences disclosed herein with standard hybridization techniques or by the amplification of sequences using polymerase chain reaction (PCR) amplification.

In a similar manner, genomic DNA encoding EDF protein homologs can be obtained using probes designed from the sequences disclosed herein. Suitable probes for use in identifying EDF protein homologue sequences can be obtained from edf gene-specific sequences. Alternatively, oligonucleotides containing specific DNA sequences from a edf gene-coding region can be used to identify related edf clones. One of skill in the art will appreciate that the regulatory regions relating to or interacting with the edf genes and homologous genes can be obtained using similar methods.

Polynucleotide molecules having homology with one or more edf genes can be isolated using standard hybridization techniques with probes of at least about 7 nucleotides in length and up to and including the full coding sequence. Homologous edf gene sequences can be identified using degenerate oligonucleotides capable of hybridization based on the sequences disclosed herein for use PCR amplification or by hybridization at moderate or greater stringency. The term, "capable of hybridization" as used herein means that the subject nucleic acid molecules (whether DNA or RNA) anneal to an oligonucleotide of 15 or more contiguous nucleotides.

The choice of hybridization conditions will be evident to one skilled in the art and will generally be guided by the purpose of the hybridization, the type of hybridization (DNA—DNA or DNA-RNA), and the level of desired relatedness between the sequences. Methods for hybridization are well established in the literature. One of ordinary skill in the art realizes that the stability of nucleic acid duplexes will decrease with an increased number and location of mismatched bases; thus, the stringency of hybridization can be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/ or the temperature, resulting in progressively higher stringency conditions.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/ 0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. As mentioned above, however, optimal conditions will vary, depending on the particular hybridization reaction involved, and can be determined empirically. In general, conditions of high stringency are used for the hybridization of the probe of interest.

Alternatively, polynucleotides having substantially the same nucleotide sequences as those provided in the disclosed edf genes, or functional fragments thereof, or nucleotide sequences that are substantially identical to the disclosed sequences can represent members of the EDF gene family. By "substantially the same" or "substantially identical" is meant a nucleic acid or polypeptide exhibiting at least 80%, 85%, 90%, 91%, 92%, 93%, 94%, 95%, 96%, 97%, 98%, 99%, or 100% homology to a reference nucleic acid. For nucleotide sequences, the length of comparison sequences will generally be at least 10 to 500 nucleotides in length. More specifically, the length of comparison will be at least 50 nucleotides, at least 60 nucleotides, at least 75 nucleotides, and at least 110 nucleotides in length.

One embodiment of the invention provides isolated and purified polynucleotide molecules encoding one or more EDF proteins, wherein the polynucleotide molecules that are capable of hybridizing under moderate to stringent conditions to an oligonucleotide of 15 or more contiguous nucleotides of the disclosed EDF sequences, including complementary strands thereto.

DNA sequences of the invention can be obtained by several methods. For example, the DNA can be isolated using hybridization or computer-based techniques which are well known in the art. Such techniques include, but are not limited to: 1) hybridization of genomic or cDNA libraries with probes to detect homologous nucleotide sequences; 2) antibody screening of expression libraries to detect cloned DNA fragments with shared structural features; 3) polymerase chain reaction (PCR) on genomic DNA or cDNA using primers capable of annealing to the DNA sequence of interest; 4) computer searches of sequence databases for similar sequences; and 5) differential screening of a subtracted DNA library.

Screening procedures which rely on nucleic acid hybridization make it possible to isolate any gene sequence from any organism, provided the appropriate probe is available. Oligonucleotide probes, which correspond to a portion of an EDF gene sequence provided herein and encoding a EDF protein, can be synthesized chemically. This synthesis requires that short, oligo-peptide stretches of the amino acid sequence be known. The DNA sequence encoding the protein can be deduced from the genetic code, however, the degeneracy of the code must be taken into account. It is possible to perform a mixed addition reaction when the sequence is degenerate. This includes a heterogeneous mixture of denatured double-stranded DNA. For such screening, hybridization is preferably performed on either single-stranded DNA or denatured double-stranded DNA. Hybridization is particularly useful in the detection of cDNA clones derived from sources where an extremely low amount of mRNA sequences relating to the polypeptide of interest are present. In other words, by using stringent hybridization conditions directed to avoid non-specific binding, it is possible, for example, to allow the autoradiographic visualization of a specific cDNA clone by the hybridization of the target DNA to that single probe in the mixture that is its complete complement. (Wallace, et al., Nucl. Acid Res., 9:879, 1981). Alternatively, a subtractive library is useful for elimination of non-specific cDNA clones.

Among the standard procedures for isolating cDNA sequences of interest is the formation of plasmid- or phage-carrying cDNA libraries which are derived from reverse transcription of mRNA which is abundant in donor cells that have a high level of gene expression. When used in combination with polymerase chain reaction technology, even rare expression products can be cloned. In those cases where significant portions of the amino acid sequence of the polypeptide are known, the production of labeled single or double-stranded DNA or RNA probe sequences duplicating a sequence putatively present in the target cDNA can be employed in DNA/DNA hybridization procedures which are carried out on cloned copies of the cDNA which have been denatured into a single-stranded form (Jay, et al., Nucl. Acid Res., 11:2325, 1983).

The nucleotide sequences of the present invention have a myriad of applications. Representative uses of the nucleotide sequences of the invention include the construction of cDNA and oligonucleotide probes useful in Northern, Southern, and dot-blot assays for identifying and quantifying the level of expression of a EDF protein in a cell. EDF proteins have a variety of uses, for example, as a means by which to modulate an organism's sensitivity to ethylene.

When the EDF coding regions are used in the construction of various types of vectors, the sequences are often inserted into the coding region of the vector under the control of a promoter. Additionally, other elements, including regulatory elements, which are commonly found in vectors suitable for use in various molecular biology techniques, can also be included.

In one embodiment, a vector comprising a DNA molecule coding a EDF protein is provided. Preferably, a DNA molecule encoding a EDF1, EDF2, EDF3, OR EDF4 or a combination of these genes, either wildtype or mutated, is inserted into a suitable expression vector, which is in turn used to transfect or transform a suitable host cell. Exemplary expression vectors include a promoter capable of directing the transcription of a polynucleotide molecule of interest in a host cell. Representative expression vectors include both plasmid and/or viral vector sequences. Suitable vectors include retroviral vectors, vaccinia viral vectors, CMV viral vectors, BLUESCRIPT (Stratagene, San Diego, Calif.) vectors, bacculovirus vectors, and the like. In another embodiment, promoters capable of directing the transcription of a cloned gene or cDNA can be inducible or constitutive promoters and include viral and cellular promoters. In particularly preferred embodiments, viral vectors are employed for use in expressing EDF proteins in pathogenic bacterial organisms, particularly bacterial organisms that cause disease in mammals, such as humans.

In some embodiments, it can be preferable to use a selectable marker to identify cells that contain the cloned DNA. Selectable markers are generally introduced into the cells along with the cloned DNA molecules and include genes that confer resistance to drugs, such as ampicillin, neomycin, hygromycin, and methotrexate. Selectable markers can also complement auxotrophies in the host cell. Other selectable markers provide detectable signals, such as beta-galactosidase to identify cells containing the cloned DNA molecules. Advantageously, the selectable markers are amplifiable. Such amplifiable selectable markers can be used to amplify the number of sequences integrated into the host genome.

Antisense

Antisense EDF nucleotide sequences can be used to block EDF gene expression. Suitable antisense oligonucleotides are at least 11 nucleotides in length and can include untranslated (upstream) and associated coding sequences. As will be evident to one skilled in the art, the optimal length of an antisense oligonucleotide depends on the strength of the interaction between the antisense oligonucleotide and the complementary mRNA, the temperature and ionic environment in which translation takes place, the base sequence of the antisense oligonucleotide, and the presence of secondary and tertiary structure in the mRNA and/or in the antisense oligonucleotide. Suitable target sequences for antisense oligonucleotides include initiation factor binding sites, ribosome binding sites, and sites that interfere with ribosome progression.

Antisense oligonucleotides can be prepared, for example, by the insertion of a DNA molecule containing the target DNA sequence into a suitable expression vector such that the DNA molecule is inserted downstream of a promoter in a reverse orientation as compared to the particular EDF gene itself. The expression vector can then be transduced, transformed or transfected into a suitable cell resulting in the expression of antisense oligonucleotides. Alternatively, antisense oligonucleotides can be synthesized using standard manual or automated synthesis techniques. Synthesized oligonucleotides are introduced into suitable cells by a variety of means including electoporation, calcium phosphate precipitation, or microinjection. The selection of a suitable antisense oligonucleotide administration method will be evident to one skilled in the art.

With respect to synthesized oligonucleotides, the stability of antisense oligonucleotide-mRNA hybrids is advantageously increased by the addition of stabilizing agents to the oligonucleotide. Stabilizing agents include intercalating agents that are covalently attached to either or both ends of the oligonucleotide. In preferred embodiments, the oligonucleotides are made resistant to nucleases by, for example, modifications to the phosphodiester backbone by the introduction of phosphotriesters, phosphonates, phosphorothioates, phosphoroselenoates, phosphoramidates, phosphorodithioates, or morpholino rings.

Polypeptides

The disclosure also relates to purified EDF proteins. As used herein, the term "substantially pure" as used herein refers to polypeptides which are substantially free of other proteins, lipids, carbohydrates or other materials with which it is naturally associated. One skilled in the art can purify a polypeptide using standard techniques for protein purification. The purity of a polypeptide can also be determined by amino-terminal amino acid sequence analysis.

Embodiments of the disclosure also include functional EDF polypeptides, and functional fragments thereof. As used herein, the term "functional polypeptide" refers to a polypeptide which possesses biological function or activity which is identified through a defined functional assay and which is associated with a particular biologic, morphologic, or phenotypic alteration in the cell. The term "functional fragments of EDF polypeptides," refers to all fragments of the various EDF proteins that retain EDF activity, e.g., responsiveness to ethylene. Biologically functional fragments, for example, can vary in size from a polypeptide fragment as small as an epitope capable of binding an antibody molecule to a large polypeptide capable of participating in the characteristic induction or programming of phenotypic changes within a cell.

Many modifications of the primary amino acid sequence of various EDF proteins may result in plants having reduced or abolished ethylene responses. Such modifications may be deliberate, as by site-directed mutagenesis, or may be spontaneous. All of the polypeptides produced by these modifications are included herein as long as the biological activity of EDF is present. Further, deletion of one or more amino acids can also result in a modification of the structure of the resultant molecule without significantly altering its activity. This can lead to the development of a smaller active molecule which could have broader utility. For example, it may be possible to remove amino or carboxy terminal amino acids required for EDF activity.

EDF polypeptides include amino acid sequences substantially the same as the sequence set forth below, including mutants that result in plants having altered ethylene responsiveness. The term "substantially the same" refers to amino acid sequences that retain the activity of a EDF protein as described herein. The EDF polypeptides of the invention include conservative variations of the polypeptide sequence.

The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

EDF proteins can be analyzed by standard sds-page and/or immunoprecipitation analysis and/or western blot analysis, for example. Isolation and purification of recombinantly expressed polypeptide, or fragments thereof, may be carried out by conventional means including preparative chromatography and immunological separations involving monoclonal or polyclonal antibodies.

Preparation and Use of EDF Antibodies

Aspects of the invention also include antibodies immunoreactive with EDF polypeptides or antigenic fragments thereof. Antibodies which consists essentially of pooled monoclonal antibodies with different epitopic specificities, as well as distinct monoclonal antibody preparations are provided. Monoclonal antibodies are made from antigen containing fragments of the protein by methods well known to those skilled in the art (Kohler, et al., Nature, 256:495, 1975).

Antibodies which bind to a EDF polypeptide can be prepared using an intact polypeptide or fragments containing small peptides of interest as the immunizing antigen or "epitope". For example, it may be desirable to produce antibodies that specifically bind to the N- or C-terminal domains of an EDF protein. The polypeptide or peptide used to immunize an animal which is derived from translated cDNA or chemically synthesized which can be conjugated to a carrier protein, if desired. Such commonly used carriers which are chemically coupled to the immunizing peptide include keyhole limpet hemocyanin (KLH), thyroglobulin, bovine serum albumin (BSA), and tetanus toxoid.

As used in this invention, the term "epitope" refers to an antigenic determinant on an antigen to which the paratope of an antibody binds. Epitopic determinants usually consist of chemically active surface groupings of molecules such as amino acids or sugar side chains and usually have specific three dimensional structural characteristics, as well as specific charge characteristics.

The term "antibody" as used in this invention includes intact molecules as well as fragments thereof, such as Fab, F(ab')2, and Fv which are capable of binding to an epitopic determinant present in a EDF polypeptide. Such antibody fragments retain some ability to selectively bind with its antigen or receptor. Methods of making these fragments are known in the art. (See for example, Harlow and Lane, Antibodies: A Laboratory Manual, Cold Spring Harbor Laboratory, New York (1988), incorporated herein by reference).

Polyclonal or monoclonal antibodies can be further purified, for example, by binding to and eluting from a matrix to which the polypeptide or a peptide to which the antibodies were raised is bound. Those of skill in the art will know of various techniques common in the immunology arts for purification and/or concentration of polyclonal antibodies, as well as monoclonal antibodies (See for example, Coligan, et al., Unit 9, Current Protocols in Immunology, Wiley Interscience, 1994, incorporated by reference).

It is also possible to use the anti-idiotype technology to produce monoclonal antibodies which mimic an epitope. For example, an anti-idiotypic monoclonal antibody made to a first monoclonal antibody will have a binding domain in the hypervariable region which is the "image" of the epitope bound by the first monoclonal antibody.

Genetically Modified Plants Having Altered Sensitivity to Ethylene

In another embodiment, the embodiments of the invention provide a method for producing a genetically modified plant characterized as having an altered ethylene-dependent phenotype as compared to a plant which has not been genetically modified (e.g., a wild-type plant). The method includes the steps of contacting a plant cell with at least one vector containing at least one nucleic acid sequence encoding an EDF gene or a mutant, homolog or fragment thereof, wherein the nucleic acid sequence is operably associated with a promoter, to obtain a transformed plant cell; producing a plant from the transformed plant cell; and thereafter selecting a plant exhibiting an altered ethylene-dependent phenotype.

Transgenic plants that result in an altered ethylene-dependent phenotype may be obtained by reduced expression of one or more EDF genes. In accordance with one embodiment of the present invention, there is provided antisense polynucleotides, complementary to an EDF gene or fragments thereof. Plants transformed with such polynucleotides, operably linked to a suitable promoter as described above would have an altered ethylene-dependent phenotype. In an alternate embodiment, reduced expression of edf may also be effected by methods such as cosuppression.

Suppression of EDF genes in a seed plant can be achieved using cosuppression, which is a well known methodology that relies on expression of a nucleic acid molecule in the sense orientation to produce coordinate silencing of the introduced nucleic acid molecule and the homologous endogenous genes (see, for example, Elavell, Proc. Natl. Acad. Sci., USA 91:3490–3496 (1994); Kooter and Mol, Current Opin. Biol. 4:166–171 (1993), each of which is incorporated herein by reference). Cosuppression is induced most strongly by a large number of transgene copies or by overexpression of transgene RNA and can be enhanced by modification of the transgene such that it fails to be translated.

In one embodiment, one or more of the edf genes are cosuppressed by overexpression of conservative domains of the edf genes. In another embodiment, cosuppression is accomplished by operatively linking a truncated form of an edf gene to a promoter, and thereafter transforming a plant.

The term "genetic modification" as used herein refers to the introduction of one or more heterologous nucleic acid sequences, e.g., an edf or an edf mutant encoding sequence, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants. Accordingly, a seed comprising multiple plant cells capable of regenerating into a whole plant, is included in the definition of "plant cell".

As used herein, the term "plant" refers to either a whole plant, a plant part, a plant cell, or a group of plant cells, such as plant tissue, for example. Plantlets are also included within the meaning of "plant". Plants included in the invention are any plants amenable to transformation techniques, including angiosperms, gymnosperms, monocotyledons and dicotyledons.

Examples of monocotyledonous plants include, but are not limited to, asparagus, field and sweet corn, barley, wheat, rice, sorghum, onion, pearl millet, rye and oats. Examples of dicotyledonous plants include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, Brussels sprouts), radish, carrot, beets, eggplant, spinach, cucumber, squash, melons, cantaloupe, sunflowers and various ornamentals. Woody species include poplar, pine, *sequoia*, cedar, oak, etc.

The term "exogenous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In one embodiment, at least one nucleic acid sequence encoding an edf gene or a variant thereof is operably linked with a promoter. It may be desirable to introduce more than one copy of an edf polynucleotide into a plant for enhanced expression. For example, multiple copies of the gene would have the effect of increasing production of one or more edf gene products in the plant.

Vector Construction

Genetically modified plants of the present invention are produced by contacting a plant cell with a vector including at least one nucleic acid sequence encoding a EDF gene or a variant thereof. Accordingly, it is first necessary to construct a suitable vector and properly introduce it into the plant cell. Details of the construction of vectors utilized herein are known to those skilled in the art of plant genetic engineering.

Vector(s) employed in the present invention for transformation of a plant cell include a nucleic acid sequence encoding an EDF protein, operably linked to a promoter. The term "operably linked" refers to functional linkage between a promoter sequence and a nucleic acid sequence regulated by the promoter. The operably linked promoter controls the expression of the nucleic acid sequence. One of skill in the art will be able to select an appropriate vector for introducing the EDF-encoding nucleic acid sequence in a relatively intact state. Thus, any vector which will produce a plant carrying the introduced DNA sequence should be sufficient. Even use of a naked piece of DNA would be expected to confer the properties of this invention, though at low efficiency. The selection of the vector, or whether to use a vector, is typically guided by the method of transformation selected.

To be effective once introduced into plant cells, the EDF nucleic acid sequence should be operably linked with a promoter which is effective in the plant cells to cause transcription of an edf gene. Additionally, a polyadenylation sequence or transcription control sequence, also recognized in plant cells may also be employed. It is preferred that the vector harboring the nucleic acid sequence to be inserted also contain one or more selectable marker genes so that the transformed cells can be selected from non-transformed cells in culture, as described herein.

The expression of structural genes may be driven by a number of promoters. Although the endogenous, or native promoter of a structural gene of interest may be utilized for transcriptional regulation of the gene, preferably, the promoter is a foreign regulatory sequence. For plant expression vectors, suitable viral promoters include the 35S RNA and 19S RNA promoters of CaMV (Brisson, et al., Nature, 310:511, 1984; Odell, et al., Nature, 313:810, 1985); the full-length transcript promoter from Figwort Mosaic Virus (FMV) (Gowda, et al., J. Cell Biochem., 13D: 301, 1989) and the coat protein promoter to TMV (Takamatsu, et al., EMBO J. 6:307, 1987). Alternatively, plant promoters such as the light-inducible promoter from the small subunit of ribulose bis-phosphate carboxylase (ssRUBISCO) (Coruzzi, et al., EMBO J., 3:1671, 1984; Broglie, et al., Science, 224:838, 1984); mannopine synthase promoter (Velten, et al., EMBO J., 3:2723, 1984) nopaline synthase (NOS) and octopine synthase (OCS) promoters (carried on tumor-inducing plasmids of *Agrobacterium tumefaciens*) or heat shock promoters, e.g., soybean hsp17.5-E or hsp17.3-B (Gurley, et al., Mol. Cell. Biol., 6:559, 1986; Severin, et al., Plant Mol. Biol., 15:827, 1990) may be used.

Promoters useful in the invention include both natural constitutive and inducible promoters as well as engineered promoters. The CaMV promoters are examples of constitutive promoters. To be most useful, an inducible promoter should 1) provide low expression in the absence of the inducer; 2) provide high expression in the presence of the inducer; 3) use an induction scheme that does not interfere with the normal physiology of the plant; and 4) have no effect on the expression of other genes. Examples of inducible promoters useful in plants include those induced by chemical means, such as the yeast metallothionein promoter which is activated by copper ions (Mett, et al., Proc. Natl. Acad. Sci., U.S.A., 90:4567, 1993); In2-1 and In2-2 regulator sequences which are activated by substituted benzenesulfonamides, e.g., herbicide safeners (Hershey, et al., Plant Mol. Biol., 17:679, 1991); and the GRE regulatory sequences which are induced by glucocorticoids (Schena, et al., Proc. Natl. Acad. Sci., U.S.A., 88:10421, 1991). Other promoters, both constitutive and inducible will be known to those of skill in the art.

The particular promoter selected should be capable of causing sufficient expression to result in the production of an effective amount of a gene product, e.g., an EDF mutant, to cause an altered phenotype, e.g., cause increased yield and/or increased biomass.

Tissue specific promoters may also be utilized in the present invention. An example of a tissue specific promoter is the promoter active in shoot meristems (Atanassova, et al., Plant J., 2:291, 1992). Other tissue specific promoters useful in transgenic plants, including the cdc2a promoter and cyc07 promoter, will be known to those of skill in the art. (See for example, Ito, et al., Plant Mol. Biol., 24:863, 1994; Martinez, et al., Proc. Natl. Acad. Sci. USA, 89:7360, 1992; Medford, et al., Plant Cell, 3:359, 1991; Terada, et al., Plant Journal, 3:241, 1993; Wissenbach, et al., Plant Journal, 4:411, 1993).

Optionally, a selectable marker may be associated with the nucleic acid sequence to be inserted. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phospho-transferase, thymidine kinase, xanthine-guanine phospho-ribosyltransferase and amino-glycoside 3'-O-phospho-transferase II (kanamycin, neomycin and G418 resistance). Other suitable markers will be known to those of skill in the art.

Plant Transformation Methods

The transformation of plants with active or inactive forms of EDF genes in accordance with the invention may be carried out in essentially any of the various ways known to those skilled in the art of plant molecular biology. As used herein, the term "transformation" means alteration of the genotype of a host plant by the introduction of an EDF or edf mutant nucleic acid sequence.

EDF nucleic acid sequences utilized in the present invention can be introduced into plant cells using ti plasmids of Agrobacterium tumefaciens, root-inducing (ri) plasmids, and plant virus vectors. In addition to plant transformation vectors derived from the ti or root-inducing (ri) plasmids of Agrobacterium, alternative methods may involve, for example, the use of liposomes, electroporation, chemicals that increase free dna uptake, transformation using viruses or pollen and the use of microprojection. For reviews of such techniques see, for example, Methods of Enzymology, Vol. 153, 1987, Wu and Grossman, eds., Academic press; Weissbach & Weissbach, 1988, Methods for Plant Molecular Biology, Academic Press, NY, section viii, pp. 421–463; Grierson & Corey, 1988, Plant Molecular Biology, 2d ed., Blackie, London, ch. 7–9, and Horsch, et al., Science, 227:1229, 1985). These methods are discussed further below.

For example, an EDF nucleic acid sequence can be introduced into a plant cell utilizing Agrobacterium tumefaciens containing the Ti plasmid, as mentioned briefly above. In using an A. tumefaciens culture as a transformation vehicle, it is most advantageous to use a non-oncogenic strain of Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The latter contains at least one border region of the T-DNA region of a wild-type Ti plasmid flanking the nucleic acid to be transferred. Binary Ti plasmid systems have been shown effective to transform plant cells (De Framond, Biotechnology, 1: 262, 1983; Hoekema, et al., Nature, 303:179, 1983). Such a binary system is preferred because it does not require integration into the Ti plasmid of Agrobacterium, which is an older methodology.

Methods involving the use of Agrobacterium in transformation according to the present invention include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold, et al., (C. R. Acad. Sci. Paris, 316:1194, 1993). This approach is based on the vacuum infiltration of a suspension of Agrobacterium cells.

One method of introducing EDF-encoding nucleic acid into plant cells is to infect such plant cells, an explant, a meristem or a seed, with transformed Agrobacterium tumefaciens as described above. Under appropriate conditions known in the art, the transformed plant cells are grown to form shoots, roots, and develop further into plants.

Alternatively, edf encoding nucleic acid sequences can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

Edf nucleic acid sequences can also be introduced into plant cells by electroporation (Fromm, et al., Proc. Natl. Acad. Sci., U.S.A., 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing EDF nucleic acid into a plant cell is high velocity ballistic penetration by small particles with the nucleic acid to be introduced contained either within the matrix of such particles, or on the surface thereof (Klein, et al., Nature 327:70, 1987). Bombardment transformation methods are also described in Sanford, et al. (Techniques 3:3–16, 1991) and Klein, et al. (Bio/Techniques 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing one or more EDF coding sequences (wild type or mutant) into the plant cell, including chemical and physical means as described above. Preferably, contacting refers to introducing the nucleic acid or vector into plant cells (including an explant, a meristem or a seed), via *Agrobacterium tumefaciens* transformed with an EDF encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension, to the stage of ripening and germination as natural embryos. The culture media will generally contain various amino acids and hormones, necessary for growth and regeneration. Examples of hormones utilized include auxins and cytokinins. It is sometimes advantageous to add glutamic acid and proline to the medium, especially for plant species such as corn and alfalfa. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see Methods in Enzymology, Vol. 118 and Klee, et al., Annual Review of Plant Physiology, 38:467, 1987). Utilizing the leaf disk-transformation-regeneration method of Horsch, et al., Science, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, the mature transgenic plants can be self crossed to produce a homozygous inbred plant. The resulting inbred plant produces seed containing the newly introduced foreign gene(s). These seeds can be grown to produce plants that would produce the selected phenotype, e.g. increased yield.

Parts obtained from regenerated plant, such as flowers, seeds, leaves, branches, roots, fruit, and the like are included in the invention, provided that these parts comprise cells that have been transformed as described. Progeny and variants, and mutants of the regenerated plants are also included within the scope of the invention, provided that these parts comprise the introduced nucleic acid sequences.

Phenotype of Transformed Plants Having an Altered Ethylene Sensitivity

Plants exhibiting an altered ethylene-dependent phenotype as compared with wild-type plants can be selected by visual observation. For example, an altered ethylene-dependent phenotype may be detected by utilization of the "triple response." The "triple response" consists of three distinct morphological changes in dark-grown seedlings upon exposure to ethylene: inhibition of hypocotyl and root elongation, radial swelling of the stem and exaggeration of the apical hook. Thus, a triple response displayed in the presence of ethylene inhibitors would indicate one type of altered ethylene-dependent phenotype. Ethylene affects a vast array of agriculturally important plant processes, including fruit ripening, flower and leaf senescence and leaf abscission. The ability to control the sensitivity of plants to ethylene could thus significantly improve the quality and longevity of many crops. The invention includes plants produced by the method of the invention, as well as plant tissue and seeds.

In yet another embodiment, the invention provides a method for producing a genetically modified plant cell such that a plant produced from said cell has an altered ethylene-dependent phenotype compared with a wild-type plant. The method includes contacting the plant cell with an EDF nucleic acid sequence to obtain a transformed plant cell; growing the transformed plant cell under plant forming conditions to obtain a plant having increased yield. Conditions such as environmental and promoter inducing conditions vary from species to species, but should be the same within a species.

It will be understood by those of skill in the art that numerous and various modifications can be made without departing from the spirit of the present invention. A more complete understanding can be obtained by reference to the following specific examples which are provided herein for purposes of illustration only and are not intended to limit the scope of the invention.

Systematic Characterization of the EREBP Family Members in *Arabidopsis*: New Components of the Ethylene Signaling Pathway.

To elucidate the molecular mechanisms of ethylene-responsive gene regulation, efforts were undertaken to understand how the ethylene gas signal is being sensed, transduced via several signaling components and, finally, converted into differential expression of ethylene-regulated genes.

Ethylene Responsive Element Binding Proteins (EREBPs) were originally discovered in tobacco as proteins that in vitro bind to the GCC box in promoters of ethylene-responsive PR genes (Ohme-Takagi and Shinshi, 1995). At least some of tobacco EREBP genes can be transcriptionally induced by an ethylene-releasing compound ethephon (Ohme-Takagi and Shinshi, 1995). In *Arabidopsis*, a number of EST clones and genomic sequences that show homology to tobacco EREBPs can be found (Riechmann and Meyerowitz, 1998). Expression patterns of 20 putative *Arabidopsis* EREBPs were examined by northern blotting in Col-O wild-type plants and in the ethylene insensitive mutant ein2–5 in the presence and in the absence of exogenously supplied ethylene. Four classes of EREBP genes were discovered: ethylene-inducible (ANS118, 119, 122, 124, 125, 128, 136, ERF1), ethylene-repressible (ANS 121, 126, 133), unaffected (ANS 117, 120, 127, 130, 131, 154) and those that can not be detected in etiolated seedlings (ANS 129, 132, 137). The first two classes were further analyzed in a time-course experiment, where wild-type and the ethylene-insensitive ein3-1 adult plants, as well as wild-type seedlings, were treated with the ethylene gas for various periods of time.

Upon repeating of the above ethylene repressibility experiments, two clones (ANS 121 and ANS133) were once again ethylene repressible, but the ethylene repressibility was present in etiolated seedlings but not in adults. This implied that other modes of these genes regulation may take place at later stages of plant development. All putative inducible clones were confirmed on retesting, with the results being even more dramatic in adult plants. Importantly, induction of these genes was suppressed in the ein3-1 mutant, confirming that the observed message level up-regulation is due to ethylene and not due to the general stress associated with the treatment (the latter is observed in the adult plant time-course northern for ANS133). Remarkably, induction kinetics of different clones varied, ranging from 15 minutes in ANS 124, ANS 136 and ERF1 to 4 hours in ANS 119 and ANS 128.

To further differentiate between early and late ethylene response genes, expression of the inducible class of the EREBP genes was examined in the presence of cycloheximide. This protein synthesis inhibitor is known to block induction of the late response genes and induce or super-induce expression of the immediate-early response genes (Abel et al., 1995a; D'Agostino et al., 2000). Message levels for clones ANS118, 124, 136 and ERF1, and to a lesser extent ANS122, increased in the presence of cycloheximide (putative early genes), while that for ANS119 and, to a lesser extent (at low drug concentration only), for ANS128 decreased (putative late genes).

The effect of Col:35S-EIN3 overexpression on EREBP mRNA levels was next examined. EIN3 is predicted to act upstream of the EREBPs and, therefore, may (directly or indirectly) regulate their expression levels. EIN3-overexpressing seedlings that possess a ctr-like morphology in air accumulated slightly higher levels of several EREBP messages (ANS 118, 119, 128 and 136) than did wild-type plants, confirming constitutive activation of ethylene signaling in the transgenic plants. Surprisingly, an ethylene-inducible clone ANS122 had a lower expression level in the transgenic lines, while another inducible clone, ANS124, lost its ability to be up-regulated by the hormone in the EIN3-overexpressing plants. These results indicate that some feedback inhibition is taking place that brings down expression levels of these genes and makes them unresponsive to exogenous ethylene application. Examination of the effect of the EIN3 transgene on the levels of ethylene-repressible messages revealed constitutive inhibition of ANS126 and ANS133, a result consistent with the constitutive activation of ethylene responses in these plants. In contrast, the EIN3 overexpression had no effect on the ANS121 levels suggesting that, instead, EIL proteins, and not EIN3, may regulate expression of this clone. Alternatively, feedback regulation mechanism may contribute to normalization of the ethylene responsiveness of this clone in the transgenic plants.

Isolation of Full-Length cDNAs, Mapping to the Genomic Fragments, and the Predicted Protein Structure Three representative EREBPs were selected for further study: ANS 133, which is ethylene-repressible in seedlings; ANS 136, an immediate-early ethylene inducible gene; and ANS128, a relatively late ethylene-inducible response gene. Full-length cDNA clones were obtained by screening a size-fractionated seedling library with probes made from the partial cDNA clones used in the northern analysis described above. The longest cDNA clones obtained are 1552 bp (ANS133), 1071 bp (ANS128) and 1201 bp (ANS136) in size. Interestingly, the ANS133 cDNA contained an extended 3' end (506 bp after the stop codon).

To determine chromosomal position of the three genes, cDNA clones were hybridized to IGF and TAMU BAC HDR filters. The ANS133 probe recognized BACs F14I14, F15D22, F21F22, F20K20, T13N7, T26H6, T31H18, and T18F21 that map to the top of chromosome 5. ANS 128 recognized BACs F1A23, F2C21, F2K17, F13D19, F26A19, F26J12, F24L9, F2404, T4J18, and T22N19 that belong to the top arm of chromosome 5. Finally, ANS136 hit BACs F3B9, F2J7, F1L7, F4L7, F10B13, F8E6, F14G11, F20F7, F21D22, F22O3, F28D21, T10C17, T10C24 and T19F24 that map to the middle of chromosome 1.

The predicted proteins encoded by the three EREBP genes were analyzed. The expected sizes of ANS133, ANS128 and ANS136 are 335, 212 and 361 aa, respectively. The AP2 domain is located in the N-terminal half of each protein. Importantly, the three proteins have no or little homology to each other outside of the AP2 domain, whereas there are several other proteins in the database to which they are similar along the entire sequence.

ANS133 was found to be identical to DREB2a, and it is also similar to *Arabidopsis* DREB2b/F9F8.16 (53% identity) (Liu et al., 1998; Nakashima et al., 2000), a hypothetical protein T3G21.11/T7M7.24 (29.6%) and a Catharanthus roseus protein ORCA1 (41.3%) (Menke et al., 1998). ANS136 has three paralogs: ANS124/RAV2/Rap2.8/F14K14.5/T6L1.3 (73.2% identity) (Kagaya et al., 1999; Okamuro et al., 1997), RAV1/T6J4.2 (63.4%) (Kagaya et al., 1999), and a hypothetical protein K13N2.7 (57.0%). ANS128 is unique and has no homology to other proteins outside of the AP2 domain. It possesses a serine/glutamic acid/glutamine-rich stretch of amino acids in the C-terminal domain that is predicted to form a coiled-coil.

DNA-Binding Properties of ANS133, ANS128 and ANS136

As described above, the tobacco EREBPs were originally identified as the DNA-binding proteins specifically interacting with the GCC-box in the promoters of several pathogen-related ethylene-responsive genes (Ohme-Takagi and Shinshi, 1995). The binding was mediated by the AP2-domain of the EREBP (Ohme-Takagi and Shinshi, 1995; Okamuro et al., 1997). To determine whether or not the AP2-domain-containing proteins ANS133, ANS128 and ANS136 were also capable of binding to the GCC-box, electrophoretic mobility shift assays were performed. The EREBP proteins were synthesized in the in vitro transcription/translation reactions, co-incubated with the radioactively-labeled GCC-box from the HLS1 promoter and separated on a polyacrylamide gel. Like the positive control ERF1 (Solano et al., 1998), both ANS133 and ANS128 recognized the GCC-box. Interestingly, in another study ANS133/DREB2a has been reported to recognize a GCC-box-related drought-response element (Liu et al., 1998). The last protein, ANS136, did not bind to the GCC box in our assay, and neither did its close paralog ANS124. This result may be explained by either the poor quality of the latter proteins, or by their true inability to interact with the GCC-box. Consistent with the second possibility, upon careful examination of the ANS136 and ANS124 amino acid sequences, several changes in the conserved residues of the AP2 domain were discovered (see below).

Reverse Genetics as a Means to Study the in planta Role of EREBPs

To address the role of ANS133, ANS128 and ANS136 in vivo, transgenic lines overexpressing the genes of interest under the control of a constitutive cauliflower mosaic virus 35S promoter were generated. In addition, publicly available T-DNA collections were screened for the knockouts in the EREBPs of interest.

A PCR-based approach was employed to screen 12 pools of 1000 independent lines (6×1000 of K. Feldmann and 6×1000 of T. Jack) available through the *Arabidopsis* Biological Resource Center (The Ohio State University, Columbus, Ohio). Two gene-specific primers were designed for each of the three genes, one in the forward and one in the reverse orientation, facing each other and about 500 bp apart. Several putative positives were identified for each of the genes in the first round of screening. In the second round, about fifty percent of putative positive clones were confirmed, yielding the total of 5 mutants. As many as three insertions were identified in the ANS133 gene. The first mutant (dreb2a-1, CS12008, KF collection) harbors insertion inside of the open reading frame and is predicted to cause a truncation after the amino acid 187. The second mutant (dreb2a-2, CS15488, KF collection) is disrupted in the promoter of ANS133, about 1 kb upstream of the translation start site. The third mutant (dreb2a-3, CS19784, TJ collection) has the T-DNA inserted in the promoter 589 bp upstream of the ATG. Phenotypic characterization of the three mutants in air and ethylene/ACC failed to reveal any abnormalities. A northern blot analysis was performed on adult plants to analyze the levels of expression of ANS133 in the mutants. Although a very weak signal was obtained, dreb2a-1 clearly showed a shift in a transcript size and, possibly, a reduction in the transcript level. It is not known whether the predicted 187 amino-acid long truncated version of the protein is functional. Mutants dreb2a-2 and dreb2a-3 showed wild-type levels of ANS133 expression.

One mutant was obtained for the ANS136 gene (edf1-1, CS13986, KF collection) and sequencing revealed that the T-DNA inserted 185 bp upstream of the ATG. Although northern blot analysis revealed no ANS136 mRNA made in the mutant (data not shown), its phenotype was indistinguishable form the wild-type WS plants.

Finally, in search for mutations in ANS128 a T-DNA line (k19e1.6-1, CS12929, KF collection) was recovered that had an insertion in a hypothetical EREBP from the TAC clone K19E1 (K19E1.6). However, the insertion site, as determined by sequencing, was 143 bp downstream of the predicted stop codon. No phenotype was observed in this line.

Since the loss-of-function mutant approach did not unveil (uncover) the in vivo function of the EREBPs (possibly, due to functional redundancy of multiple EREBP family members), a transgenic gain-of-function approach was next performed. Full-length ANS128, ANS133 and a partial clone of ANS136 (the longest available at that time) which lacked the start codon and the five following nucleotides (and is predicted to give rise to a 39aa truncation in the amino-terminus of the respective protein) were cloned into the pROK2 vector (Baulcombe et al., 1986) in both sense and antisense orientation under the control of the 35S promoter. The constructs were introduced into plants via *Agrobacterium*-mediated vacuum infiltration of flowering adult plants. Three genetic backgrounds were used in this experiment: wild-type Col-0 and ethylene-insensitive ein3-1 and ein2-5. The vector used allows for selection of primary plant transformants (T1s) on AT plates supplemented with 100 mg/ml kanamycin as a selectable marker. More than 100 lines were obtained and analyzed for each of the construct/mutant combinations. Heterozygous T1 adult plants, as well as segregating T2 seedlings and kanamycin-resistant T2 adults (heterozygous and homozygous for the transgene), were analyzed phenotypically. Seedling phenotypes were examined in plain AT plates, as well as in AT plates supplemented with 10 uM ethylene precursor ACC. No phenotype (neither in seedlings nor in adults) was observed for the sense and antisense lines of the repressible gene ANS133. In contrast, adult plants overexpressing ANS128 gave a rather dramatic phenotype: 80% of the original T1 lines and a similar proportion in later generations were bushy in adults, with long, thin and spindly inflorescences. Remarkably, this reduced apical dominance phenotype was identical in the wild-type plants and in the ethylene-insensitive mutants ein3-1 and ein2-5. The seedlings of the 35S-ANS128 lines, however, possessed a wild-type morphology.

Transformation of plants with the truncated version of ANS136 (from now on referred to as dEDF1) in sense orientation, 35S-dEDF1, triggered multiple phenotypes, including increased root growth. About 80% of kanamycin resistant T1 seedlings were extremely delayed in germination (compared to T1 transformants harboring other constructs) and many gave rise to dwarf-looking adults. The vast majority of these lines were adult-lethal: the dwarfs flowered but were unable to set seeds. The defect appears to be mostly due to male sterility, as at least some of the dwarf plants were able to set seeds when cross-pollinated with the wild-type pollen.

A more detailed analysis of dwarf plants revealed resemblance to the ctr1 mutants (Kieber et al., 1993) in several aspects: the small rosette size, dark green color and epinastic curling of leaves, short inflorescences, and a significantly reduced root mass. However, unlike ctr1, dEDF1-overexpressing dwarfs also displayed reduced apical dominance and, often, flowers lacking petals. In the most dramatic cases, plants overexpressing dEDF1 formed a miniature rosette of about 1 cm in diameter, never flowered but kept making leaves (20 or more) and eventually senesced and died. The remaining 20% of kanamycin-resistant T1 plants had normal germination and were largely wild-type in appearance.

Occasionally, a reversion to dwarf morphology was observed, with the first few leaves developing normally and the later leaves being small, dark-green and epinastic. Conversely, an otherwise normal plant would make an apetala-like inflorescence, often adjacent to the one with wild-type flowers. And, vice versa, a small number of initially dwarf-looking plants reverted to normal and set seeds.

In the T2 generation of 35S-dEDF1 plants a variety of phenotypes were observed: from normal looking seedlings to, again, extremely late germinating (up to two weeks late). Many lines showed dwarf morphology, reminiscent of the partial constitutive ethylene response: shortening and radial swelling of hypocotyl, inhibition of root elongation, but no exaggeration of the apical hook curvature. Absence of the hook was observed not only in air, but also in ethylene/ACC, and in most dramatic cases the strong hookless phenotype of the transgenic lines was phenotypically indistinguishable from that of the hls1 mutant (Guzman and Ecker, 1990). In air, 8 day-old dark grown seedlings of these transgenic lines looked like three-day old dark grown ethylene-treated hls1 seedlings (this longer time was required to see the phenotype of the transgenic plants to compensate for their delayed germination).

Interestingly, segregants in several dEDF1-overexpression lines also showed a completely rootless phenotype in seedlings. A gradation of rootless phenotypes could be found, as shown for the ein2-5:35S-dEDF1 seedlings: from normal root to absolutely no root. If kept in plates, some of the rootless seedlings eventually made secondary roots out of the hypocotyls, whereas others died. Often, seedlings that possessed short primary roots also displayed significant thickening of the root-hypocotyl junction. Many independent lines showed ectopic root hair formation, with root hairs often covering the entire hypocotyl. This phenotype can be further enhanced by addition of ACC to transformants generated in the Col-0 background. In more severe cases, root hairs and even entire roots emerged from the cotyledons.

Remarkably, upon prolonged growth on AT plates for over two weeks, hypocotyls and/or cotyledons of some lines degenerated into callus-like structures. Callus formation begun either with individual cells peeling off the plant, or with yellowing and thickening of an intact hypocotyl or cotyledon and cell "bubbling". Interestingly, presence of kanamycin in the medium enhanced callus formation (possibly, by selecting for higher transgene expression). The callus-like structures could be detached from the plant and propagated in tissue culture in a hormone-free medium for several months. While in majority of cases calluses appeared as a mass of undifferentiated cells and hair-covered roots, some calluses eventually formed multiple green shoots.

Importantly, all phenotypes described for the dEDF1 overexpression (except for the ACC-mediated enhancement of ectopic root hair formation) were characteristic not only of the Col-0:35S-dEDF1 transformants, but also of the transgenic lines made in the ein3-1 and ein2-5 backgrounds. Thus, they were a result of a constitutive activation of a downstream branch of the ethylene pathway that is independent of the upstream ethylene signaling events.

The levels of ANS136/EDF1 mRNA were next analyzed in the transgenic lines to determine whether the described phenotypes were, in fact, the result of overexpression or co-suppression. Northern blot analysis of total RNA from individual T1 plants showed that normal-looking plants had similar to wild-type levels of EDF1 and significant degradation of the transgene message, as inferred from the smears. In contrast, dwarf plants had significantly higher than wild-type levels of the EDF1 mRNA, indicating that the dwarfism is a result of overexpression. Similarly, northern blot analysis showed that other phenotypes of the transgenic lines, including apetala-like flowers in adults, rootless and/or hookless seedling morphology and callus formation, are due to the dEDF1-overexpression.

The effect of the 35S-dEDF1 transgene on the expression of ethylene-inducible genes was also examined. Expression of the basic chitinase gene which harbors a functional GCC-box in its promoter (Solano et al., 1998) was unchanged in the 35S-dEDF1 dwarf and normal-looking adult plants, consistent with the inability of ANS 136/EDF1 to bind to the GCC-box in vitro. Expression of three ethylene inducible EREBPs in the 35S-dEDF1 lines was, however, modified. ANS124 was up-regulated in the normal-looking transgenic plants in the Col background, but not in the lines made in the ethylene-insensitive background, indicating that functional ethylene signaling is required for this enhancement. Interestingly, ANS124 is homologous to ANS136/EDF1 not only in the AP2-domain, but throughout the entire length of the protein, suggesting that the observed up-regulation of ANS124 in the transgenic lines is the plant's mechanism to compensate for the high ANS136/dEDF1 message degradation rate. Lack of such compensation in ein2-5 and ein3-1 is in agreement with the dEDF1-overexpression/degradation triggering activation of the ethylene signaling pathway and implies feedback regulation. Another ethylene-inducible clone, ANS128, was slightly up-regulated in the dwarf lines (presumably, due to constitutive activation of the downstream ethylene signaling branch), whereas ethylene-inducible ANS119/AtEBP (Buttner and Singh, 1997) was somewhat inhibited in these lines (possibly, due to negative feedback regulation), irrespective of their genetic background.

dEDF1 Overexpression and Ethylene

To further confirm that the overexpression of dEDF1 results in the constitutive activation of the downstream ethylene signaling events, the 35S-dEDF1 transgenic lines were crossed to the ethylene-inducible reporter T116. The reporter consists of the CTR1 promoter and the open reading frame of GUS (Kieber and Ecker, unpublished). No GUS staining was observed in the reporter line when germinated and grown in air for three days in the dark. However, in seedlings grown in the presence of 10 ppm ethylene the cotyledons and the apical part of the hypocotyl that forms hook stain for GUS. This staining is rather dramatic and is specific to ethylene, making T116 an ideal ethylene reporter. Interestingly, the *Arabidopsis* mutant hls1 that is unable to form hook (Guzman and Ecker, 1990; Lehman et al., 1996), fails to stain in this area of the plant in response to ethylene treatment, while retaining staining in the cotyledons.

When the T116 reporter was crossed into the dEDF1-overexpressing lines that possess partial triple response (short and thick hypocotyl and root), the area of GUS staining in ethylene expands and involves basically the entire seedling, as shown for the 8-day-old dark grown seedlings. This result implies that EDF1 is the factor that determines the spatially limited expression of the T116 reporter. Interestingly, although EDF1 seems to be required for the ethylene-mediated induction of the reporter, it alone is not sufficient to trigger the staining: no GUS activity was observed in the air-grown seedlings. Thus, the functional ethylene pathway "brings in" some other component(s) which, in combination with the EDF1 activity, turns the reporter 'on'.

ANS136 is a Member of the EDF Protein Subfamily that Possess Two Functional DNA-Binding Domains In light of multiple dramatic phenotypes in the transgenic lines overexpressing the truncated version of ANS136, further functional study of this gene was pursued. As described above, the loss-of-function mutant of ANS136 did not exhibit any abnormalities. One possible explanation for this result is functional redundancy with other genes. It was therefore decided to concentrate on the entire EREBP subfamily, of which there are four members in *Arabidopsis*, as revealed by the genome sequencing project: three on chromosome 1 (EDF1/ANS136, EDF2/ANS124 and EDF4/RAV1) and one on chromosome 3 (EDF3/K13N2.7). All four Ethylene Response DNA-Binding Factors (EDFs), in addition to the AP2 domain, possess another highly conserved region.

A BLAST search of this part of the protein revealed distant similarity to the B3 DNA-binding domain of FUSCA3 (Luerssen et al., 1998), ABI3 (Giraudat et al., 1992), MONOPTEROUS/IAA24 (Hardtke and Berleth, 1998), ARF7/NPH4/BIPOSTO (Harper et al., 2000) and several other ARF proteins (Guilfoyle et al., 1998) from *Arabidopsis*. Importantly, sequence identity between these proteins and EDFs in the B3 domain is much lower than between the members of the EDF family itself. Furthermore, BLAST searching also picked up several hypothetical proteins from the genome sequencing project that are highly identical to EDFs in the B3 domain, but are otherwise unrelated (T25K16.3 from chr1, F14M4.30 and F9C22.1 from chr2, F21F14.140 and F24K9.25 from chr3, F11O4.9 from chr4, and MHF15.23 from chr5). Finally, there are two entries in the database that were referred to as EDF-LIKE1 (EDL1/At1g50680) and EDL2/At1g5120, that possess a distant similarity to the EDF proteins both in the AP2 and B3 domain.

Detailed analysis of the AP2 domain of the EDF proteins revealed several changes in the amino acids conserved among other EREBPs. The basically charged YRG element of the AP2 domain that is thought to form the DNA-binding interface (Okamuro et al., 1997) is especially divergent in the EDF proteins compared to that in the classical EREBPs. Interestingly, in the majority of cases these changes are identical in all four EDF proteins, which implies that these amino acid substitutions may account for a changed DNA-binding specificity (and, thus, no recognition of the GCC-box).

In fact, one of the members of the EDF family, RAV1/EDF4, has been recently reported to bind to a binary recognition sequence (unrelated to the GCC-box) in vitro in a random-site-selection experiment (Kagaya et al., 1999). The two DNA-binding domains of RAV1, AP2-like and B3-like, made contact with two DNA elements (CAACA and CACCTC, respectively) present in either orientation with respect to each other and separated by a 3 to 9 nucleotide-long spacer. Remarkably, truncated versions of RAV1 that lack one of the two DNA-binding domains still bound to the DNA, but with much lower affinity than the full-length protein (Kagaya et al., 1999).

To test, whether EDF1 (ANS136) and EDF2 (ANS124) also possess DNA-binding properties, these proteins were expressed in *E. coli* as GST-fusions. Unfortunately, the proteins were largely insoluble and only trace amounts of EDF1-GST and EDF2-GST were detected in the soluble (supernatant) fraction. This amount of protein was, however, sufficient to observe band retardation in an electrophoretic mobility shift assay. A 46 bp long DNA fragment '6-1', that had been previously reported to efficiently bind RAV1 (Kagaya et al., 1999), was radioactively labeled, co-incubated with 1.5 (l of the total soluble fraction from the recombinant *E. coli* cell extracts and separated on a polyacrylamide gel. Both EDF1-GST and EDF2-GST bound the RAV1-binding site (RBS) with high affinity, whereas GST alone did not. Furthermore, neither of the proteins recognized a mutant version of RBS, confirming that both EDF1 and EDF2 are sequence-specific DNA-binding proteins. A similar experiment with the EDF3 (K13N2.7) protein was not performed, however, based on the sequence similarity of its two DNA-binding domains to that of the other EDF proteins it can be predicted that EDF3 will also recognize the wild-type version of the RBS.

The in vitro translated protein preparations of EDF1/ANS136 and EDF2/ANS124 that failed to bind to the GCC-box were tested for their ability to retard the '6-1' DNA fragment. Both proteins bound to the radioactively labeled RBS, whereas ERF1, ANS133, ANS128, all of which recognize the GCC-box, did not bind to the radioactively labeled RBS. From these experiments it was concluded that the EDF family members have a DNA-binding specificity different from that of the classical GCC-box recognizing proteins and, thus, are not to be grouped together with the EREBPs.

Expression of all Four EDF Family Members is Ethylene-Inducible

In order to test whether EDF2, EDF3 and EDF4 were also subject to ethylene-mediated regulation, expression of these genes was examined in the presence of ethylene gas. Interestingly, EDF2, EDF3 and EDF4 all showed early kinetics of induction by ethylene in wild type but not in the ein2-5 mutant plants. The promoter sequences of the EDF2, EDF3 and EDF4 genes were therefore checked for the presence of the putative EIN3-binding site (EBS). Not surprisingly, these genes possess a DNA element highly reminiscent of the EBS from EDF1 and ERF1, implying that the EIN3 protein may be involved in the transcriptional regulation of EDF2, EDF3 and EDF4, as well. The predicted EBS consensus sequence is AgGGGGgATGaAct (SEQ ID NO: 71).

Consistent with EDF2, EDF3 and EDF4 working immediately downstream of EIN3 in the ethylene signal transduction, they were also up-regulated by the cycloheximide treatment of seedlings. However, the effect of EIN3 overexpression on the EDF mRNA levels was less explicit. While EDF1 accumulated to higher levels in the Col:35S-EIN3 transgenic lines than in the wild-type plants, no significant change was observed in the expression of EDF3. Interestingly, EDF2 and EDF4 transcripts in transgenic lines actually showed a significant reduction in expression, perhaps due to a negative feedback regulation.

Isolation and Characterization of the T-DNA Knockout Mutants in the EDF Genes

T-DNA knockout mutant collections from various sources are a useful resource for studying a gene of interest. Our research utilized such mutant collections to further understand the role of EDF proteins in ethylyene pathways. Our laboratory previously identified a null mutant in the EDF1 (ANS136) gene from the Ken Feldmann's T-DNA collection (edf1-1). Additionally, a new large T-DNA collection was recently generated to study null mutants. A PCR-based approach was employed to screen for the insertions in all four EDF genes. The plant DNAs used for screening were pooled according to a four-dimentional matrix which allows for the mutant line identification in one round of PCRs, followed by Southern blotting. The total of nine new mutants were obtained, four of which harbor insertions approximately 1 kb downstream of the stop codon and, thus, were not characterized any further. The remaining mutations are in the 5' end of EDF1 (edf1-2, JM16613), EDF2 (edf2-2, JM8017), EDF3 (edf3-1, JM19227) and EDF4 (edf4-1, JM6742), and one mutant has a T-DNA insertion in the middle of the EDF2 open reading frame (edf2-1, JM2444). Locations of the T-DNA insertions in the EDF1, EDF2, EDF3, and EDF4 genes are shown in FIG. 2. Homozygous plants for each of the insertions were identified by PCR. Northern blot analysis revealed that all of the promoter mutants, but edf1-2, had close to undetectable levels of the corresponding mRNA. The leaky mutant edf1-2, that harbors a T-DNA insertion 789 bp upstream of the ATG, is still capable of making the EDF1 mRNA but accumulates it to a significantly lower level than the wild-type plants. Finally, the edf2-1 mutant could still make a transcript of a similar to wild-type size, but hybridization with the full-length versus 3'-end-specific probe showed that the transcript lacked the B3 domain, which is consistent with the position of the T-DNA insertion between the AP2 and B3 domains.

Extensive phenotypic analysis of the six edf mutants was carried out in a number of different hormonal assays, but failed to determine any abnormalities, implying that the EDF genes possess redundant functions. To overcome the redundancy problem, crosses were performed between the mutants in different EDF genes to construct double, triple and quadruple mutant combinations. Mutant genotypes were assayed by PCR. Interestingly, no phenotype was obtained in the double and triple mutants. However, the etiolated seedlings of the quadruple mutants showed weak, yet significant, insensitivity to ethylene, both in the root and in the hypocotyl. Importantly, the observed ethylene insensitivity was more dramatic in the quadruple mutant combinations that involved the strong edf1-1 allele (i.e. edf1-1 edf2-1 edf3-1 edf4-1 and edf1-1 edf2-2 edf3-1 edf4-1), compared to those that included the edf1-2 allele (edf1-2 edf2-1 edf3-1 edf4-1 and edf1-2 edf2-2 edf3-1 edf4-1). The weaker phenotype of the latter quadruple mutant combinations is consistent with the leaky expression of EDF1 in the edf1-2 mutant. Quantification of the seedlings response to ethylene (FIG. 3) revealed that, when grown in the presence of 10 uM ACC for 5 days, the edf1-1 edf2-1 edf-1 edf-4-1 mutant displays a less than 7-fold root length inhibition, compared to 12- and 9.5-fold inhibition observed in WS and Columbia, respectively.

Figure 3:
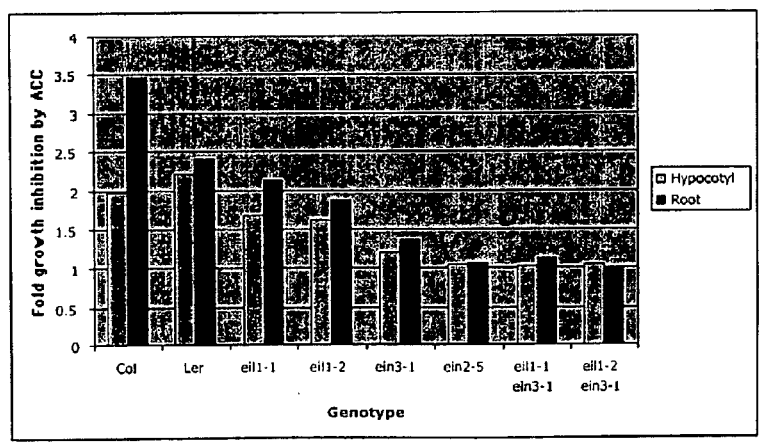
FIG. 3 shows ethylene insensitivity of the edf1-1 edf2-1 edf3-1 edf4-1 quadruple mutant. Phenotypes of 5-day-old etiolated seedlings grown on AT plates in the absence or presence of 10 uM ACC. Data are presented in tabular (A) and graph (B) forms. Ethylene response of 5-day-old etiolated seedlings of WS, Col and two independent quadruple mutant isolates was quantified. Root and hypocotyl lengths of seedlings grown on AT plates versus AT plus 10 uM ACC were measured. Each data point represents the average organ length of 50 or more seedlings plus/minus standard deviation. Fold inhibition was calculated as the ratio of the average organ length in air to that in ACC.

FIG. 3 shows ethylene insensitivity of the edf1-1 edf2-1 edf3-1 edf4-1 quadruple mutant. Phenotypes of 5-day-old etiolated seedlings grown on AT plates in the absence or presence of 10 uM ACC. Data are presented in tabular (A) and graph (B) forms. Ethylene response of 5-day-old etiolated seedlings of WS, Col and two independent quadruple mutant isolates was quantified. Root and hypocotyl lengths of seedlings grown on AT plates versus AT plus 10 uM ACC were measured. Each data point represents the average organ length of 50 or more seedlings plus/minus standard deviation. Fold inhibition was calculated as the ratio of the average organ length in air to that in ACC. Similar, yet less dramatic, differences were detected when the hypocotyls of the quadruple and wild-type seedlings were measured.

We also addressed the roles of the EDF genes in adult plants by introducing the ctr1-1 mutation into the quadruple mutant background edf1-1 edf2-1 edf3-1 edf4-1. The ctr1-1 mutation mimics constitutive exposure of plants to the ethylene gas (Kieber et al., 1993). Therefore by analyzing the phenotypes of the resulting adult quintuple mutant plants we were able to test the role of the EDF genes in ethylene signaling at later stages of development. The adult plants of the single mutant ctr1-1 possess very small rosettes with highly epinastic leaves. The dwarfism and the leaf epinasty were, however, significantly reduced in the quintuple mutant, indicating that the quadruple edf mutant combination is capable of partially suppressing the constitutive ethylene signaling initiated by ctr1-1. Similar effect was observed in the quintuple mutant seedlings that possessed longer roots and hypocotyls and reduced apical hook curvature, compared to that of ctr1-1. These results are consistent with the downstream position of the EDF genes in the ethylene signal transduction and provide very strong evidence that EDFs function as the positive regulators of the pathway. The insensitivity of the quadruple edf mutant seedlings to ethylene and the ability of this mutant combination to suppress both seedling and adult phenotypes of ctr1 suggest that the products of the EDF genes are required for the normal ethylene response throughout plant development.

Molecular Mechanisms of EDF Genes Action

The next question we asked is what molecular changes underlie the morphological defects of the edf-knockout and EDF-overexpression mutants. To address this issue, we employed the Affymetrix™ genechip technology. The advantage of this system is that expression of a large number of genes can be assayed simultaneously (cDNAs of over 8000 genes are represented on each *Arabidopsis* oligonucleotide array). Furthermore, unlike their alternative, i.e. the cDNA chips, the oligonucleotide arrays show greater reproducibility (Harmer et al., 2000), thus minimizing the number of artifacts.

Total RNAs were extracted from 3-week-old soil-grown adult plants (Col, quadruple mutant edf1-1 edf2-1 edf3-1 edf4-1, Col:35S-EDF1, and Col:35S-EDF2) that were subjected to 4-hour treatment with 10 ppm ethylene or hydrocarbon-free air. Biotin-labeled cRNAs were prepared and hybridized to the Affimetrix *Arabidopsis* oligonucleotide arrays. Expression analysis was performed using Genespring software. Data were normalized for each individual chip and for each gene between the experiments (double normalization).

The first analysis was to determine how many genes are differentially expressed between ethylene-treated and control (i.e. air-treated) wild-type plants. A two-fold or greater induction/repression by ethylene [reproducibly seen in two or more experiments] was used as a cutoff. Applying these criteria to the double-normalized data, 146 and 192 genes were classified as ethylene-inducible (red) and repressible (blue), respectively (Table 1). Importantly, several genes that have been previously shown to be up-regulated by ethylene, HLS1 (At4g37580) (Lehman et al., 1996), ERS1 (At2g40940), ERS2 (At1g04310), ETR2 (At3g23150) (Hua et al., 1998), ERF1 (At3g23240) (Solano et al., 1998), AtERF1 (16063_s_at), AtERF2 (At5g47220), and AtERF5 (At5g47230) (Fujimoto et al., 2000), fell in the list of ethylene-inducible genes, suggesting the system is working well in our hands. To assess which molecular processes are affected by exogenous ethylene application, we sorted the 338 differentially expressed clones into functional categories using MIPS and Genbank annotations and BLAST similarity searches to assign predicted functions to the hypothetical genes (Table 1). Not surprisingly, ethylene-regulated genes fell into several diverse functional categories, ranging from metabolism to transcription to cell growth, suggesting that ethylene treatment influences many physiological processes in the plant.

The role of ethylene in mediating plant responses to pathogens and abiotic stress is widely acknowledged and the molecular nature of plant defense is now beginning to be understood (Stepanova and Ecker 2000). Not surprisingly, in the chip experiments, a large number of pathogen-related and stress-inducible genes showed ethylene-regulated patterns of expression: mRNA levels of 20 and 17 genes were enhanced and repressed by the gas, respectively. Conversely, the molecular mechanisms of ethylene-mediated regulation of other physiological processes, such as growth and metabolism, remain a complete mystery. Looking at the expression profiles of 8000 genes (roughly one third of the entire *Arabidopsis* genome), one can attempt to uncover the mode of the ethylene gas action.

Experimental Details

Plant Strains and Growth Conditions

*Arabidopsis thaliana* accession Columbia-0 was used for all overexpression studies. The ein2-5, ein3-1, hls1-1, ctr1-1, eir1, axr1-12 and aux1-7 mutants are also in the Columbia-0 background. *Arabidopsis* seedlings were sterilized with 50% bleach solution supplemented with four drops of TritonX-100 per liter, rinsed three times with water, and plated using 0.7% LMP agarose on the surface of AT plates (4.3 g MS salts, 10 g sucrose, pH 6.0 with 1M KOH, 8 g bactoagar per liter). After 3–4 days in the light at 4 degrees C., the plates were wrapped in foil and kept in a 24 C incubator, after which the phenotypes of seedlings were analyzed. For growing plants in soil (Metromix-200), seeds were resuspended in water in eppendorf tubes, kept at 4 C for 3–4 days, and then sown onto soil surface using pipettman and water. Plants were grown under 16 hour light/8 hour dark cycle and watered as needed.

Ethylene treatment of *Arabidopsis* seedlings and adults grown in plates and soil, respectively, was performed in air-tight containers by flowing through hydrocarbon-free air supplemented with 10 parts per million ethylene. Cycloheximide treatment was performed in etiolated seedlings germinated for three days on a disc of Whatman paper resting on the surface of AT plates. Seedlings were transferred to a new plate by lifting the paper discs and pretreated for two hours with the indicated concentrations of cycloheximide in 0.5×MS. Then excess of the cycloheximide-containing solution was discarded and ethylene was applied for 3 hours. For auxin, methyl-jasmonate and ABA treatments, four-week old adult plants were sprayed with the indicated concentrations of the hormone and kept in trays covered with domes for the indicated periods of time.

*Arabidopsis* transformation was done by vacuum infiltration of 5–6 week-old plants into the *Agrobacterium* cultures resuspended in 5% sucrose, 0.5×MS, 0.044 uM benzylamino purine, 0.02% Silvet-77 solution. Selection of T1 transformants was performed on the AT medium supplemented with an appropriate antibiotic (kanamycin at 100 ug/ml or hygromycin B at 20 ug/ml).

Northern Blot Analysis

Tissues were frozen in liquid nitrogen, ground with mortar and pestle or directly in the eppendorf tubes using 0.5 mm or 1 mm glass beads and a Capmix capsule mixer. RNA extractions were performed in the eppendorf tubes using protocol of Reuber and Ausubel (Reuber and Ausubel, 1996) with slight modifications. Aurintricarboxylic acid (triammonium salt) was added to the grinding buffer at 1 mg/ml. For 500–700 ul of starting tissue powder a typical yield of 40–90 ug of total RNA was obtained. 20–30 ug of RNA was combined with 3 volumes of the denaturing mix (500 ul formamide, 170 ul 37% formaldehyde, 100 ul 10×MOPS buffer, 5 ul EtBr), heat-denatured for 10 min at 65 C, cooled on ice and loaded onto a 1.2% agarose 1×MOPS 2.2% formaldehyde gel. After electrophoresis, RNA was transferred to the Hybond-N+ membrane (Amersham) in 10×SSPE and the filters were air-dried and baked at 80–90 C for 2 hours. Probe labeling was performed using P32 and Megaprime DNA labeling kit (Amersham). Prehybridization and hybridization were done at 65 C overnight in Church & Gilbert solution (70 ml 10% SDS, 30 ml 1M potassium phosphate buffer pH7, 200 ul 0.5M EDTA pH8)). After extensive washing at 65 C (2 times 30 minutes each in 1% SSPE 0.5% SDS, followed by 2 times 30 minutes each in 0.1% SSPE 0.5% SDS) filters were exposed to a Phospholinager screen overnight.

Protein Expression Systems and Electrophoretic Mobility Shift Assay

The ANS136 (EDF1), ANS124 (EDF2), ANS133, ANS128 and ERF1 proteins were expressed in the in vitro transcription/translation system. The respective mRNAs were synthesized off the T3 promoter of pBsk(−) using T3 RNA polymerase. Flexi-rabbit reticulocyte lysate system (Promega) was used to translate the RNA molecules into the respective proteins, as directed by the manufacturer. Protein quality was assured by autoradiogram depicting incorporation of the S35-methionine into the newly made protein. The GCC-box-containing DNA fragments used in the EMSA with the above five proteins were obtained by annealing and Klenow-extension of the overlapping oligonucleotides Hook1 GAGAATTCGCAGACATAGCCGC-CATTTTCAACTTCTCACTC (SEQ ID NO: 2)+Hook3 GGATCCGAGTGAGAAGTTGAA (SEQ ID NO: 4) to generate the wild-type GCC-box, and Hook2 GAGAAT-TCGCAGACATATGATGAATTTTCAACTTCTCACTC (SEQ ID NO: 3)+Hook3 to generate its mutant version.

Full-length EDF1 and EDF2 were also expressed in the *E. coli* strain DH5a as GST-fusions in the pGEX-KG vector. Protein production was induced for 4 hours with 0.5 mM IPTG and monitored by coomassie blue staining. The 46 bp long '6-1' RBS DNA element (Kagaya et al., 1999) and its mutant version used for binding and EMSA with EDF1 and EDF2 were obtained by annealing and Klenow-extension of two overlapping oligonucleotide pairs: RAV6-1(F) AAT-TCTGGCAACAATAAACACCTGACT-CAGCGTTGGTTGG (SEQ ID NO: 5)+RAV6-1(R) AGCT-TACCAACCAACGCTGAG (SEQ ID NO: 6); RAV6-1 (mF) AATTCTGGGAAGAATAAACACGTCACT-CAGCGTTGGTTGG (SEQ ID NO: 7)+RAV6-1(R).

EIN3, along with its control protein, was expressed in the insect cell line SF9 of *Spodoptera frugiperda* infected with the BaculoGold DNA and a baculovirus vector pAcSG His NT (PharMingen) harboring the full-length EIN3 (or control) cDNA. Infected cells were harvested 3 days past inoculation with the amplified recombinant virus stock.

Wild-type and mutant versions of the EBS used in the mutant scan experiment were obtained by Klenow-filling of the following overlapping oligonucleotides: 5-2/3-FWT AGCCTCATGATCAAAGGGGGGATGCACT (SEQ ID NO: 8)+5-2/3-RWT TTAAATAGTGCATCCCCCCTTTG (SEQ ID NO: 9); 5-2/3-FM1 AGCCTCTACTA-CAAAGGGGGGATGCACT (SEQ ID NO: 10)+5-2/3-RWT; 5-2/3-FM2 AGCCTCATGATGTTTCGGGGGATG-CACT (SEQ ID NO: 11)+5-2/3-RM2 TTAAATAGTGCATCCCCCGAAAC (SEQ ID NO: 12); 5-2/3-FM3 AGCCTCATGATCAAAGCCCGGATGCACT (SEQ ID NO: 13)+5-2/3-RM3 TTAAATAGTGCATC-CGGGCTTTG (SEQ ID NO: 14); 5-2/3-FM4 AGCCTCAT-GATCAAAGGGGCCTTGCACT (SEQ ID NO: 15)+5-2/3-RM4 TTAAATAGTGCAAGGCCCCTTTG (SEQ ID NO: 16); 5-2/3-FM5 AGCCTCATGATCAAAGGGGGGAAC-GACT (SEQ ID NO: 17)+5-2/3-RM5 TTAAATAGTCGT-TCCCCCCTTTG (SEQ ID NO: 18); 5-2/3-FM6 AGCCT-CATGATCAAAGGGGGGATGCTGA (SEQ ID NO: 19)+5-2/3-RM6 TTAAATTCAGCATCCCCCCTTTG (SEQ ID NO: 20); 5-2/3-FWT+5-2/3-RM7 AATTTAAGTGCATC-CCCCCTTTG (SEQ ID NO: 21).

P32-labeling of promoter fragments and EMSA were performed as described (Solano et al., 1997; Solano et al., 1995). Prior to loading the reactions onto the acrylamide gel, the protein/DNA mixes were incubated on ice for 30 minutes. After electrophoresis, gels were dried and exposed to a Phosphohnager screen overnight.

Generation and b-Glucoronidase Activity of the 5×EBS-GUS Reporter Lines

The minimal $(-46)_{35}S$ CMV promoter fragment was amplified by PCR from the 35S(-90)GUS-pUC18 vector (gift from J. Paz-Ares) and subcloned into pBsk(-). The 32 bp-long synthetic EBS fragment of the EDF1 promoter (-906 to -875), or its mutant version as depicted in M3, was multimerized in the above (-46)35S-pBsk plasmid using BamHI/BglII strategy. The 240 bp-long BamHI/HindIII fragment that contained 5 copies of the wild-type or mutant EBS followed by the (-46)35S minimal promoter was excised and subcloned into the pCambia-1381z vector upstream of the GUS open reading frame. The resulting constructs were introduced into the Agrobacterium strain C58 and transformed into plants by vacuum infiltration.

GUS staining of the resulting T1 and T2 transformants was performed at 37 C overnight in 100 mM potassium phosphate buffer (pH7) supplemented with 0.5 mM K4Fe(CN)6, 0.5 mM K3Fe(CN)6, 10 mM EDTA, 0.5% Triton-X100 and 0.5 mg/ml X-gluc.

Plant Overexpression Constructs; T-DNA Mutagenesis and Genotyping

To generate transgenic plants for overexpression/antisense studies, a partial cDNA clone ANS136 (i.e. truncated EDF1 that lacked the first 8 bp of the open reading frame), full-length cDNAs ANS133, ANS128, EDF1, and EDF2 were subcloned into pROK2 vector ( ) under the control of the 35S CMV promoter in sense/antisense orientation, respectively, and transformed into plants by Agrobacterium-mediated transformation.

To identify knockouts in the ANS133 and EDF genes, three T-DNA collections were screened by PCR: 6000 lines of K Feldmann in the WS background (ABRC), 6000 lines of T. Jack in the Col-6 background (ABRC), and the initial 30 000 lines of J. Alonso, W. Crosby and J. Ecker in the Col-0 background (unpublished). PCR amplification (40× [94 C—30 sec, 56 C—30 sec, 72 C—3 min], 4 C) was performed in the MJ Research-200 thermocyclers in 96-well plates. Plants homozygous for the insertions were identified by PCR-based genotyping using the above stated conditions and the following primer combinations:

dreb2a-1 (WS): RBKF GCTCATGATCAGAT-TGTCGTTTCCCGCCTT (SEQ ID NO: 22)+133(1) TTTC-CCTCGGTCTGATGCGTCTGAGG (SEQ ID NO: 23); 133(3) CCACATCATTGGGCCAACC (SEQ ID NO: 24)+133(1).

dreb2a-2 (WS): LBKF GATGCAATCGATATCAGC-CAATTTTAGAC (SEQ ID NO: 25)+133(2) CGGCTC-CACTCCACCGGAGAAGGG (SEQ ID NO: 26); 133(4) CTCTGCTCGAAGCTAAGCCACCC (SEQ ID NO: 27)+133(2).

dreb2a-3 (Col-6): TJ113-LB GAACATCGGTCTCAAT-GCA (SEQ ID NO: 28)+133(2); 133(4)+133(2).

edf1-1 (WS): RBKF+136(2) CGCCTTTCGTCG-GAGACGGATTCATCCCC (SEQ ID NO: 29); 136p(8) CTCCTCTGCACCTCTTCTCC (SEQ ID NO: 30)+136(2).

edf1-2 (Col-0): LBJM1 GGCAATCAGCTGTTGC-CCGTCTCACTGGTG (SEQ ID NO: 31)+136(6) ATAT-TACGTGTAACATGCGTC (SEQ ID NO: 32); 5-2/3-3F AACAAAAGGTCCAAATCTCATGTG (SEQ ID NO: 33)+136(6).

edf2-1 (Col-0): LBJM1+124(2) CTGCCGCTCTAGTC-CGGTCGATCTCTCG (SEQ ID NO: 34); 124-RI5' ACGC-CGAATTCGGATGGGAAGCGGCGGG (SEQ ID NO: 35)+124(2).

edf2-2 (Col-0): LBJM1+124p(11) AATGGAAAGG-TAGGGTCAACGC (SEQ ID NO: 36); 124p(6) GTATGT-TCAGATATAGATCGACAG (SEQ ID NO: 37)+124p(11).

edf3-1 (Col-0): RBJM2 TGATAGTGACCTTAGGC-GACTTTTGAACGC (SEQ ID NO: 38)+K13N2p(4) CTCGTCTACGCTACTCATGGCATCC (SEQ ID NO: 39); K13N2p(3) CTTTATCTTTTGCATGAACCTTCC (SEQ ID NO: 40)+K13N2p(4).

edf4-1 (Col-0): LBJM1+RAV1p(5) CTCATCAACGC-TACTCGATTCC (SEQ ID NO: 41); RAVlp(4) CCATTC-CATGGCCCACACATGGGTCC (SEQ ID NO: 42)+RAV1p(5).

Double, triple, quadruple and quintuple mutants of the EDF genes were constructed by sequential crossing of single, double and triple mutants. For genotyping F2 progenies, genomic DNA from individual plants was extracted by the CTAB method (Doyle and Doyle, 1987), and the PCR analysis was performed as described above.

Microarray Analysis

RNA preparation, synthesis, biotin labeling and fragmentation of the cRNA, GeneChip microarray (Affymetrix) hybridization, scanning and normalization of the intensity values was done as described (Harmer et al., 2001). Data analysis was carried out using GeneSpring 4.0 software (World Wide Web.sigenetics.com). The average difference intensities for each gene were loaded in this software. Normalization between experiments was performed using the following criteria: the median of the intensities of all the elements in a particular chip was adjusted to 1 and the median of the measurements of a particular gene in all the experiments was also adjusted to 1. Genes that were induced or repressed by ethylene two or more fold in Col-0 plants were selected using GeneSpring Gene Finder. Only those genes that showed consistent pattern of expression in at least one additional experiment were further considered. Clustering of specific subsets of genes was performed using GeneSpring Clustering (standard Correlation procedure, Separation Ratio of 0.5 and Minimum Distance of 0.001). Genome sequence and the initial gene annotations were obtained from MIPS website (World Wide Web.mips.biochem.mpg.de) (Jan. 18th 2001 version). Further functional information for each selected gene was obtained by BLAST search of the predicted protein sequence (World Wide Web.ncbi.nlm.nih.gov) against the NR database. Regulatory sequences in the promoters (2000 bp. Upstream of the predicted ATG) of the genes were searched using GeneSpring software. For the identification of potential cis-elements in the ethylene-regulated genes a probability cut0off of 0.05 was used.

Screening of Compounds which Modulate Ethylene Sensitivity

Embodiments of the invention provide methods for screening compounds which modulate ethylene sensitivity. Structural or functional analogs of biologically active polypeptides of interest or of small molecules with which they interact (e.g., agonists, antagonists, null compounds) are evaluated in order to ascertain their role in the modulation of ethylene sensitivity.

Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573).

The use of molecular modeling as a tool for small molecule screening and combinatorial chemistry has dramatically increased due to the advent of computer graphics. Not only is it possible to view molecules on computer screens in three dimensions but it is also possible to examine the interactions of macromolecules such as enzymes and receptors and rationally designed derivative molecules to test. (See Boorman, Chem. Eng. News 70:18–26 (1992). A vast amount of user-friendly software and hardware is now available and virtually all pharmaceutical companies have computer modeling groups devoted to rational drug design. Molecular Simulations Inc. (World Wide Web.msi.com), for example, sells several sophisticated programs that allow a user to start from an amino acid sequence, build a two or three-dimensional model of the protein or polypeptide, compare it to other two or three-dimensional models, and analyze the interactions of compounds, drugs, and peptides with a three dimensional model in real time. Accordingly, in some embodiments of the invention, software is used to compare regions of ethylene genes and molecules that interact with ethylene genes (collectively referred to as "binding partners"—e.g., anti-EDF antibodies, G proteins, and Gβγ subunits), and fragments or derivatives of these molecules with other molecules, such as peptides, peptidomimetics, and chemicals, so that therapeutic interactions can be predicted and designed. (See Schneider, *Genetic Engineering News* December: page 20 (1998), Tempczyk et al., *Molecule Simulations Inc. Solutions* April (1997) and Butenhof, *Molecular Simulations Inc. Case Notes* (August 1998) *for a discussion of molecular modeling*).

For example, the protein sequence of an EDF or binding partner, or domains of these molecules (or nucleic acid sequence encoding these polypeptides or both), can be entered onto a computer readable medium for recording and manipulation. It will be appreciated by those skilled in the art that a computer readable medium having these sequences can interface with software that converts or manipulates the sequences to obtain structural and functional information, such as protein models. That is, the functionality of a software program that converts or manipulates these sequences includes the ability to compare these sequences to other sequences or structures of molecules that are present on publicly and commercially available databases so as to conduct rational drug design.

The EDF or binding partner polypeptide or nucleic acid sequence or both can be stored, recorded, and manipulated on any medium that can be read and accessed by a computer. As used herein, the words "recorded" and "stored" refer to a process for storing information on computer readable medium. A skilled artisan can readily adopt any of the presently known methods for recording information on a computer readable medium to generate manufactures comprising the nucleotide or polypeptide sequence information of this embodiment. A variety of data storage structures are available to a skilled artisan for creating a computer readable medium having recorded thereon a nucleotide or polypeptide sequence. The choice of the data storage structure will generally be based on the component chosen to access the stored information. Computer readable media include magnetically readable media, optically readable media, or electronically readable media. For example, the computer readable media can be a hard disc, a floppy disc, a magnetic tape, zip disk, CD-ROM, DVD-ROM, RAM, or ROM as well as other types of other media known to those skilled in the art. The computer readable media on which the sequence information is stored can be in a personal computer, a network, a server or other computer systems known to those skilled in the art.

Embodiments of the invention utilize computer-based systems that contain the sequence information described herein and convert this information into other types of usable information (e.g., protein models for rational drug design). The term "a computer-based system" refers to the hardware, software, and any database used to analyze an EDF or a binding partner nucleic acid or polypeptide sequence or both, or fragments of these biomolecules so as to construct models or to conduct screening of small molecules which modulate ethylene sensitivity. The computer-based system preferably includes the storage media described above, and a processor for accessing and manipulating the sequence data. The hardware of the computer-based systems of this embodiment comprise a central processing unit (CPU) and a database. A skilled artisan can readily appreciate that any one of the currently available computer-based systems are suitable.

In one particular embodiment, the computer system includes a processor connected to a bus that is connected to a main memory (preferably implemented as RAM) and a variety of secondary storage devices, such as a hard drive and removable medium storage device. The removable medium storage device can represent, for example, a floppy disk drive, a DVD drive, an optical disk drive, a compact disk drive, a magnetic tape drive, etc. A removable storage medium, such as a floppy disk, a compact disk, a magnetic tape, etc. containing control logic and/or data recorded therein can be inserted into the removable storage device. The computer system includes appropriate software for reading the control logic and/or the data from the removable medium storage device once inserted in the removable medium storage device. The EDF or binding partner nucleic acid or polypeptide sequence or both can be stored in a well known manner in the main memory, any of the secondary storage devices, and/or a removable storage medium. Software for accessing and processing these sequences (such as search tools, compare tools, and modeling tools etc.) reside in main memory during execution.

As used herein, "a database" refers to memory that can store an EDF or binding partner nucleotide or polypeptide sequence information, protein model information, information on other peptides, chemicals, peptidomimetics, and other agents that interact with EDF proteins, and values or results from functional assays. Additionally, a "database" refers to a memory access component that can access manufactures having recorded thereon EDF or binding partner nucleotide or polypeptide sequence information, protein model information, information on other peptides, chemicals, peptidomimetics, and other agents that interact with EDFs, and values or results from functional assays. In other embodiments, a database stores an "EDF functional profile" comprising the values and results (e.g., ability to modulate ethylene sensitivity) from one or more "EDF functional assays", as described herein or known in the art, and relationships between these values or results. The sequence data and values or results from EDF functional assays can be stored and manipulated in a variety of data processor programs in a variety of formats. For example, the sequence data can be stored as text in a word processing file, such as Microsoft WORD or WORDPERFECT, an ASCII file, a html file, or a pdf file in a variety of database programs familiar to those of skill in the art, such as DB2, SYBASE, or ORACLE.

A "search program" refers to one or more programs that are implemented on the computer-based system to compare an EDF or binding partner nucleotide or polypeptide sequence with other nucleotide or polypeptide sequences and agents including but not limited to peptides, peptidomimetics, and chemicals stored within a database. A search program also refers to one or more programs that compare one or more protein models to several protein models that exist in a database and one or more protein models to several peptides, peptidomimetics, and chemicals that exist in a database. A search program is used, for example, to compare one EDF functional profile to one or more EDF functional profiles that are present in a database. Still further, a search program can be used to compare values or results from EDF functional assays and agents that modulate EDF-mediated signal transduction.

A "retrieval program" refers to one or more programs that can be implemented on the computer-based system to identify a homologous nucleic acid sequence, a homologous protein sequence, or a homologous protein model. A retrieval program can also used to identify peptides, peptidomimetics, and chemicals that interact with an EDF protein sequence, or an EDF protein model stored in a database. Further, a retrieval program is used to identify a specific agent that modulates EDF-mediated signal transduction to a desired set of values, results, or profile. That is, a retrieval program can also be used to obtain "a binding partner profile" that is composed of a chemical structure, nucleic acid sequence, or polypeptide sequence or model of an agent that interacts with an EDF and, thereby modulates (inhibits or enhances) ethylene sensitivity. Further, a binding partner profile can have one or more symbols that represent these molecules and/or models, an identifier that represents one or more agents including, but not limited to peptides and peptidomimetics (referred to collectively as "peptide agents") and chemicals, and a value or result from a functional assay.

As a starting point to screening molecules which modulate ethylene sensitivity, a two or three dimensional model of a polypeptide of interest is created (e.g., EDF-1, EDF-2, or a binding partner, such as a Gβγ subunit or an antibody). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, $4^{th}$ Edition, Prentice-Hall, N.J. (1972)).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052). Conventional homology modeling techniques have been used routinely to build models of proteases and antibodies. (Sowdhamini et al., *Protein Engineering* 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON that constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and organised to energy minimization using the molecular modeling package QUANTA. (See e.g., Aszódi et al., Proteins:Structure, Function, and Genetics, Supplement 1:38–42 (1997)).

In a preferred approach, the commercially available "Insight II 98" program (Molecular Simulations Inc.) and accompanying modules are used to create a two and/or three dimensional model of a polypeptide of interest from an amino acid sequence. Insight II is a three-dimensional graphics program that can interface with several modules that perform numerous structural analysis and enable real-time rational drug design and combinatorial chemistry. Modules such as Builder, Biopolymer, Consensus, and Converter, for example, allow one to rapidly create a two dimensional or three dimensional model of a polypeptide, carbohydrate, nucleic acid, chemical or combinations of the foregoing from their sequence or structure. The modeling tools associated with Insight II support many different data file formats including Brookhaven and Cambridge databases; AMPAC/MOPAC and QCPE programs; Molecular Design Limited Molfile and SD files, Sybel Mol2 files, VRML, and Pict files.

Additionally, the techniques described above can be supplemented with techniques in molecular biology to design models of the protein of interest. For example, a polypeptide of interest can be analyzed by an alanine scan (Wells, Methods in Enzymol. 202:390–411 (1991)) or other types of site-directed mutagenesis analysis. In alanine scan, each amino acid residue of the polypeptide of interest is sequentially replaced by alanine in a step-wise fashion (i.e., only one alanine point mutation is incorporated per molecule starting at position #1 and proceeding through the entire molecule), and the effect of the mutation on the peptide's activity in a functional assay is determined. Each of the amino acid residues of the peptide is analyzed in this manner and the regions important for the modulation of signal transduction or membrane association, for example, are identified. These functionally important regions can be recorded on a computer readable medium, stored in a database in a computer system, and a search program can be employed to generate a protein model of the functionally important regions.

Once a model of the polypeptide of interest is created, it can be compared to other models so as to identify new members of the EDF family and binding partners. By starting with the amino acid sequence or protein model of EDF-1 or EDF-2 or a binding partner, for example, molecules having two-dimensional and/or three-dimensional homology can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{[\text{Length of the longer sequence within the matched span} + \text{number of gaps introduced into the longer sequence in order to align the two sequences}]} \times 100$$

Accordingly, the protein sequence corresponding to an EDF or a binding partner or a fragment or derivative of these molecules can be compared to known sequences on a protein basis. Protein sequences corresponding to an EDF, or a binding partner or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences are compared to publicly known amino acid sequences of Swissprot using BLASTX with the parameter E=0.001. The molecules identified as members of the family of EDFs or candidate binding partners desirably have at least 35% homology and preferably have 40%, 45%, 50% or 55% or greater homology to EDF-1 or EDF-2 The EDF family members and candidate binding partners that interact with an EDF can have the following degrees of homology to evt-1 or evt-2 or both, for example: 35%, 36%, 37%, 38%, 39%,40%,41%,42%,43%,44%,45%, 46%,47%,48%,49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%,79%, 80%, 81%, 82%, 83%, 84%, 85%, 86%, 87%, 88%, 89%, 90%, 91%, 92%, 93%, 94%, 95%, 96%, 97%, 98%, and 99%. The EDF family members and candidate binding partners having greater than or equal to 35% homology are identified and are subsequently examined using an EDF functional assay.

In another embodiment, computer modeling and the sequence-to-structure-to-function paradigm is exploited to identify more members of the EDF family candidate binding partners. By this approach, first the structure of an EDF (e.g., EDF-1 or EDF-2) or a candidate binding partner (e.g., Gβγ subunit or antibody) having a known response in a characterization assay is determined from its sequence using a threading algorithm, which aligns the sequence to the best matching structure in a structural database. Next, the protein's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998).

The FFFs are built by iteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained. The ability to search three-dimensional structure databases for structural similarity to a protein of interest can also be accomplished by employing the Insight II using modules such as Biopolymer, Binding Site Analysis, and Profiles-3D.

By using this computational protocol, genome sequence data bases such as maintained by various organizations including: World Wide Web.tigr.org/tdb; World Wide Web.zenetics.wisc.edu; World Wide Web.genome-www-.stanford.edu/~ball; World Wide Web.hiv-web.lanl.gov; World Wide Web.ncbi.nlm.nih.gov; World Wide Web.ebi-.ac.uk; pasteur.fr/other/biology; and World Wide Web-.genome.wi.mit.edu, can be rapidly screened for specific protein active sites and for identification of the residues at those active sites that resemble a desired molecule. Several other groups have developed databases of short sequence patterns or motifs designed to identify a given function or activity of a protein. Many of these databases, notably Prosite (World Wide Web.expasy.hcuge.ch/sprot/prosite-.html); Blocks (World Wide Web.blocks.fhcrc.org); Prints (World Wide Web.biochem.ucl.ac.uk/bsm/dbbrowser/ PRINTS/PRINTS.html), the Molecular Modelling Database (MMDB), and the Protein Bank can use short stretches of sequence information to identify sequence patterns that are specific for a given function; thus they avoid the problems arising from necessity of matching entire sequences.

By a similar approach, a candidate binding partner can be identified and manufactured as follows. First, a molecular model of one or more molecules that are known to interact with an EDF or portions of these molecules that interact with an EDF are created using one of the techniques discussed above or as known in the art. Next, chemical libraries and databases are searched for molecules similar in structure to the known molecule. That is, a search can be made of a three dimensional data base for non-peptide (organic) structures (e.g., non-peptide analogs, and/or dipeptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., *Acta Crystallogr.*, B35: 2331–2339 (1979). The identified candidate binding partners that interact with EDFs can then be analyzed in a functional assay (e.g., evaluating the role of the identified candidate on ethylene sensitivity) and new molecules can be modeled after the candidate binding partners that produce a desirable response. By cycling in this fashion, libraries of molecules that interact with EDFs and produce a desirable or optimal response in a functional assay can be selected.

It is noted that search algorithms for three dimensional data base comparisons are available in the literature. See, e.g., Cooper, et al., *J. Comput.-Aided Mol. Design*, 3: 253–259 (1989) and references cited therein; Brent, et al., *J. Comput.-Aided Mol. Design*, 2: 311–310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the receptor substrate interactions.

By another approach, protein models of binding partners that interact with an EDF (e.g., a Gβγ subunit or antibody) can be made by the methods described above and these models can be used to predict the interaction of new molecules. Once a model of a binding partner is identified, the active sites or regions of interaction can be identified. Such active sites might typically be ligand binding sites. The active site can be identified using methods known in the art including, for example, from the amino acid sequences of peptides, from the nucleotide sequences of nucleic acids, or from study of complexes of the EDF gene with a ligand, such as Gβγ or specific G proteins. In the latter case, chemical or X-ray crystallographic methods can be used to find the active site by finding where on the EDF the complexed ligand is found (e.g. PHD or PHD and protein—protein module). Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

If an incomplete or insufficiently accurate structure is determined, the methods of computer based numerical modeling can be used to complete the structure or improve its accuracy. Any recognized modeling method can be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site of the known binding partner, either experimentally, by modeling, or by a combination, candidate binding partners can be identified by searching databases containing compounds along with information on their molecular structure. Such a search seeks compounds having structures that match the determined active site structure and that interact with the groups defining the active site. Such a search can be manual, but is preferably computer assisted. One program that allows for such analysis is Insight II having the Ludi module. Further, the Ludi/ACD module allows a user access to over 65,000 commercially available drug candidates (MDL's Available Chemicals Directory) and provides the ability to screen these compounds for interactions with the protein of interest.

Alternatively, these methods can be used to identify improved binding partners from an already known binding partner. The composition of the known binding partner can be modified and the structural effects of modification can be determined using the experimental and computer modeling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity.

A number of articles review computer modeling of drugs interactive with specific-proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific for the modulation of EDF-mediated signal transduction, membrane association, vesicle trafficking and other EDF functions.

Many more computer programs and databases can be used with embodiments of the invention to identify new members of the EDF family and binding partners that modulate EDF function. The following list is intended not to limit the invention but to provide guidance to programs and databases that are useful with the approaches discussed above. The programs and databases that can be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990), herein incorporated by reference), FASTA (Pearson and Lipman, *Proc. Natl. Acad. Sci. USA*, 85: 2444 (1988), herein incorporated by reference), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), Biopendium (lnpharmatica), SBdBase (Structural Bioinformatics), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Once candidate binding partners have been identified, desirably, they are analyzed in a functional assay. Further cycles of modeling and functional assays can be employed to more narrowly define the parameters needed in a binding partner. Each binding partner and its response in a functional assay can be recorded on a computer readable media and a database or library of binding partners and respective responses in a functional assay can be generated. These databases or libraries can be used by researchers to identify important differences between active and inactive molecules so that compound libraries are enriched for binding partners that have favorable characteristics. The section below describes several EDF functional assays that can be used to characterize new EDF family members and candidate binding partners.

Ethylene Characterization Assays

The term "ethylene characterization assay" or "ethylene functional assay" or "functional assay" the results of which can be recorded as a value in a "ethylene functional profile", include assays that directly or indirectly evaluate the presence of an EDF nucleic acid or protein in a cell and the ability of an EDF to associate with a membrane, interact with another molecule, and/or modulate ethylene sensitivity.

Some functional assays involve binding assays that utilize multimeric agents. One form of multimeric agent concerns a manufacture comprising an EDF, hybrid, binding partner, or fragment thereof disposed on a support. These multimeric agents provide the EDF, hybrid, binding partner, or fragment thereof in such a form or in such a way that a sufficient affinity is achieved. A multimeric agent having an EDF, hybrid, or binding partner or fragment thereof is obtained by joining the desired polypeptide to a macromolecular support. A "support" can be a termed a carrier, a protein, a resin, a cell membrane, or any macromolecular structure used to join or immobilize such molecules. Solid supports include, but are not limited to, the walls of wells of a reaction tray, test tubes, polystyrene beads, magnetic beads, nitrocellulose strips, membranes, microparticles such as latex particles, animal cells, Duracyte®, artificial cells, and others. An EDF, hybrid, or binding partner or fragment thereof can also be joined to inorganic carriers, such as silicon oxide material (e.g., silica gel, zeolite, diatomaceous earth or aminated glass) by, for example, a covalent linkage through a hydroxy, carboxy or amino group and a reactive group on the carrier.

In several multimeric agents, the macromolecular support has a hydrophobic surface that interacts with a portion of the EDF, hybrid, or binding partner or fragment thereof by a hydrophobic non-covalent interaction. In some cases, the hydrophobic surface of the support is a polymer such as plastic or any other polymer in which hydrophobic groups have been linked such as polystyrene, polyethylene or polyvinyl. Additionally, an EDF, hybrid, or binding partner or fragment thereof can be covalently bound to carriers including proteins and oligo/polysaccharides (e.g. cellulose, starch, glycogen, chitosane or aminated sepharose). In these later multimeric agents, a reactive group on the molecule, such as a hydroxy or an amino group, is used to join to a reactive group on the carrier so as to create the covalent bond. Additional multimeric agents comprise a support that has other reactive groups that are chemically activated so as to attach the EDF, hybrid, or binding partner or fragment thereof. For example, cyanogen bromide activated matrices, epoxy activated matrices, thio and thiopropyl gels, nitrophenyl chloroformate and N-hydroxy succinimide chlorformate linkages, or oxirane acrylic supports are used. (Sigma).

Furthermore, in some embodiments, a liposome or lipid bilayer (natural or synthetic) is contemplated as a support and EDFs, hybrids, or binding partners are attached to the membrane surface or are incorporated into the membrane by techniques in liposome engineering. By one approach, liposome multimeric supports comprise an EDF, hybrid, or binding partner that is exposed on the surface. A hydrophobic domain can be joined to the EDF, hybrid, or binding partner so as to facilitate the interaction with the membrane. Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorb® (Johns-Manville Products, Denver Co.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042–1045 (1995)). For some embodiments, a "naked" carrier (i.e., lacking an attached binding partner) that has the capacity to attach an EDF or binding partner in the body of a organism is administered. By this approach, a "prodrug-type" therapy is envisioned in which the naked carrier is administered separately from the EDF or binding partner and, once both are in the body of the organism, the carrier and the EDF or binding partner are assembled into a multimeric complex.

The insertion of linkers, such as linkers (e.g., "λ linkers" engineered to resemble the flexible regions of λ phage) of an appropriate length between the EDF, hybrid, or binding partner and the support are also contemplated so as to encourage greater flexibility of the EDF, hybrid, or binding partner and thereby overcome any steric hindrance that can be presented by the support. The determination of an appropriate length of linker that allows for an optimal cellular response or lack thereof, can be determined by screening the EDFs, hybrids, or binding partners with varying linkers in the assays detailed in the present disclosure.

A composite support comprising more than one type of EDF, hybrid, or binding partner is also envisioned. A "composite support" can be a carrier, a resin, or any macromolecular structure used to attach or immobilize two or more different binding partners or EDFs. In some embodiments, a liposome or lipid bilayer (natural or synthetic) is contemplated for use in constructing a composite support and EDFs or binding partners are attached to the membrane surface or are incorporated into the membrane using techniques in liposome engineering.

As above, the insertion of linkers, such as λ linkers, of an appropriate length between the EDF or binding partner and the support is also contemplated so as to encourage greater flexibility in the molecule and thereby overcome any steric hindrance that can occur. The determination of an appropriate length of linker that allows for an optimal cellular response or lack thereof, can be determined by screening the EDFs or binding partners with varying linkers in the assays detailed in the present disclosure.

In other embodiments of the invention, the multimeric and composite supports discussed above can have attached multimerized EDFs, hybrids, or binding partners so as to create a "multimerized-multimeric support" and a "multimerized-composite support", respectively. A multimerized ligand can, for example, be obtained by coupling two or more binding partners in tandem using conventional techniques in molecular biology. The multimerized form of the EDF, hybrid, or binding partner can be advantageous for many applications because of the ability to obtain an agent with a higher affinity for an EDF, for example. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized binding partner or EDF or hybrid and the support can encourage greater flexibility and limit steric hindrance presented by the support. The determination of an appropriate length of linker can be determined by screening the EDFs, hybrids, and binding partners with varying linkers in the assays detailed in this disclosure.

Thus, several approaches to identify agents that interact with an EDF, employ an EDF or a fragment thereof joined to a support. Once the support-bound EDF is obtained, for example, candidate binding partners are contacted to the support-bound EDF and an association is determined directly (e.g., by using labeled binding partner) or indirectly (e.g., by using a labeled antibody directed to the binding partner). Candidate binding partners are identified as binding partners by virtue of the association with the support-bound EDF. The properties of the binding partners are analyzed and derivatives are made using rational drug design and combinatorial chemistry. Candidate binding partners can be obtained from random chemical or peptide libraries but, preferably, are rationally selected. For example, monoclonal antibodies that bind to an EDF can be created and the nucleic acids encoding the VH and VL domains of the antibodies can be sequenced. These sequences can then be used to synthesize peptides that bind to the EDF. Further, peptidomimetics corresponding to these sequences can be created. These molecules can then be used as candidate binding partners.

Additionally, a cell based approach can be used characterize new EDF family members or EDF hybrids or to rapidly identify binding partners that interact with an EDF and, thereby, modulate signal transduction. Preferably, molecules identified in the support-bound EDF assay described above are used in the cell based approach, however, randomly generated compounds can also be used.

The assays described above can also be performed in the presence and absence of candidate binding partners, preferably binding partners identified by a support-bound assay. Other EDF characterization assays take advantage of techniques in molecular biology that are employed to discover protein:protein interactions. One method that detects protein—protein interactions in vivo, the two-hybrid system, is described in detail for illustration only and not by way of limitation. Other similar assays that can be can be adapted to identify binding partners include:

1) the two-hybrid systems (Field & Song, *Nature* 340: 245–246 (1989); Chien et al., *Proc. Natl. Acad. Sci. USA* 88:9578–9582 (1991); and Young KH, *Biol. Reprod.* 58:302–311 (1998), all references herein expressly incorporated by reference);
2) reverse two-hybrid system (Leanna & Hannink, *Nucl. Acid Res.* 24:3341–3347 (1996), herein incorporated by reference);
3) repressed transactivator system (Sadowski et al., U.S. Pat. No. 5,885,779), herein incorporated by reference);
4) phage display (Lowman H B, *Annu. Rev. Biophys. Biomol. Struct.* 26:401–424 (1997), herein incorporated by reference); and
5) GST/HIS pull down assays, mutant operators (Granger et al., WO 98/01879) and the like (See also Mathis G., *Clin. Chem.* 41:139–147 (1995); Lam K. S. *Anticancer Drug Res.,* 12:145–167 (1997); and Phizicky et al., *Microbiol Rev.* 59:94–123 (1995), all references herein expressly incorporated by reference).

An adaptation of the system described by Chien et al., 1991, Proc. Natl. Acad. Sci. USA, 88:9578–9582, herein incorporated by reference), which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding an EDF or fragment thereof, and the other plasmid consists of nucleotides encoding the transcription activator protein's activation domain fused to a cDNA encoding an unknown protein that has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology can be used to screen activation domain libraries for proteins that interact with the "bait" gene product. By way of example, and not by way of limitation, EDFs can be used as the bait gene product. Total genomic or cDNA sequences are fused to the DNA encoding an activation domain. This library and a plasmid encoding a hybrid of a bait gene encoding the EDF product (EDF-1) fused to the DNA-binding domain are cotransformed into a yeast reporter strain, and the resulting transformants are screened for those that express the reporter gene. For example, and not by way of limitation, a bait gene sequence encoding an EDF can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait EDF are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait EDF gene-GAL4 fusion plasmid into a yeast strain which contains a lacZ gene driven by a promoter which contains GAL4 activation sequence. A cDNA encoded protein, fused to GAL4 transcriptional activation domain, that interacts with bait EDF gene product will reconstitute an active GAL4 protein and thereby drive expression of the lacZ gene. Colonies that express lacZ can be detected and the cDNA can then be purified from these strains, and used to produce and isolate the binding partner by techniques routinely practiced in the art.

While the described embodiment represents various preferred embodiment, it is to be understood that modifications will occur to those skilled in the art without departing from the spirit of the invention. The scope of the invention is therefore to be determined solely by the appended claims.

LITERATURE CITED

1. Abel, S., Nguyen, M., and Theologis, A. (1995a). The PS-IAA4/5 family of early auxin-inducible messenger-RNAs in *Arabidopsis thaliana*, J Mol Biol 251, 533–549.
2. Abel, S., Nguyen, M. D., Chow, W., and Theologis, A. (1995b). ACS4, a primary indoleacetic acid-responsive gene encoding 1-aminocyclopropane-1-carboxylate synthase in *Arabidopsis thaliana*. Structural characterization, expression in *Escherichia coli*, and expression characteristics in response to auxin [corrected] [published erratum appears in J Biol Chem 1995 Oct. 27;270(43):26020], J Biol Chem 270, 19093–9.
3. Abeles, F., Morgan, P., and Saltveit, M. (1992). Ethylene in Plant Biology, Vol 2 (San Diego, Calif., Academic Press).
4. Alonso, J. M., Hirayama, T., Roman, G., Nourizadeh, S., and Ecker, J. R. (1999). EIN2, a bifunctional transducer of ethylene and stress responses in *Arabidopsis*, Science 284, 2148–52.
5. Arteca, J. M., and Arteca, R. N. (1999). A multi-responsive gene encoding 1-aminocyclopropane-1-carboxylate synthase (ACS6) in mature *Arabidopsis* leaves, Plant Mol Biol 39, 209–19.
6. Banga, M., Slaa, E. J., Blom, C. W. P. M., and Voesenek, L. A. C. J. (1996). Ethylene biosynthesis and accumulation under drained and submerged conditions, Plant Physiol 112, 229–237.
7. Baulcombe, D., Saunders, G., Bevan, M., Mayo, M., and Harrison, B. (1986). Expression of biologically active viral satellite RNA from nuclear genome of transformed plants, Nature 321, 446–449.
8. Bennett, M., Marchant, A., Green, H., May, S., Ward, S., Millner, P., Walker, A., Schulz, B., and Feldmann, K. (1996). *Arabidopsis* AUX1 gene: a permease-like regulator of root gravitropism, Science 273, 948–950.
9. Bleecker, A., Estelle, M., Somerville, C., and Kende, H. (1988). Insensitivity to ethylene conferred by a dominant mutation in *Arabidopsis thaliana*, Science 241, 1086–1089.
10. Brett, C. T. (2000). Cellulose microfibrils in plants: biosynthesis, deposition, and integration into the cell wall, Int Rev Cytol 199, 161–99.
11. Buttner, M., and Singh, K. (1997). *Arabidopsis thaliana* ethylene-responsive element binding protein (AtEBP), an ethylene-inducible, GCC box DNA-binding protein interacts with an ocs element binding protein, Proc Natl Acad Sci USA 94, 5961–5966.
12. Capitani, G., Hohenester, E., Feng, L., Storici, P., Kirsch, J. F., and Jansonius, J. N. (1999). Structure of 1-aminocyclopropane-1-carboxylate synthase, a key enzyme in the biosynthesis of the plant hormone ethylene, J Mol Biol 294, 745–56.
13. Chang, C., Kwok, S. F., Bleecker, A. B., and Meyerowitz, E. M. (1993). *Arabidopsis* ethylene-response gene ETR1: similarity of product to two-component regulators, Science 262, 539–544.
14. Chang, C., and Shockey, J. A. (1999). The ethylene-response pathway: signal perception to gene regulation, Curr Opin Plant Biol 2, 352–8.
15. Chao, Q., Rothenberg, M., Solano, R., Roman, G., Terzaghi, W., and Ecker, J. (1997). Activation of the ethylene gas response pathway in *Arabidopsis* by the nuclear protein ETHYLENE-INSENSITIVE3 and related proteins, Cell 89, 1133–1144.
16. Chen, R., Hilson, P., Sedbrook, J., Rosen, E., Caspar, T., and Masson, P. H. (1998). The *arabidopsis thaliana* AGRAVITROPIC 1 gene encodes a component of the polar-auxin-transport efflux carrier, Proc Natl Acad Sci USA 95, 15112–7.
17. Ciardi, J. A., Tieman, D. M., Lund, S. T., Jones, J. B., Stall, R. E., and Klee, H. J. (2000). Response to *Xanthomonas campestris* pv. *vesicatoria* in tomato involves regulation of ethylene receptor gene expression, Plant Physiol 123, 81–92.
18. Clark, K. L., Larsen, P. B., Wang, X., and Chang, C. (1998). Association of the *Arabidopsis* CTR1 Raf-like kinase with the ETR1 and ERS ethylene receptors [published erratum appears in Proc Natl Acad Sci USA 1998 Jul. 21;95(15):9060], Proceedings of the National Academy of Sciences of the United States of America 95, 5401–6.
19. Cosgrove, D. J. (2000). Loosening of plant cell walls by expansins, Nature 407, 321–6.
20. D'Agostino, I. B., Deruere, J., and Kieber, J. J. (2000). Characterization of the response of the *Arabidopsis* response regulator gene family to cytokinin, Plant Physiol 124, 1706–17.
21. del Pozo, J. C., Timpte, C., Tan, S., Callis, J., and Estelle, M. (1998). The ubiquitin-related protein RUB1 and auxin response in *Arabidopsis*., Science 280, 1760–1763.
22. Dong, H., Delaney, T. P., Bauer, D. W., and Beer, S. V. (1999). Harpin induces disease resistance in *Arabidopsis* through the systemic acquired resistance pathway mediated by salicylic acid and the NIM1 gene, Plant J 20, 207–15.
23. Doyle, J. J., and Doyle, J. L. (1987). A rapid DNA isolation procedure for small quantities of fresh leaf tissue, Phytochem Bull 19, 11–15.
24. Durfee, T., Becherer, K., Chen, P.-L., Yeh, S.-H., Yang, Y., Kilburn, A. E., Lee, W.-H., and Elledge, S. J. (1993). The retinoblastoma protein associates with the protein phosphatase type 1 catalytic subunit, Genes Dev 7, 555–569.
25. Falke, J. J., Bass, R. B., Butler, S. L., Chervitz, S. A., and Danielson, M. A. (1997). The two-component signaling pathway of bacterial chemotaxis: a molecular view of signal transduction by receptors, kinases, and adaptation ezymes, Annu Rev Cell Dev Biol 13, 457–512.
26. Fiedler, U., and Weiss, V. (1995). A common switch in activation of the response regulators NtrC and PhoB: phosphorylation induces dimerization of the receiver modules, Embo J 14, 3696–705.
27. Fujimoto, S. Y., Ohta, M., Usui, A., Shinshi, H., and Ohme-Takagi, M. (2000). *Arabidopsis* ethylene-responsive element binding factors act as transcriptional activators or repressors of GCC box-mediated gene expression, Plant Cell 12, 393–404.
28. Gamble, R. L., Coonfield, M. L., and Schaller, G. E. (1998). Histidine kinase activity of the ETR1 ethylene receptor from *Arabidopsis*, Proceedings of the National Academy of Sciences of the United States of America 95, 7825–9.
29. Gietz, D., Stjean, A., Woods, R. A., and Schiestl, R. H. (1992). Improve method for high-efficiency transformation of yeast cells, Nucleic Acids Res 20, 1425.
30. Giraudat, J., Hauge, B. M., Valon, C., Smalle, J., Parcy, F., and Goodman, H. M. (1992). Isolation of the *Arabidopsis* ABI3 gene by positional cloning, Plant Cell 4, 1251–61.
31. Gosti, F., Bertauche, N., Vartanian, N., and Giraudat, J. (1995). Abscisic acid-dependent and -independent regulation of gene expression by progressive drought in *Arabidopsis thaliana*, Mol Gen Genet 246, 10–18.
32. Grantz, A. A., Muller-Dieckmann, H. J., and Kim, S. H. (1998). Subcloning, crystallization and preliminary X-ray analysis of the signal receiver domain of ETR1, an ethylene receptor from *Arabidopsis thaliana*, Acta Crystallogr D Biol Crystallogr 54, 690–2.
33. Gu, Y. Q., Yang, C., Thara, V. K., Zhou, J., and Martin, G. B. (2000). Pti4 is induced by ethylene and salicylic acid, and its product is phosphorylated by the Pto kinase 12, 771–785.
34. Guilfoyle, T. J., Ulmasov, T., and Hagen, G. (1998). The ARF family of transcription factors and their role in plant hormone-responsive transcription, Cell Mol Life Sci 54, 619–27.
35. Guzman, P., and Ecker, J. (1990). Exploiting the triple response of *Arabidopsis* to identify ethylene-related mutants, Plant Cell 2, 513–523.
36. Hadfield, K. A., and Bennett, A. B. (1998). Polygalacturonases: many genes in search of a function, Plant Physiol 117, 337–43.
37. Hall, A. E., Chen, Q. G., Findell, J. L., Schaller, G. E., and Bleecker, A. B. (1999). The relationship between ethylene binding and dominant insensitivity conferred by mutant forms of the ETR1 ethylene receptor, Plant Physiol 121, 291–300.
38. Hall, A. E., Findell, J. L., Schaller, G. E., Sisler, E. C., and Bleecker, A. B. (2000). Ethylene perception by the ERS1 protein in *Arabidopsis*, Plant Physiol 123, 1449–58.
39. Hardtke, C. S., and Berleth, T. (1998). The *Arabidopsis* gene MONOPTEROS encodes a transcription factor mediating embryo axis formation and vascular development, Embo J 17, 1405–411.
40. Harmer, S. L., Hogenesch, J. B., Straume, M., Chang, H. S., Han, B., Zhu, T., Wang, X., Kreps, J. A., and Kay, S. A. (2000). Orchestrated transcription of key pathways in *Arabidopsis* by the circadian clock, Science 290, 2110–3.
41. Harper, R. M., Stowe-Evans, E. L., Luesse, D. R., Muto, H., Tatematsu, K., Watahiki, M. K., Yamamoto, K., and Liscum, E. (2000). The NPH4 locus encodes the auxin response factor ARF7, a conditional regulator of differential growth in aerial *Arabidopsis* tissue, Plant Cell 12, 757–70.
42. Heredia, A., Jimenez, A., and Guillen, R. (1995). Composition of plant cell walls, Z Lebensm Unters Forsch 200, 24–31.
43. Hirayama, T., Kieber, J. J., Hirayama, N., Kogan, M., Guzman, P., Nourizadeh, S., Alonso, J. M., Dailey, W. P., Dancis, A., and Ecker, J. R. (1999). RESPONSIVE-TO-ANTAGONIST1, a Menkes/Wilson disease-related copper transporter, is required for ethylene signaling in *Arabidopsis*, Cell 97, 383–93.
44. Hua, J., Chang, C., Sun, Q., and Meyerowitz, E. M. (1995). Ethylene insensitivity conferred by *Arabidopsis* ERS gene, Science 269, 1712–4.
45. Hua, J., and Meyerowitz, E. M. (1998). Ethylene responses are negatively regulated by a receptor gene family in, Cell 94, 261–71.
46. Hua, J., Sakai, H., Nourizadeh, S., Chen, Q. H. G., Bleecker, A. B., Ecker, J. R., and Meyerowitz, E. M. (1998). EIN4 and ERS2 are members of the putative ethylene receptor gene family in *Arabidopsis*, The Plant Cell 10, 1321–1332.
47. Imamura, A., Hanaki, N., Nakamura, A., Suzuki, T., Taniguchi, M., Kiba, T., Ueguchi, C., Sugiyama, T., and Mizuno, T. (1999). Compilation and characterization of *Arabidopsis thaliana* response regulators implicated in His-Asp phosphorelay signal transduction, Plant Cell Physiol 40, 733–42.
48. Johnson, P. R., and Ecker, J. R. (1998). The ethylene gas signal transduction pathway: a molecular perspective, Annu Rev Genet 32, 227–54.
49. Kachroo, P., Yoshioka, K., Shah, J., Dooner, H. K., and Klessig, D. F. (2000). Resistance to turnip crinkle virus in *Arabidopsis* is regulated by two host genes and is salicylic acid dependent but NPR1, ethylene, and jasmonate independent, Plant Cell 12, 677–90.
50. Kagaya, Y., Ohmiya, K., and Hattori, T. (1999). RAV1, a novel DNA-binding protein, binds to bipartite recognition sequence through two distinct DNA-binding domains uniquely found in higher plants, Nucleic Acids Res 27, 470–8.
51. Kende, H. (1993). Ethylene biosynthesis, Annu Rev Plant Physiol Plant Mol Biol 44, 283–307.
52. Kieber, J. J., Rothenberg, M., Roman, G., Feldmann, K. A., and Ecker, J. R. (1993). CTR1, a negative regulator of the ethylene response pathway in *Arabidopsis*, encodes a member of the raf family of protein kinases, Cell 72, 427–441.
53. Kim, H., Ralph, J., Yahiaoui, N., Pean, M., and Boudet, A. M. (2000). Cross-coupling of hydroxycinnamyl aldehydes into lignins, Org Lett 2, 2197–200.
54. Kim, J., Harter, K., and Theologis, A. (1997). Protein-protein interactions among the Aux/IAA proteins, Proc Natl Acad Sci USA 94, 11786–11791.
55. Kiyosue, T., Beetham, J. K., Pinot, F., Hammock, B. D., Yamaguchi-Shinozaki, K., and Shinozaki, K. (1994). Characterization of an *Arabidopsis* cDNA for a soluble epoxide hydrolase gene that is inducible by auxin and water stress., Plant J 6, 259–69.
56. Knoester, M., Pieterse, C. M., Bol, J. F., and Van Loon, L. C. (1999). Systemic resistance in *Arabidopsis* induced by rhizobacteria requires ethylene-dependent signaling at the site of application, Mol Plant Microbe Interact 12, 720–7.
57. Knox, J. P. (1995). The extracellular matrix in higher plants. 4. Developmentally regulated proteoglycans and glycoproteins of the plant cell surface, Faseb J 9, 1004–12.
58. Kosugi, S., and Ohashi, Y. (2000). Cloning and DNA-binding properties of a tobacco Ethylene-Insensitive3 (EIN3) homolog, Nucleic Acids Res 28, 960–7.
59. Krasko, A., Schroder, H. C., Perovic, S., Steffen, R., Kruse, M., Reichert, W., Muller, I. M., and Muller, W. E. (1999). Ethylene modulates gene expression in cells of the marine sponge Suberites domuncula and reduces the degree of apoptosis, J Biol Chem 274, 31524–30.

60. Lehman, A., Black, R., and Ecker, J. (1996). HOOKLESS1, an ethylene response gene, is required for differential cell elongation in the *Arabidopsis* hypocotyl, Cell 85, 183–194.
61. Leyser, H. M., Lincoln, C. A., Timpte, C., Lammer, D., Turner, J., and Estelle, M. (1993). *Arabidopsis* auxin-resistance gene AXR1 encodes a protein related to ubiquitin-activating enzyme E1, Nature 364, 161–4.
62. Li, Y., Hagen, G., and Guilfoyle, T. J. (1991). An auxin-responsive promoter is differentially induced by auxin gradients during tropisms, Plant Cell 3, 1167–1175.
63. Lincoln, C., Britton, J., and Estelle, M. (1990). Growth and development of the axr1 mutants in *Arabidopsis*, Plant Cell 2, 1071–1080.
64. Liu, Q., Kasuga, M., Sakuma, Y., Abe, H., Miura, S., Yamaguchi-Shinozaki, K., and Shinozaki, K. (1998). Two transcription factors, DREB1 and DREB2, with an EREBP/AP2 DNA binding domain separate two cellular signal transduction pathways in drought- and low-temperature-responsive gene expression, respectively, in *Arabidopsis*, Plant Cell 10, 1391–406.
65. Luerssen, H., Kirik, V., Herrmann, P., and Misera, S. (1998). FUSCA3 encodes a protein with a conserved VP1/AB13-like B3 domain which is of functional importance for the regulation of seed maturation in *Arabidopsis thaliana*, Plant J 15, 755–64.
66. Luschnig, C., Gaxiola, R. A., Grisafi, P., and Fink, G. R. (1998). EIR1, a root-specific protein involved in auxin transport, is required for gravitropism in *Arabidopsis thaliana*, Genes Dev 12, 2175–87.
67. Makino, S., Kiba, T., Imamura, A., Hanaki, N., Nakamura, A., Suzuki, T., Taniguchi, M., Ueguchi, C., Sugiyama, T., and Mizuno, T. (2000). Genes encoding pseudo-response regulators: insight into His-to-Asp phosphorelay and circadian rhythm in *Arabidopsis thaliana*, Plant Cell Physiol 41, 791–803.
68. Marchant, A., Kargul, J., May, S. T., Muller, P., Delbarre, A., Perrot-Rechenmann, C., and Bennett, M. J. (1999). AUX1 regulates root gravitropism in *Arabidopsis* by facilitating auxin uptake within root apical tissues, Embo J 18, 2066–73.
69. Mehta, P. K., and Christen, P. (1994). Homology of 1-aminocyclopropane-1-carboxylate synthase, 8-amino-7-oxononanoate synthase, 2-amino-6-caprolactam racemase, 2,2-dialkylglycine decarboxylase, glutamate-1-semialdehyde 2,1-aminomutase and isopenicillin-N-epimerase with aminotransferases, Biochem Biophys Res Commun 198, 138–43.
70. Menke, F. L., Champion, A., Kijne, J. W., and Memelink, J. (1998). A novel jasmonate- and elicitor-responsive element in the periwinkle secondary metabolite biosynthetic gene Str interacts with a jasmonate- and elicitor-inducible AP2-domain transcription factor, ORCA2., Embo J 18, 4455–4463.
71. Morgan P W, D. M. (1997). Ethylene and plant responses to stress, Physiologia Plantarum 100, 620–630.
72. Muller, A., Guan, C., Galweiler, L., Tanzler, P., Huijser, P., Marchant, A., Parry, G., Bennett, M., Wisman, E., and Palme, K. (1998). AtPIN2 defines a locus of *Arabidopsis* for root gravitropism control, Embo J 17, 6903–11.
73. Muller-Dieckmann, H. J., Grantz, A. A., and Kim, S. H. (1999). The structure of the signal receiver domain of the *Arabidopsis thaliana* ethylene receptor ETR1, Structure Fold Des 7, 1547–56.
74. Nakashima, K., Shinwari, Z. K., Sakuma, Y., Seki, M., Miura, S., Shinozaki, K., and Yamaguchi-Shinozaki, K. (2000). Organization and expression of two *Arabidopsis* DREB2 genes encoding DRE-binding proteins involved in dehydration- and high-salinity-responsive gene expression, Plant Mol Biol 42, 657–65.
75. Nishitani, K. (1997). The role of endoxyloglucan transferase in the organization of plant cell walls, Int Rev Cytol 173, 157–206.
76. Norman-Setterblad, C., Vidal, S., and Palva, E. T. (2000). Interacting signal pathways control defense gene expression in *Arabidopsis* in response to cell wall-degrading enzymes from *Erwinia* carotovora, Mol Plant Microbe Interact 13, 430–8.
77. Ohme-Takagi, M., and Shinshi, H. (1995). Ethylene-inducible DNA binding proteins that interact with an ethylene-responsive element, Plant Cell 7, 173–182.
78. Ohtsubo, N., Mitsuhara, I., Koga, M., Seo, S., and Ohashi, Y. (1999). Ethylene promotes the necrotic lesion formation and basic PR gene expression in TMV-infected tobacco, Plant Cell Physiol 40, 808–817.
79. Okamuro, J., Caster, B., Villarroel, R., Montagu, M. V., and Jofuku, K. (1997). The AP2 domain of APETALA2 defines a large new family of DNA binding proteins in *Arabidopsis*, Procl Natl Acad Sci USA 94, 7076–7081.
80. Perrin, R. M., DeRocher, A. E., Bar-Peled, M., Zeng, W., Norambuena, L., Orellana, A., Raikhel, N. V., and Keegstra, K. (1999). Xyloglucan fucosyltransferase, an enzyme involved in plant cell wall biosynthesis, Science 284, 1976–9.
81. Pickett, F., Wilson, A., and Estelle, M. (1990). The aux1 mutation of *Arabidopsis* confers both auxin and ethylene resistance, Plant Physiol 94, 1462–1466.
82. Pirrung, M. C. (1999). Histidine kinases and two-component signal transduction systems, Chem Biol 6, R167–75.
83. Reuber, T. L., and Ausubel, F. M. (1996). Isolation of *Arabidopsis* genes that differentiate between resistance responses mediated by the RPS2 and RPM1 disease resistance genes, Plant Cell 8, 241–9.
84. Riechmann, J. L., and Meyerowitz, E. M. (1998). The AP2/EREBP family of plant transcription factors, Philos Trans R Soc Lond B Biol Sci 353, 1405–12.
85. Rodriguez, F. I., Esch, J. J., Hall, A. E., Binder, B. M., Schaller, G. E., and Bleecker, A. B. (1999). A copper cofactor for the ethylene receptor ETR1 from *Arabidopsis*, Science 283, 996–8.
86. Roman, G., Lubarsky, B., Kieber, J., Rothenberg, M., and Ecker, J. (1995). Genetic analysis of ethylene signal transduction in *Arabidopsis thaliana*: five novel mutant loci integrated into a stress response pathway, Genetics 139, 1393–1409.
87. Ros Barcelo, A. (1997). Lignification in plant cell walls, Int Rev Cytol 176, 87–132.
88. Ruegger, M., Dewey, E., Gray, W. M., Hobbie, L., Turner, J., and Estelle, M. (1998). The TIR1 protein of *Arabidopsis* functions in auxin response and is related to human SKP2 and yeast grr1p, Genes Dev 12, 198–207.
89. Sakai, H., Hua, J., Chen, Q. G., Chang, C., Medrano, L. J., Bleecker, A. B., and Meyerowitz, E. M. (1998). ETR2 is an ETR1-like gene involved in ethylene signaling in *Arabidopsis*, Proc NatlAcad Sci USA 95, 5812–7.
90. Schaffner, A. R. (1998). Aquaporin function, structure, and expression: are there more surprises to surface in water relations?, Planta 204, 131–9.
91. Schaller, G., and Bleecker, A. (1995). Ethylene-binding sites generated in yeast expressing the *Arabidopsis* ETR1 gene, Science 270, 1809–1811.
92. Schaller, G. E., Ladd, A. N., Lanahan, M. B., Spanbauer, J. M., and Bleecker, A. B. (1995). The ethylene response mediator ETR1 from *Arabidopsis* forms a disulfide-linked dimer, J Biol Chem 270, 12526–12530.
93. Schumacher, K., and Chory, J. (2000). Brassinosteroid signal transduction: still casting the actors, Curr Opin Plant Biol 3, 79–84.
94. Solano, R., Fuertes, A., Sanchez-Pulido, L., Valencia, A., and Paz-Ares, J. (1997). A single residue substitution causes a switch from the dual DNA binding specificity of plant transcription factor MYB.Ph3 to the animal c-MYB specificity, J Biol Chem 272, 2889–95.
95. Solano, R., Nieto, C., Avila, J., Canas, L., Diaz, I., and Paz-Ares, J. (1995). Dual DNA binding specificity of a petal epidermis-specific MYB transcription factor (MYB.Ph3) from *Petunia hybrida*, EMBO J. 14, 1773–1784.
96. Solano, R., Stepanova, A., Chao, Q., and Ecker, J. R. (1998). Nuclear events in ethylene signaling: a transcriptional cascade mediated by ETHYLENE-INSENSITIVE3 and ETHYLENE-RESPONSE-FACTOR1, Genes & Development 12, 3703–14.
97. Stepanova, A. N., and Ecker, J. R. (2000). Ethylene Signaling: from mutants to molecules, Curr Opin Plant Biol 3, 353–360.
98. Suzuki, K., Suzuki, N., Ohme-Takagi, M., and Shinshi, H. (1998). Immediate early induction of mRNAs for ethylene-responsive transcription fators in tobaco leaf strips after cutting, Plant J 15, 657–665.
99. Suzuki, T., Sakurai, K., Imamura, A., Nakamura, A., Ueguchi, C., and Mizuno, T. (2000). Compilation and characterization of histidine-containing phosphotransmitters implicated in His-to-Asp phosphorelay in plants: AHP signal transducers of *Arabidopsis thaliana*, Biosci Biotechnol Biochem 64, 2486–9.
100. Tarun, A. S., Lee, J. S., and Theologis, A. (1998). Random mutagenesis of 1-aminocyclopropane-1-carboxylate synthase: a key enzyme in ethylene biosynthesis, Proc Natl Acad Sci USA 95, 9796–801.
101. Tarun, A. S., and Theologis, A. (1998). Complementation analysis of mutants of 1-aminocyclopropane-1-carboxylate synthase reveals the enzyme is a dimer with shared active sites, J Biol Chem 273, 12509–14.
102. Thomma, B. P., Eggemmont, K., Tierens, K. F., and Broekaert, W. F. (1999). Requirement of functional ethylene-insensitive 2 gene for efficient resistance of *Arabidopsis* to infection by *Botrytis cinerea*, Plant Physiol 121, 1093–102.
103. Tieman, D. M., Taylor, M. G., Ciardi, J. A., and Klee, H. J. (2000). The tomato ethylene receptors NR and LeETR4 are negative regulators of ethylene response and exhibit functional compensation within a multigene family, Proc Natl Acad Sci USA 97, 5663–8.
104. Timpte, C., Lincoln, C., Pickett, F., Turner, J., and Estelle, M. (1995). The AXR1 and AUX1 genes of *Arabidopsis* function in separate auxin-response pathways, Plant J 8, 561–569.
105. Tire, C., De Rycke, R., De Loose, M., Inze, D., Van Montagu, M., and Engler, G. (1994). Extensin gene expression is induced by mechanical stimuli leading to local cell wall strengthening in *Nicotiana* plumbaginifolia, Planta 195, 175–81.
106. Ulmasov, T., Murfett, J., Hagen, G., and Guilfoyle, T. J. (1997). Aux/IAA proteins repress expression of reporter genes containing natural and highly active synthetic auxin response elements, Plant Cell 9, 1963–71.
107. Urao, T., Miyata, S., Yamaguchi-Shinozaki, K., and Shinozaki, K. (2000). Possible His to Asp phosphorelay signaling in an *Arabidopsis* two-component system, FEBS Lett 478, 227–32.
108. Utsuno, K., Shikanai, T., Yamada, Y., and Hashimoto, T. (1998). Agr, an Agravitropic locus of *Arabidopsis thaliana*, encodes a novel membrane-protein family member, Plant Cell Physiol 39, 1111–8.
109. van der Kop, D. A., Schuyer, M., Scheres, B., van der Zaal, B. J., and Hooykaas, P. J. (1996). Isolation and characterization of an auxin-inducible glutathione S-transferase gene of *Arabidopsis thaliana*, Plant Mol Biol 30, 839–44.
110. Voesenek, L. A. C. J., Vriezen, W. H., Smekens, M. J. E., Huitink, F. H. M., Bogemann, G. M., and Blom, C. W. P. M. (1997). Ethylene sensitivity and response sensor expression in petioles of *Rumex* species at low $O_2$ and high $CO_2$ concentrations, Plant Physiol 114, 1501–1509.
111. Vogel, J. P., Woeste, K. E., Theologis, A., and Kieber, J. J. (1998). Recessive and dominant mutations in the ethylene biosynthetic gene ACS5 of *Arabidopsis* confer cytokinin insensitivity and ethylene overproduction, respectively, Proc Natl Acad Sci USA 95, 4766–71.
112. Vriezen, W. H., Hulzink, R., Mariani, C., and Voesenek, L. A. C. J. (1999). 1-Aminocyclopropane-1-caboxylate oxidase activity limits ethylene biosynthesis in *Rumex palustris* during submergence, Plant Physiol 121, 189–195.
113. Vriezen, W. H., vanrijn, C. P. E., Voesenek, L. A. C. J., and Mariani, C. (1997). A homolog of the *Arabidopsis thaliana* ERS gene is actively regulated in *Rumex palustris* upon flooding, The Plant J 11, 1265–1271.
114. Welch, M., Chinardet, N., Mourey, L., Birck, C., and Samama, J. P. (1998). Structure of the CheY-binding domain of histidine kinase CheA in complex with CheY, Nat Struct Biol 5, 25–9.
115. Welin, B. V., Olson, A., and Palva, E. T. (1995). Structure and organization of two closely related low-temperature-induced dhn/lea/rab-like genes in *Arabidopsis thaliana* L. Heynh, Plant Mol Biol 29, 391–395.
116. Whetten, R. W., MacKay, J. J., and Sederoff, R. R. (1998). Recent advances in understanding lignin biosynthesis, Annu Rev Plant Physiol Plant Mol Biol 49, 585–609.
117. Wingler, A., Fritzius, T., Wiemken, A., Boller, T., and Aeschbacher, R. A. (2000). Trehalose induces the ADP-glucose pyrophosphorylase gene, ApL3, and starch synthesis in *Arabidopsis*, Plant Physiol 124, 105–14.
118. Wisman, E., Hartmann, U., Sagasser, M., Baumann, E., Palme, K., Hahlbrock, K., Saedler, H., and Weisshaar, B. (1998). Knock-out mutants from an En-1 mutagenized *Arabidopsis thaliana* population generate phenylpropanoid biosynthesis phenotypes, Proc Natl Acad Sci USA 95, 12432–7.
119. Woeste, K. E., and Kieber, J. J. (2000). A strong loss-of-function mutation in RAN1 results in constitutive activation of the ethylene response pathway as well as a rosette-lethal phenotype, Plant Cell 12, 443–55.
120. Woeste, K. E., Ye, C., and Kieber, J. J. (1999). Two *Arabidopsis* mutants that overproduce ethylene are affected in the posttranscriptional regulation of 1-aminocyclopropane-1-carboxylic acid synthase, Plant Physiol 119, 521–30.
121. Wyatt, R. E., Ainley, W. M., Nagao, R. T., Conner, T. W., and Key, J. L. (1993). Expression of the *Arabidopsis* AtAux2-11 auxin-responsive gene in transgenic plants, Plant Mol Biol 22, 731–749.
122. Yang, S., and Hoffman, N. (1984). Ethylene biosynthesis and its regulation in higher plants, Annu Rev Plant Physiol 35, 155–189.
123. Yi, H. C., Joo, S., Nam, K. H., Lee, J. S., Kang, B. G., and Kim, W. T. (1999). Auxin and brassinosteroid differentially regulate the expression of three members of the 1-aminocyclopropane-1-carboxylate synthase gene family in mung bean (*Vigna radiata* L.), Plant Mol Biol 41, 443–54.

What is claimed is:

1. A mutant *Arabidopsis* or *Brassica* plant comprising one or more mutated forms of an *Arabidopsis* or *Brassica* edf gene selected from the group consisting of edf1, edf2, edf3 and edf4, wherein said *Arabidopsis* or *Brassica* plant exhibits a decreased response to ethylene.

2. The mutant plant of claim 1, further comprising a mutant form of an *Arabidopsis* or *Brassica* ctr1 gene.

3. The mutant plant of claim 1 wherein the edf1 gene is mutated.

4. The mutant plant of claim 1 wherein the edf2 gene is mutated.

5. The mutant plant of claim 1 wherein the edf3 gene is mutated.

6. The mutant plant of claim 1 wherein the edf4 gene is mutated.

7. The mutant plant of claim 1 wherein two or more of said edf1, edf2, edf3 and edf4 genes are mutated.

8. The mutant plant of claim 1 wherein three or more of said edf1, edf2, edf3 and edf4 genes are mutated.

9. The mutant plant of claim 1 wherein all of said edf1, edf2, edf3 and edf4 genes are mutated.

10. The mutant plant of claim 1 wherein the plant is mutated by the introduction of one or more heterologous nucleic acids into said plant.

11. The mutant plant of claim 1 wherein the plant is mutated by T-DNA insertion.

12. The mutant *Arabidopsis* or *Brassica* plant of claim 1 wherein said *Arabidopsis* or *Brassica* plant is selected from the group consisting of *Arabidopsis*, cabbage, broccoli, cauliflower and Brussels sprouts.

* * * * *

SEQUENCE LISTING

<160> NUMBER OF SEQ ID NOS: 71

<210> SEQ ID NO 1
<211> LENGTH: 12
<212> TYPE: DNA
<213> ORGANISM: Artificial Sequence
<220> FEATURE:
<223> OTHER INFORMATION: Cloning primer
<220> FEATURE:
<221> NAME/KEY: misc_feature
<222> LOCATION: 2, 7, 11
<223> OTHER INFORMATION: n = A,T,C or G

<400> SEQUENCE: 1 angggnatg na                                                              12

<210> SEQ ID NO 2
<211> LENGTH: 41
<212> TYPE: DNA
<213> ORGANISM: Artificial Sequence
<220> FEATURE:
<223> OTHER INFORMATION: Cloning primer

<400> SEQUENCE: 2
gagaattcgc agacatagcc gccatttcca acttctcact c                             41

<210> SEQ ID NO 3
<211> LENGTH: 41
<212> TYPE: DNA
<213> ORGANISM: Artificial Sequence
<220> FEATURE:
<223> OTHER INFORMATION: Cloning primer

<400> SEQUENCE: 3
gagaattcgc agacatatga tgaattttca acttctcact c                             41

<210> SEQ ID NO 4
<211> LENGTH: 21
<212> TYPE: DNA
<213> ORGANISM: Artificial Sequence
<220> FEATURE:
<223> OTHER INFORMATION: Cloning primer

<400> SEQUENCE: 4
ggatccgagt gagaagttga a                                                   21

<210> SEQ ID NO 5
<211> LENGTH: 40
<212> TYPE: DNA
<213> ORGANISM: Artificial Sequence
<220> FEATURE:
<223> OTHER INFORMATION: Cloning primer

<400> SEQUENCE: 5
aattctggca acaataaaca cctgactcag cgttggttgg                               40

<210> SEQ ID NO 6
<211> LENGTH: 21
<212> TYPE: DNA
<213> ORGANISM: Artificial Sequence
<220> FEATURE:
<223> OTHER INFORMATION: Cloning primer

<400> SEQUENCE: 6
agcttaccaa ccaacgctga g                                                   21

<210> SEQ ID NO 7
<211> LENGTH: 40
<212> TYPE: DNA
<213> ORGANISM: Artificial Sequence
<220> FEATURE:
<223> OTHER INFORMATION: Cloning primer

<400> SEQUENCE: 7
aattctggga agaataaaca cgtcactcag cgttggttgg                40

<210> SEQ ID NO 8
<211> LENGTH: 28
<212> TYPE: DNA
<213> ORGANISM: Artificial Sequence
<220> FEATURE:
<223> OTHER INFORMATION: Cloning primer

<400> SEQUENCE: 8
agcctcatga tcaaaggggg gatgcact                28

<210> SEQ ID NO 9
<211> LENGTH: 23
<212> TYPE: DNA
<213> ORGANISM: Artificial Sequence
<220> FEATURE:
<223> OTHER INFORMATION: Cloning primer

<400> SEQUENCE: 9
ttaaatagtg catcccccct ttg                23

<210> SEQ ID NO 10
<211> LENGTH: 28
<212> TYPE: DNA
<213> ORGANISM: Artificial Sequence
<220> FEATURE:
<223> OTHER INFORMATION: Cloning primer

<400> SEQUENCE: 10
agcctctact acaaaggggg gatgcact                28

<210> SEQ ID NO 11
<211> LENGTH: 28
<212> TYPE: DNA
<213> ORGANISM: Artificial Sequence
<220> FEATURE:
<223> OTHER INFORMATION: Cloning primer

<400> SEQUENCE: 11
agcctcatga tgtttcgggg gatgcact                28

<210> SEQ ID NO 12
<211> LENGTH: 23
<212> TYPE: DNA
<213> ORGANISM: Artificial Sequence
<220> FEATURE:
<223> OTHER INFORMATION: Cloning primer

<400> SEQUENCE: 12
ttaaatagtg catccccga aac                23

<210> SEQ ID NO 13
<211> LENGTH: 28
<212> TYPE: DNA
<213> ORGANISM: Artificial Sequence
<220> FEATURE:

```
<223> OTHER INFORMATION: Cloning primer

<400> SEQUENCE: 13
agcctcatga tcaaagcccg gatgcact                                28

<210> SEQ ID NO 14
<211> LENGTH: 23
<212> TYPE: DNA
<213> ORGANISM: Artificial Sequence
<220> FEATURE:
<223> OTHER INFORMATION: Cloning primer

<400> SEQUENCE: 14
ttaaatagtg catccgggct ttg                                     23

<210> SEQ ID NO 15
<211> LENGTH: 28
<212> TYPE: DNA
<213> ORGANISM: Artificial Sequence
<220> FEATURE:
<223> OTHER INFORMATION: Cloning primer

<400> SEQUENCE: 15
agcctcatga tcaaaggggc cttgcact                                28

<210> SEQ ID NO 16
<211> LENGTH: 23
<212> TYPE: DNA
<213> ORGANISM: Artificial Sequence
<220> FEATURE:
<223> OTHER INFORMATION: Cloning primer

<400> SEQUENCE: 16
ttaaatagtg caaggcccct ttg                                     23

<210> SEQ ID NO 17
<211> LENGTH: 28
<212> TYPE: DNA
<213> ORGANISM: Artificial Sequence
<220> FEATURE:
<223> OTHER INFORMATION: Cloning primer

<400> SEQUENCE: 17
agcctcatga tcaaagggggg gaacgact                               28

<210> SEQ ID NO 18
<211> LENGTH: 23
<212> TYPE: DNA
<213> ORGANISM: Artificial Sequence
<220> FEATURE:
<223> OTHER INFORMATION: Cloning primer

<400> SEQUENCE: 18
ttaaatagtc gttcccccct ttg                                     23

<210> SEQ ID NO 19
<211> LENGTH: 28
<212> TYPE: DNA
<213> ORGANISM: Artificial Sequence
<220> FEATURE:
<223> OTHER INFORMATION: Cloning primer

<400> SEQUENCE: 19
agcctcatga tcaaagggggg gatgctga                               28
```

<210> SEQ ID NO 20
<211> LENGTH: 23
<212> TYPE: DNA
<213> ORGANISM: Artificial Sequence
<220> FEATURE:
<223> OTHER INFORMATION: Cloning primer

<400> SEQUENCE: 20
ttaaattcag catccccct ttg                                      23

<210> SEQ ID NO 21
<211> LENGTH: 23
<212> TYPE: DNA
<213> ORGANISM: Artificial Sequence
<220> FEATURE:
<223> OTHER INFORMATION: Cloning primer

<400> SEQUENCE: 21
aatttaagtg catccccct ttg                                      23

<210> SEQ ID NO 22
<211> LENGTH: 30
<212> TYPE: DNA
<213> ORGANISM: Artificial Sequence
<220> FEATURE:
<223> OTHER INFORMATION: PCR primer

<400> SEQUENCE: 22
gctcatgatc agattgtcgt ttcccgcctt                              30

<210> SEQ ID NO 23
<211> LENGTH: 26
<212> TYPE: DNA
<213> ORGANISM: Artificial Sequence
<220> FEATURE:
<223> OTHER INFORMATION: PCR primer

<400> SEQUENCE: 23
tttccctcgg tctgatgcgt ctgagg                                  26

<210> SEQ ID NO 24
<211> LENGTH: 19
<212> TYPE: DNA
<213> ORGANISM: Artificial Sequence
<220> FEATURE:
<223> OTHER INFORMATION: PCR primer

<400> SEQUENCE: 24
ccacatcatt gggccaacc                                          19

<210> SEQ ID NO 25
<211> LENGTH: 29
<212> TYPE: DNA
<213> ORGANISM: Artificial Sequence
<220> FEATURE:
<223> OTHER INFORMATION: PCR primer

<400> SEQUENCE: 25
gatgcaatcg atatcagcca attttagac                               29

<210> SEQ ID NO 26
<211> LENGTH: 24
<212> TYPE: DNA
<213> ORGANISM: Artificial Sequence
<220> FEATURE:
<223> OTHER INFORMATION: PCR primer

```
<400> SEQUENCE: 26
cggctccact ccaccggaga aggg                                    24

<210> SEQ ID NO 27
<211> LENGTH: 23
<212> TYPE: DNA
<213> ORGANISM: Artificial Sequence
<220> FEATURE:
<223> OTHER INFORMATION: PCR primer

<400> SEQUENCE: 27
ctctgctcga agctaagcca ccc                                     23

<210> SEQ ID NO 28
<211> LENGTH: 19
<212> TYPE: DNA
<213> ORGANISM: Artificial Sequence
<220> FEATURE:
<223> OTHER INFORMATION: PCR primer

<400> SEQUENCE: 28
gaacatcggt ctcaatgca                                          19

<210> SEQ ID NO 29
<211> LENGTH: 29
<212> TYPE: DNA
<213> ORGANISM: Artificial Sequence
<220> FEATURE:
<223> OTHER INFORMATION: PCR primer

<400> SEQUENCE: 29
cgcctttcgt cggagacgga ttcatcccc                               29

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
ctcctctgca cctcttctcc                                         20

<210> SEQ ID NO 31
<211> LENGTH: 30
<212> TYPE: DNA
<213> ORGANISM: Artificial Sequence
<220> FEATURE:
<223> OTHER INFORMATION: PCR primer

<400> SEQUENCE: 31
ggcaatcagc tgttgcccgt ctcactggtg                              30

<210> SEQ ID NO 32
<211> LENGTH: 21
<212> TYPE: DNA
<213> ORGANISM: Artificial Sequence
<220> FEATURE:
<223> OTHER INFORMATION: PCR primer

<400> SEQUENCE: 32
atattacgtg taacatgcgt c                                       21

<210> SEQ ID NO 33
<211> LENGTH: 24
```

```
<212> TYPE: DNA
<213> ORGANISM: Artificial Sequence
<220> FEATURE:
<223> OTHER INFORMATION: PCR primer

<400> SEQUENCE: 33
aacaaaaggt ccaaatctca tgtg                                        24

<210> SEQ ID NO 34
<211> LENGTH: 28
<212> TYPE: DNA
<213> ORGANISM: Artificial Sequence
<220> FEATURE:
<223> OTHER INFORMATION: PCR primer

<400> SEQUENCE: 34
ctgccgctct agtccggtcg atctctcg                                    28

<210> SEQ ID NO 35
<211> LENGTH: 28
<212> TYPE: DNA
<213> ORGANISM: Artificial Sequence
<220> FEATURE:
<223> OTHER INFORMATION: PCR primer

<400> SEQUENCE: 35
acgccgaatt cggatgggaa gcggcggg                                    28

<210> SEQ ID NO 36
<211> LENGTH: 22
<212> TYPE: DNA
<213> ORGANISM: Artificial Sequence
<220> FEATURE:
<223> OTHER INFORMATION: PCR primer

<400> SEQUENCE: 36
aatggaaagg tagggtcaac gc                                          22

<210> SEQ ID NO 37
<211> LENGTH: 24
<212> TYPE: DNA
<213> ORGANISM: Artificial Sequence
<220> FEATURE:
<223> OTHER INFORMATION: PCR primer

<400> SEQUENCE: 37
gtatgttcag atatagatcg acag                                        24

<210> SEQ ID NO 38
<211> LENGTH: 30
<212> TYPE: DNA
<213> ORGANISM: Artificial Sequence
<220> FEATURE:
<223> OTHER INFORMATION: PCR primer

<400> SEQUENCE: 38
tgatagtgac cttaggcgac ttttgaacgc                                  30

<210> SEQ ID NO 39
<211> LENGTH: 25
<212> TYPE: DNA
<213> ORGANISM: Artificial Sequence
<220> FEATURE:
<223> OTHER INFORMATION: PCR primer

<400> SEQUENCE: 39
```

-continued ctcgtctacg ctactcatgg catcc                                         25

<210> SEQ ID NO 40
<211> LENGTH: 24
<212> TYPE: DNA
<213> ORGANISM: Artificial Sequence
<220> FEATURE:
<223> OTHER INFORMATION: PCR primer

<400> SEQUENCE: 40
ctttatcttt tgcatgaacc ttcc                                          24

<210> SEQ ID NO 41
<211> LENGTH: 22
<212> TYPE: DNA
<213> ORGANISM: Artificial Sequence
<220> FEATURE:
<223> OTHER INFORMATION: PCR primer

<400> SEQUENCE: 41
ctcatcaacg ctactcgatt cc                                            22

<210> SEQ ID NO 42
<211> LENGTH: 26
<212> TYPE: DNA
<213> ORGANISM: Artificial Sequence
<220> FEATURE:
<223> OTHER INFORMATION: PCR primer

<400> SEQUENCE: 42
ccattccatg gcccacacat gggtcc                                        26

<210> SEQ ID NO 43
<211> LENGTH: 25
<212> TYPE: DNA
<213> ORGANISM: Artificial Sequence
<220> FEATURE:
<223> OTHER INFORMATION: PCR primer

<400> SEQUENCE: 43
ctgagctgct tttgcatcaa tgacc                                         25

<210> SEQ ID NO 44
<211> LENGTH: 26
<212> TYPE: DNA
<213> ORGANISM: Artificial Sequence
<220> FEATURE:
<223> OTHER INFORMATION: Cloning primer

<400> SEQUENCE: 44
gagcgtcggt ccccacactt ctatac                                        26

<210> SEQ ID NO 45
<211> LENGTH: 15
<212> TYPE: DNA
<213> ORGANISM: Artificial Sequence
<220> FEATURE:
<223> OTHER INFORMATION: Cloning primer

<400> SEQUENCE: 45
gatcctgcgg ccgct                                                    15

<210> SEQ ID NO 46
<211> LENGTH: 15
<212> TYPE: DNA
<213> ORGANISM: Artificial Sequence

```
<220> FEATURE:
<223> OTHER INFORMATION: PCR primer

<400> SEQUENCE: 46
tcgccgcggc cgcag                                                    15

<210> SEQ ID NO 47
<211> LENGTH: 32
<212> TYPE: DNA
<213> ORGANISM: Artificial Sequence
<220> FEATURE:
<223> OTHER INFORMATION: PCR primer

<400> SEQUENCE: 47
gatgtggcgg ccgctgagca gaggatgtgg ag                                 32

<210> SEQ ID NO 48
<211> LENGTH: 29
<212> TYPE: DNA
<213> ORGANISM: Artificial Sequence
<220> FEATURE:
<223> OTHER INFORMATION: PCR primer

<400> SEQUENCE: 48
ggacgcggcc gccgtacatg gccataagc                                     29

<210> SEQ ID NO 49
<211> LENGTH: 33
<212> TYPE: DNA
<213> ORGANISM: Artificial Sequence
<220> FEATURE:
<223> OTHER INFORMATION: PCR primer

<400> SEQUENCE: 49
atggaaatgc ggccgcttga aagaagatc tgg                                 33

<210> SEQ ID NO 50
<211> LENGTH: 33
<212> TYPE: DNA
<213> ORGANISM: Artificial Sequence
<220> FEATURE:
<223> OTHER INFORMATION: PCR primer

<400> SEQUENCE: 50
gctaatggcg gccgccatat gtctgattac acc                                33

<210> SEQ ID NO 51
<211> LENGTH: 33
<212> TYPE: DNA
<213> ORGANISM: Artificial Sequence
<220> FEATURE:
<223> OTHER INFORMATION: PCR primer

<400> SEQUENCE: 51
attgatgcgc ggccgcttga gagacggatg tgg                                33

<210> SEQ ID NO 52
<211> LENGTH: 33
<212> TYPE: DNA
<213> ORGANISM: Artificial Sequence
<220> FEATURE:
<223> OTHER INFORMATION: PCR primer

<400> SEQUENCE: 52
gcaatatgcg gccgcatatg attgatcact gcc                                33
```

<210> SEQ ID NO 53
<211> LENGTH: 20
<212> TYPE: DNA
<213> ORGANISM: Artificial Sequence
<220> FEATURE:
<223> OTHER INFORMATION: PCR primer

<400> SEQUENCE: 53
cgtttggaat cactacaggg                                        20

<210> SEQ ID NO 54
<211> LENGTH: 17
<212> TYPE: DNA
<213> ORGANISM: Artificial Sequence
<220> FEATURE:
<223> OTHER INFORMATION: cDNA Library Screening primer

<400> SEQUENCE: 54
gagatggtgc acgatgc                                           17

<210> SEQ ID NO 55
<211> LENGTH: 30
<212> TYPE: DNA
<213> ORGANISM: Artificial Sequence
<220> FEATURE:
<223> OTHER INFORMATION: cDNA Library Screening primer

<400> SEQUENCE: 55
gctccaaaag ttcgacaatt tcgtaggggc                             30

<210> SEQ ID NO 56
<211> LENGTH: 27
<212> TYPE: DNA
<213> ORGANISM: Artificial Sequence
<220> FEATURE:
<223> OTHER INFORMATION: cDNA Library Screening primer

<400> SEQUENCE: 56
cgctcttctc cgtcttcttc tcatccc                                27

<210> SEQ ID NO 57
<211> LENGTH: 26
<212> TYPE: DNA
<213> ORGANISM: Artificial Sequence
<220> FEATURE:
<223> OTHER INFORMATION: cDNA Library Screening primer

<400> SEQUENCE: 57
atgttgtgtg catcatcttc gcttgc                                 26

<210> SEQ ID NO 58
<211> LENGTH: 28
<212> TYPE: DNA
<213> ORGANISM: Artificial Sequence
<220> FEATURE:
<223> OTHER INFORMATION: cDNA Library Screening primer

<400> SEQUENCE: 58
gtcaaggaac ggtcaagcga tcagaacc                               28

<210> SEQ ID NO 59
<211> LENGTH: 3886
<212> TYPE: DNA
<213> ORGANISM: Arabidopsis thaliana

<400> SEQUENCE: 59

-continued

```
attttagctt gttgttgttt gataaagatc caagataata tgaaatcact ttttaaaaat    60
taatctattt aatgtcacac atcaactatt ttatctttcc atttcagaat tttgattttt   120
ttcggtagaa tataatggag ctctgatgag tatgtgaccc actaatcaaa tggttcattg   180
actagctcgg ttttaagctt taagtccttg agatcattat cttcaacaga agacttataa   240
atactatttt atttgaggaa atgatagggt tattcaacaa gtatatatat gctcatcttt   300
taaaaggggg ataagtatta cttttgtttc aaacaaaatg gataaacatc tgagggaaga   360
aggtaggacc aatataaaag tggaaaaatt aggtactctg ctccgtacaa gaatatggct   420
catgggcaaa atacattggg tttatgattc atctccccccc ttcacatatg tacaatgtat   480
tatatcatgt tgttcttctt gtccccattc ttgatatctt aaatatttaa gtccaattca   540
tataattgag caataattat gtttgaactc attagttatt gcttatgaaa actgatcaaa   600
acaacaaaaa gttgacgttt taagttttgc attcaaacta gggcaactgt gttagtttta   660
tcttcgacga cgtggatata agttttttaa aattatgtag gtataataaa ttaaatagaa   720
agaaaaaaac tatataatga aacaaaagag aaacagagga gagtttgatg gtttaggacg   780
aatctggttt atttagttca gccaataaaa gcatagttcc aatgcaagtg ggaacatcaa   840
ctaagtctca ctacttttta aaatagtcga ataaatctgc atgcagtact ttgttatgcg   900
tatataatat caaatagtag tacaatttga taaaaatgtt atatgtttaa tttggtggat   960
catagaagga ttaatttttta tgatcaaata acgaagccac gaagaactaa atctgaccgt  1020
ttgatgctta ttcgagaact ataacaatat taggacgtca ttcatgtatc tttattaaaa  1080
atatgtgatc ttaaacaaag cttcgtgcat agataagaag ggactagtca ctctaataag  1140
atcaataaga tatgttgttt ctctttgtaa accgaaaata gtgggcaatt agatcacgag  1200
tcttggcttt gctggcgtat tccaacgttg tcttatcatt atctcaaaat attattatag  1260
gtcgtctcat ttcatacccg tcaaaataat agttgttctt atatgtttcg aacaagtcac  1320
tttaggaatt aggatggaaa acatatccta tttgagtggt attggttaat ttgagaaatt  1380
gagcgtaaag gaagacaatg cgtaagaaag gcaacaatac gtactatgat tctacgtaca  1440
aagaaagtgc ttaggggata aaaccaaac taggtaagga cttgtaggaa acataagaga  1500
acctaatgat caagacctcc ccaactaaag caaaatatgt aaagagacac gtcatgttcc  1560
aaatatggaa ggacgaatat agtttcaaga aaagcctcat gatcaaaggg gggatgcact  1620
atttaattag agaatcacaa caaaacaaaa caaaaggtcc aaatctcatg tgaaccccct  1680
tcccacttgg ccctctattc tatccccatt tgtgctatta cacatcgccc attactcatt  1740
tttctatctc tcaacgagtc aactctattc aataatttta catatctttc tactactatt  1800
cttgtatgga ccattcgatt tttggaaact tcttttctct taaaaaaaca tcaataatat  1860
cgggcgaaat gtcaaatgtg gttttttctta gccctattta ccattcttaa ccacatcaag  1920
aatctcattg ctagtgttgt aattattctt tgtcctttag tgaaaacatt aagaaaaatt  1980
catctattga tgttcacgtt ctctgtaaat ttttttataga cgcatgttac acgtaatata  2040
ttattagttt attaccatat gaagggacta attatggcaa caacaagatt ataaaaaag  2100
gactaatcaa aagtaccaa aattagtacg aatgtaataa ataaataaa actttatgac  2160
actagcacac atattttttgg actcttccca cgaaacttcc tctacaaaac acattttgcc  2220
atttgttgca agacttgacc ctactcctct gcacctcttc tcctttctct tttattttat  2280
tttcacctttt ctttcataaa tacacataca ttacccacat tttacattta tctcttatta  2340
```

| | |
|---|---|
| tcctattcaa ttttgacaaa acaaaacaaa taatatcaac aacgtacatg cacttccttg | 2400 |
| tgtatatata taaactccaa accccatctc ttcataaagc aacaaaaact taacccattt | 2460 |
| cttcttcttt ttttgtttct ctctcacaaa cacaacaaat atggaataca gctgtgtaga | 2520 |
| cgacagtagt acaacgtcag aatctctctc catctctact actccaaagc cgacaacgac | 2580 |
| gacggagaag aaactctctt ctccgccggc gacgtcgatg cgtctctaca gaatgggaag | 2640 |
| cggcggaagc agcgtcgttt tggattcaga gaacggcgtc gagaccgagt cacgtaagct | 2700 |
| tccttcgtcg aaatataaag gcgttgtgcc tcagcctaac ggaagatggg gagctcagat | 2760 |
| ttacgagaag catcagcgag tttggctcgg tactttcaac gaggaagaag aagctgcgtc | 2820 |
| ttcttacgac atcgccgtga ggagattccg cggccgcgac gccgtcacta acttcaaatc | 2880 |
| tcaagttgat ggaaacgacg ccgaatcggc ttttcttgac gctcattcta aagctgagat | 2940 |
| cgtggatatg ttgaggaaac acacttacgc cgatgagttt gagcagagta gacggaagtt | 3000 |
| tgttaacggc gacggaaaac gctctgggtt ggagacggcg acgtacgaaa cgacgctgt | 3060 |
| tttgagagcg cgtgaggttt tgttcgagaa gactgttacg ccgagcgacg tcgggaagct | 3120 |
| gaaccgttta gtgataccga aacaacacgc ggagaagcat tttccgttac cggcgatgac | 3180 |
| gacggcgatg gggatgaatc cgtctccgac gaaaggcgtt ttgattaact tggaagatag | 3240 |
| aacagggaaa gtgtggcggt tccgttacag ttactggaac agcagtcaaa gttacgtgtt | 3300 |
| gaccaagggc tggagccggt tcgttaaaga gaagaatctt cgagccggtg atgtggtttg | 3360 |
| tttcgagaga tcaaccggac cagaccggca attgtatatc cactggaaag tccggtctag | 3420 |
| tccggttcag actgtggtta ggctattcgg agtcaacatt ttcaatgtga gtaacgagaa | 3480 |
| accaaacgac gtcgcagtag agtgtgttgg caagaagaga tctcgggaag atgatttgtt | 3540 |
| ttcgttaggg tgttccaaga agcaggcgat tatcaacatc ttgtgacaaa ttctttttt | 3600 |
| ttggtttttt ttcttcaatt tgtttctcct ttttcaatat tttgtattga aatgacaagt | 3660 |
| tgtaaattag gacaagacaa gaaaaaatga caactagaca aaatagtttt tgtttacatc | 3720 |
| taatttagga tctgtttttt caccctttcc tgaaatatga tatgtgttct cctccttaat | 3780 |
| ctaataatct tgtttaatct ttggtttata gccaacttta tagcatattt ttccaattga | 3840 |
| aatagagttg ttatgagtat ataatcccac actaatattt atgcat | 3886 |

<210> SEQ ID NO 60
<211> LENGTH: 3859
<212> TYPE: DNA
<213> ORGANISM: Arabidopsis thaliana

<400> SEQUENCE: 60

| | |
|---|---|
| ttctcaggat attttctatc aatatgctta attttctttc tttttttgtt aaagaaatta | 60 |
| attcccatag ttaacatgag agggtttagc aaaatatgct taattttctt gttcgctgat | 120 |
| gttttttattt ttatttatta ttactgattc agcattcaaa cttatcatgt gatttggatg | 180 |
| gttattgaag tttcatatta attgataaat taaatgtgtt gggatgatga gaggtgatat | 240 |
| agaaatacat attgtagtgt ttaaatagat atggattcaa gtatataatt aattcttctt | 300 |
| aatcaaatta atttgagttg gactagtagt ctagtaagta gtaagagaac atattcggat | 360 |
| ggtatcttaa atttatgaaa tacagtgtgt tttcagtttt tattggtagc aacaaattta | 420 |
| tcggttcata cctcaaagat agtattatac gtgtctacga ttatataaaa aaatcaatac | 480 |
| aaaataattg ttcattcaag aaacaatcgg acgatatgaa cattatagtt acaaactagt | 540 |
| aaaaagctat aaatatgtaa agtgaaaact atttaaaagg gtgaaaatta aaacgtatca | 600 |

-continued

| | |
|---|---|
| acgttggagt gtttcaaaaa tatttggttg gataagctca aactagtcaa attgtctccc | 660 |
| ctcccaagcg ggaacatcac gccatgtcca caataaatcc attttctttt ctctcaaata | 720 |
| tatatagaga tacatacatc gatactattc tatatattat gtaacaaatt agaaatatca | 780 |
| tataccacat ggtaagttgt ataaagagaa ttattagtgt ttgcttattg caaaattaat | 840 |
| acaaaacatt ttctattgaa gagctacaaa ttaagaagga aactgaaaaa tataataaaa | 900 |
| agcagaatat gttacgatat ttgtatgagt gtatgagaca acagtatcag ataagatcat | 960 |
| aatccttgcg accaacctat ccaaaagtct cttttttgtt ttctaatcaa tttacaaaac | 1020 |
| atttaaccaa taaaaatata aagatggtga aaaaaatatg gtcatacaac aattgcttca | 1080 |
| aaggggatg aactaaaata taccaaaaaa agaagtgagg ataggttcat gtgagccccc | 1140 |
| atcccacttg accctcttgg taggtccaca tttaccatga acatgtaacc cattggttat | 1200 |
| tcatttgtat gtattgtttt ttgtcaatga cttaattta ttttattttc ttcttctctg | 1260 |
| actttttttt gtttatctga ctcttctatg tatgtcaaaa tgtagcaaga taattgaaca | 1320 |
| tatttggatt gttgaaaaac atatcgatat ttagtgaatt agtttctcct ccaagcatct | 1380 |
| agaatgtcat aactgtgttg aattgtacat aaaatttgat atggattgat cattgataat | 1440 |
| aaatcaatga attaatgatc tattagaata tgaactttc attcaaattt aattgataat | 1500 |
| aagtggattt gtctatatgt aatattttag tcaaaaaaat tgtttctttt caatgcgata | 1560 |
| ttattatcct taaaacgttt tctcgagata attttttttcc gagccattaa ttttagtatg | 1620 |
| ttcagatata gatcgacaga aaaactataa ttacgtcgga ccaattgtag attggattga | 1680 |
| atacatatgg atcagattct aataccatat tagaatatga ggtatctaat tcaaaaccaa | 1740 |
| ctattaataa atagattgac tcatatatgt cttatatact agtcaagatt tctttgtctt | 1800 |
| ttctaatgtg ggatattatt atccctaata tcatgaataa aatcaagagt taatgtttaa | 1860 |
| ctatatctaa tctatactac ccatcttttt tcggaaacta tatataagtt ataaaaccaa | 1920 |
| gaaattctcg ttatccaata aaaataataa ttttgactat ggttatatat cagtttcaac | 1980 |
| aacttatatg atgattgatg agaaccttat tttatgaaag tacgtggtaa tgtgttgtaa | 2040 |
| gaaaatgttc ttacgccgtt gaaatatttt tccaaaaaat gtacataaca aacgtacgat | 2100 |
| atgtatgtaa aagccgtggt actacattta tttttgtctg cccttctcgg aaacttcctt | 2160 |
| caaagttatt tttgccgttc ttgaaagcgt tgaccctacc tttccatttt taaaatgttc | 2220 |
| tctcattttg acccattttt ttccataaac caatcaaatt ttaactttca aaaacataaa | 2280 |
| actaattaga tataaaataa taacatgtac atgcacttgc ctcgtccatt cctcacatca | 2340 |
| tcatatgtct ttgtatatat atagatgaac caaagaaatg aaaaagtaac aacgtcacct | 2400 |
| aaatctctct cacccaattt gtgtttcttc tttctgctaa aaggttataa ttttttgtttc | 2460 |
| ttggtttggt gagaatcttc aagaaactga acaaagaaa atggattcta gttgcataga | 2520 |
| cgagataagt tcctccactt cagaatcttt ctccgccacc accgccaaga agctctctcc | 2580 |
| tcctcccgcg gcggcgttac gcctctaccg gatgggaagc ggcgggagca gcgtcgtgtt | 2640 |
| ggatcccgag aacggcctag agacggagtc acgaaagcta ccatcttcaa aatacaaagg | 2700 |
| tgttgttcct cagcctaacg gaagatgggg agctcgatc tacgagaagc accaacgagt | 2760 |
| atggctcggg actttcaacg agcaagaaga agctgctcgt tcctacgaca tcgcagcttg | 2820 |
| tagattccgt ggccgcgacg ccgtcgtcaa cttcaagaac gttctggaag acggcgattt | 2880 |
| agcttttctt gaagctcact caaaggccga gatcgtcgac atgttgagaa aacacactta | 2940 |

```
cgccgacgag cttgaacaga acaataaacg gcagttgttt ctctccgtcg acgctaacgg   3000
aaaacgtaac ggatcgagta ctactcaaaa cgacaaagtt ttaaagacgc gtgaagttct   3060
tttcgagaag gctgttacac ctagcgacgt tgggaagcta aaccgtctcg tgatacctaa   3120
acaacacgcc gagaaacact tccgttacc gtcaccgtca ccggcagtga ctaaaggagt    3180
tttgatcaac ttcgaagacg ttaacggtaa agtgtggagg ttccgttact catactggaa   3240
cagtagtcaa agttacgtgt tgaccaaggg atggagtcga ttcgtcaagg agaagaatct   3300
tcgagccggt gatgttgtta ctttcgagag atcgaccgga ctagagcggc agttatatat   3360
tgattggaaa gttcggtctg gtccgagaga aacccggtt caggtggtgg ttcggctttt    3420
cggagttgat atctttaatg tgaccaccgt gaagccaaac gacgtcgtgg ccgtttgcgg   3480
tggaaagaga tctcgagatg ttgatgatat gtttgcgtta cggtgttcca agaagcaggc   3540
gataatcaat gctttgtgac atatttcctt ttccgatttt atgctttcgt tttttaattt    3600
tttttttttg tcaagttgtg taggttgtga ttcatgctag gttgtattta ggaaaagaga   3660
taagaccaaa aaataaattg gaacaatggt tttgtggaaa agtggtaaat agacctacct   3720
catagtaaaa cgttaccgga tacaacctaa atgtttatcc gttcctaaaa ctagatgaat   3780
caaattaatt aactatctaa aattgcatga taaatcggaa aaagaggatg aattcttggc   3840
aatttcatcc attaccgta                                                 3859

<210> SEQ ID NO 61
<211> LENGTH: 3802
<212> TYPE: DNA
<213> ORGANISM: Arabidopsis thaliana

<400> SEQUENCE: 61
accaaatagc cttggaccaa tccactctat cctctaaaaa atttaattga aaccatgtcg     60
cagctgaggg aaacacacat gaagctcaat tcctctaacc ttccacaaga agagatcatc   120
ttctgcatca tcttggaggt tcaccacatt agaaaccgga agacagttat tgagcatttg   180
ataattgggg ttcctgttcc tacttctatt aatccaccat tccccatcat cttggaagtt   240 ttttctttt cttaatttgt cttcagatta tgtttctgtt tgtactctta aatggaaccc     300
aatttcataa ggaaacatga catttctcat ttctttgttt catagagtta tattccgtat   360
ttgttaaaac tagtttcaaa aagtgatatt agctgttgat aaagaaaaaa aaaaggtgat   420
aatagcttgt tttataaaag tacacttgag aaaaagaaaa acaaagggtg gtactgttga   480
gtgttgacat atgatcgtta ttacctgtaa tagtattaaa attattgtta tatgggatt    540 ggccatacaa gcgaccgacc taaatatgga aagtaagatg acgtaagcaa agcttataaa   600 atttatttc cacctatcac gttttgatc gatgatacga agctatacta agtttttatt     660
tttttaattc atcagtaaac ttttactaaa taaggtaata ctatacaaaa aaagttaaaa   720 gtaactttt aaataaattt tttgatattc gcttttataa tcgtaactta ttaaagcggt    780
atatttatat attaaagttt aaaaaatcct gataagtaga aaataaaata aaaaattaaa   840
gaaaatttgg ggaaaaaaaa tcatattaat atatacttca tattttttatt cactaagaaa   900 atatctttt catatttcct ctaattatt ttctgaaatt tataaaataa aattattgta     960
gtaaaacaat ttataataaa aattaaattt tattttaaa cagtgattgc tatttttattt  1020 acaaattaat agttaattca actctaaagc taaaattaga atattgtttt tggttatgaa  1080
atcatgtgta tgaagtaac aacatttat tttttgagta ttaaatcgca caatgtaatt    1140
atatatattt ttttcaatca aaaataatgt tattaaacat ccaaataaaa aaggggggatt  1200
```

```
tttttggctt tttccttata ttttgctcta aaaatagaga tgaatagtgt tgcctaaaat    1260
ttaaaaatat gttttaatac taaaatttgt gctcattata atatatgtaa ttgttatata    1320
cataaattta tgtgtgtgta tatatatata tatatatata gaccaaaaag ttgaatatag    1380
acgatgattt attttctctt tatgtaagca cggatctgat gctatgtata caaaaaagat    1440
agaataacga aaaggtatga tctcgagcat tgaaccattg catttgtata tacatgaagg    1500
attcatgctt gcaaaaagat cctcacggaa caaaattcat tgagatttgg agaaaaacat    1560
attaattttt agtgagaaag gaataatatc gtaacagtta atttgcatct ctatagtaag    1620
aaaatagatc gaattccttc agctccaact ttttttattta ttttcttta caacaatttg    1680 ctaatcatta tattatttta atcaccatgc ttgtaaatta acaaattgta tataacatca    1740
gggggaatga acttaactaa ataatattct atttatcatg tgaatctctt ttatatctta    1800
tggtccactt gccgacccca cttccccatg cagcccacaa catattcata tcaccttttt    1860
tcgtcgtgaa tatcataaaa aaagtttggt gataatcggt atcaaacagt gaaaggaatg    1920
gtatatatag agcaatcata aaataaaaaa taaaaattaa agaaacttaa gatcaaacaa    1980
gttttgctga ttaataagta ataaccataa aatataaaat aaatttagat tcatgatttt    2040
ttgggggtac ttttagctat agttttaata tatgcatcgt agatatatat tgattgagtt    2100
aatttatttt atatataatt atttgtttaa ttgaaacata aacctaatat ggaaatgcga    2160
atttaacctt cttttttttaa gtattcttta tcttttgcat gaaccttcct ttgtatttaa    2220
gttgacccac aacatataca cacacaaacc catattattc cgatacacct acccatatat    2280
tataccatct ccttaaaaca cactacaagt aataaaaagg acggaacttt tttttttaat    2340
aacatacatg cacacttgat gtttcttatt tccccttgtc tctctatata tacacacatt    2400
cattcacaca cgttcacaca tatacattca cattactaat ctctcaagat ttcacaattt    2460
tcttgtgatt ttctctcagt ttcttatttc gtttcataac atggatgcca tgagtagcgt    2520
agacgagagc tctacaacta cagattccat tccggcgaga aagtcatcgt ctccggcgag    2580
tttactatat agaatgggaa gcggaacaag cgtggtactt gattcagaga acggtgtcga    2640
agtcgaagtc gaagccgaat caagaaagct tccttcttca agattcaaag gtgttgttcc    2700
tcaaccaaat ggaagatggg gagctcagat ttacgagaaa catcaacgcg tgtggcttgg    2760
tactttcaac gaggaagacg aagcagctcg tgcttacgac gtcgcggctc accgtttccg    2820
tggccgcgat gccgttacta atttcaaaga cacgacgttc gaagaagagg ttgagttctt    2880
aaacgcgcat tcgaaatcag agatcgtaga tatgttgaga aaacacactt acaaagaaga    2940
gttagaccaa aggaaacgta accgtgacgg taacggaaaa gagacgacgg cgtttgcttt    3000
ggcttcgatg gtggttatga cggggtttaa aacggcggag ttactgtttg agaaaacggt    3060
aacgccaagt gacgtcggga aactaaaccg tttagttata ccaaaacacc aagcggagaa    3120 acatttccg ttaccgttag gtaataataa cgtctccgtt aaaggtatgc tgttgaattt    3180
cgaagacgtt aacggaaaag tgtggaggtt ccgttactct tattggaata gtagtcaaag    3240
ttatgtgttg accaaaggtt ggagtagatt cgttaaagag aagagacttt gtgctggtga    3300
tttgatcagt tttaaaagat ccaacgatca agatcaaaaa ttctttatcg ggtgaaatc    3360 gaaatccggg ttggatctag agacgggtcg ggttatgaga ttgtttgggg ttgatatttc    3420
tttaaacgcc gtcgttgtag tgaaggaaac aacggaggtg ttaatgtcgt cgttaaggtg    3480
taagaagcaa cgagttttgt aataacaatt taacaacttg ggaaagaaaa aaaagctttt    3540
```

-continued

| | |
|---|---|
| tgattttaat ttctcttcaa cgttaatctt gctgagatta tttatgttgt aagttgtaac | 3600 |
| aagtggaaaa aattaattag gtgtcaaaca atcttgtgt taatattctt tgtataatgt | 3660 |
| atggatgagc tgttattaat tactgtaatt tttaattggg catactcgta attttaattg | 3720 |
| ggcattattg gtttataggc ccattaaagt gtttcttcct catattcttt ctttggtccg | 3780 |
| ttgcttattc accagggaaa aa | 3802 |

<210> SEQ ID NO 62
<211> LENGTH: 3835
<212> TYPE: DNA
<213> ORGANISM: Arabidopsis thaliana

<400> SEQUENCE: 62

| | |
|---|---|
| ggtgaggggg gggggggcgc cgcgggacgg aatagacgcc ctgttgagcc ctatgttgag | 60 |
| catcatgatt accaactttc actatgtttg taatatctat aaaaatatgc aatgatataa | 120 |
| attccaaaca aaatttacaa aacgataga agaaactaac taattctgat atgatcaaat | 180 |
| caaaagtata aacaatgaa agtgtactgg agaaaatgtc tctcttttgt aagcagaggt | 240 |
| tacacaactt caataatgta tcacttacaa aaccattttt tcaatttgga gctcaaatac | 300 |
| ttagaatcat aaaagaaaca tggatgagcc caatctctct tacggagaca aattccatga | 360 |
| gaaaagaaag ctgagttagc aacaagtgcc acgtgacaac atactcaatt tcttctaagg | 420 |
| aaaatacaac catctatttc tttttgtcgc atacccaccc atatatgata tacttagaac | 480 |
| cattttaagt tttttaaaa cataaaaata cgatttaaa tttgaaaatt tgattagagt | 540 |
| gtgattatct aattattgtg ttgtctataa atctacacag tcactacttt ctaccacact | 600 |
| gatttttaaca aaatcaatta aagttgatca gcacttattt ctttcatatg ggcttaaatg | 660 |
| ccaatttact tatatatatt ttgatgaaaa tgtgtggtaa aacttaagaa acaaaaaaat | 720 |
| cctaacacta attagcgcct aggtatttg agcaatgcct ctttaactta aaagaaaaa | 780 |
| aacgaaaaaa gacaaaagta attgtcctgc tgtcaagaaa tgcccatatt attattcatc | 840 |
| cacacaagac acgtacgacc atgcctctta gtgatttgtc attggcccac ttcccatcct | 900 |
| agtggatcaa attgataata atactataa taaataatta caagaattca atagaaacc | 960 |
| ggcaaatcaa ttaatagata taaaaggag atataaatcg ttaacatttt ctattggagc | 1020 |
| agggagagcc aataaaagtc gaatctcacg atatttcgca gttctctaat tggctctttg | 1080 |
| cataaaaaat gaaacctaac taatgggtag aagaatactt ttgcaaagca acaaatatat | 1140 |
| cagataagat cgtaagctat ccacatcact tgttaattgt cctcaaacca tattatataa | 1200 |
| tgcaaacaat ttatgcgtt aaatccttac gtatttattc tctataagag taaaacacac | 1260 |
| acactgaagg caactgattt aattggattt ctattgacca gtagaaatac ttgttatgat | 1320 |
| gtcggtcgct cgttggctaa gtatttctta taaatatata agacatattt aaaatctttt | 1380 |
| tacattacat acacccactt atgagaaaca aatataataa aatgttgata ccaaatatat | 1440 |
| atatatatat ataataaat gggataatta caagaacaac aaaagagaga ttttttatga | 1500 |
| atttggaatt ggaatctatc gagtgcatat attatacgga caataatcct catagcaata | 1560 |
| cacatttttt ctataaaaag aaacgtagga taagattata gaaagaagaa taaaaacctg | 1620 |
| gaaatggaaa ataagaaga tatatatcat gagttcatga ctaaacaact atttatagct | 1680 |
| ttttcaataa taatatcatt caagagtgaa gaataacaat cagatttgga agagaaaaaa | 1740 |
| atttaaagag agacaccatt taacatcggt aggatctgaa catggttatc aaatctaata | 1800 |
| cttttctattt tattattttt catatagtta ttatcgttac tatagtatta tagtgaatta | 1860 |

```
aaattttaag catcaaaact caggggggat gaacttcact aaaatgatgt caatatctca   1920
cgtggaccct ttatccattc catggcccac acatgggtcc cacttcccca tgcacacagc   1980
ccacaacata ttcatttcta tatttgttcc tatactctct tttctctttt tcttacataa   2040
ataaaatact aacttattat aaggattatt attgcttcgt gtgttttctt ctataagtta   2100
catcaacagt tcatgaaata daccctaata tagtaaccta aattaaatgc cgtatatttc   2160
attatgtttc cacgaagctt cctttgtgtt ctttgagttg acccatacac acccatctta   2220
cttcccatgc acctgcacat atactataat tactcccctc aaacacgcat tcttacaaat   2280 atatttttg ttattaccaa ataaaagtg aaacataaaa taataatatc agaagtgaca    2340
cttgctgttt cttatttccc tcccccaag ctctttctcc ttctttctat atatattata    2400
cacacacacg tatacatata cacaacataa ttcacaacac aacacaaaca catttctgtt   2460
ttctccattg tttcaaacca taaaaaaaaa cacagattaa atggaatcga gtagcgttga   2520
tgagagtact acaagtacag gttccatctg tgaaaccccg gcgataactc cggcgaaaaa   2580
gtcgtcggta ggtaacttat acaggatggg aagcggatca agcgttgtgt tagattcaga   2640
gaacggcgta gaagctgaat ctaggaagct tccgtcgtca aaatacaaag gtgtggtgcc   2700
acaaccaaac ggaagatggg gagctcagat ttacgagaaa caccagcgcg tgtggctcgg   2760
gacattcaac gaagaagacg aagccgctcg tgcctacgac gtcgcggttc acaggttccg   2820
tcgccgtgac gccgtcacaa atttcaaaga cgtgaagatg gacgaagacg aggtcgattt   2880
cttgaattct cattcgaaat ctgagatcgt tgatatgttg aggaaacata cttataacga   2940
agagttagag cagagtaaac ggcgtcgtaa tggtaacgga aacatgacta ggacgttgtt   3000
aacgtcgggg ttgagtaatg atggtgtttc tacgacgggg tttagatcgg cggaggcact   3060
gtttgagaaa gcggtaacgc caagcgacgt tgggaagcta aaccgtttgg ttataccgaa   3120
acatcacgca gagaaacatt ttccgttacc gtcaagtaac gtttccgtga aggagtgtt    3180 gttgaacttt gaggacgtta acgggaaagt gtggaggttc cgttactcgt attggaacag   3240
tagtcagagt tatgttttga ctaaaggttg gagcaggttc gttaaggaga gaatctacg    3300 tgctggtgac gtggttagtt tcagtagatc taacggtcag gatcaacagt tgtacattgg   3360
gtggaagtcg agatccgggt cagatttaga tgcgggtcgg gttttgagat tgttcggagt   3420
taacatttca ccggagagtt caagaaacga cgtcgtagga aacaaaagag tgaacgatac   3480
tgagatgtta tcgttggtgt gtagcaagaa gcaacgcatc tttcacgcct cgtaacaact   3540
cttcttcttt tttttttctt ttgttgtttt aataatttt aaaaactcca ttttcgtttt    3600
ctttatttgc atcggtttct ttcttcttgt ttaccaaagg ttcatgagtt gttttgttg   3660 tattgatgaa ctgtaaattt tatttatagg ataaatttta aaagggtta cttagatatg    3720 tctcaagagt tttattagca tgagatgatg aaaatgttgt taccaaatct taccttggtt   3780
tcttttcatt ttatgtgtat gggaactcgt atttatatgt atgcattagc tactg         3835
```

<210> SEQ ID NO 63
<211> LENGTH: 3895
<212> TYPE: DNA
<213> ORGANISM: Arabidopsis thaliana

<400> SEQUENCE: 63

```
tcatggagga tggacctact atcgatgaac agaaaaatga ataatcaaaa cttccctaaa     60
cacatatcaa tacgtgatga tactataacc aacagtaacg ttttcatgtc tttgctccta    120
```

-continued

```
cgtttatggc cacactactc aggaagattc ccaccaaatt ttcaaacctt acctacatat    180
ctaacaatcg tggtttaggt ggacaatcga tggaccaagt ctctgttggt ttccagttca    240
ttcgcagtgt aagttgttac tgctggaaaa tttcaaaggt gggaagaaca ggaaagagta    300
gagccgtaaa accatgggag acaacgaaga agaagaccaa tacaaggaag acagcaaaaa    360
tgaagaaaaa atagatgagg aagcaaatta gcaatgacag tagaaccatg ctgtgtccaa    420
caggatttac ctgtgttgcc atggtgtctc aacaggagg acaattctcg ctaggtgtaa     480
ccaataaaag atacaagcta ccaaaaatct ttacaaaaca agtaaacaa cttgtcgcaa     540 tagaagttaa agatacacac agcttaatgg tacgagagta aagatgcat aagtttatcc     600 cagaaacggt aaagaagttt gcagataaat agaagttga gtagaatgtc attatacaaa     660
ggaacatccc gttacatctg ccactacttg gtcctaaaca gtaaacacac aaaaaaaaac    720 aagatttac caaacacat atcaataaca acttaaactt agtaggatgg gaaaatttta      780
gagcttacga atctaataat ggtttagggt ggacacggta gaccgtttca atccctcgaa    840
ggtagcgaac ggcagcttga aaagtaatgg ggtcagtgtg agaattagca tccttggcct    900
cgaaggtgat gtagaaaatg aatccggctc catatttccg attagccttg acagctctca    960
caagttcaag attttccagc ttatcatcat tgtatttctg aagagcaatc ttggataatc   1020
tatgaaccaa atcccgtcg gtttcgggtt tatgagcaac gtcactatcc tcgaagataa    1080
caggatagca aaacacaagg cgtctttgtt tcgtggtgtc aaagtcgtaa tactacagac   1140
aacaatcaca ttcatgagag aagccgacat aatgcttttg aaatcacaga caaaatctca   1200
attcgaaaaa gtaagaagcg aaggagagat tggtggatca ttacaactac ataccccgct   1260 tcttggtat tcttcttcga ccaatcgttc atcttccgaa tcgaaactac acgtcgactc    1320
gctgtacgaa gacatctctt cgcaatcctc ctcctcctcc tcctcagct tctgacgctt    1380 cagatcaggc tcctcagatt tcttatcgac caccacctgc ggatccataa ctatggcaga   1440
ttagatgaaa ccctaattct ctgtttcttc tatcattcaa gataaaaaaa aggtccctct   1500
tctatttata gtgtgcacaa caaacaaaaa acaaaaagaa aaaagtgac taagaaaata    1560 tcaagcctcc aagagagaaa attcgtgtag agacactaaa ctagctagta gatgattatt   1620
gtaaaacctt atcatcattg tggttgttaa aattaatcta gatcggttaa atttggttaa   1680
aaaatactca ctagttttca agttaaaaa tccaaatccg gaaaattaaa agtcaaatca    1740
aatcataact attccttcct ttcgtataat caagtagacg aaatctcatc aaaattaaat   1800
ttctgaagtt ttaaattagg aatctcagat gtcttatttg cccatcacgg aagcagatgt   1860
gtaaccctaa ttggtcgtga tcgtggtgat tgcaaaagcc taattgttgt acatcattaa   1920
acgtacgttt tgtattcttt ccatttactg tgtaccttt tctgcttctc aaaacttgct    1980 aaattttac atagagaaat attttttgtta attttctttt tgtttttttgt tgacttattg   2040 gaaaacaaat aataatgaag aaataaaaaa atactcaac cacatgagat gagaaacgtt    2100
ttgttaatga atgataaaat tagggtaaac ataaaaccct aataagttac ttgatgatat   2160
tttccagcgg ctctctcacg tatttccatt tttatccaa tcagatatat caagtaatta   2220
atgaaccgac gaaacatgga aattctttaa tttcaatact ttccataatt ttctctcata   2280
gctaaattat agaaactaca acaaatagaa aatggaaaat gataacttga taaatactca   2340
agcaccgcaa gaaacaacaa gattaagaaa cacaatttgc tcccacgatt gctctctttt   2400
atatagttct ctctctgttc ctcatatttc ttcatcgttt tgtttcgctt ctctttctct   2460
gtctctcgta tcttttctact actctgtttc ttgaattcta atgaacaaca tcgacgacgc   2520
```

-continued

```
aaagacggag acttcagtgt cttcaggttc aagcgactct ttcttgcctc tcaagaaacg    2580
catgagactt gatgacgaac cagaaaacgc cctagtggtt tcgtcttcac caaagacggt    2640
tgtggcttct ggcaatgtca agtacaaagg agtcgttcag caacagaacg gtcattgggg    2700
tgcccagatt tacgcagacc acaaaaggat ttggcttgga actttcaaat ccgctgatga    2760
agccgccacg gcttacgata gtgcatctat caaactccga agctttgacg ctaactcgca    2820
ccggaacttc ccttggtcta caatcactct caacgaacca gactttcaaa attgctacac    2880
aacagagact gtgttgaaca tgatcagaga cggttcgtac caacacaaat tcagagattt    2940
tctcagaatc agatctcaga ttgttgcgag tatcaacatc gggggaccaa acaagcccg     3000 aggagaagtg aatcaagaat cagacaagtg tttttcttgc acacagcttt tcagaagga    3060 attgacaccg agcgatgtag ggaaactaaa taggcttgtg atacctaaaa agtatgcagt    3120
gaagtatatg cctttcataa gcgctgatca agcgagaaa gaagagggtg aaatagtagg     3180
atctgtggaa gatgtggagg ttgtgtttta cgacagagca atgagacaat ggaagtttag    3240
gtattgttac tggaaaagta gccagagctt tgtcttcacc agaggatgga atagtttcgt    3300
gaaggagaag aatctcaagg agaaggatgt tattgccttc tacacttgcg atgtcccgaa    3360
caatgtgaag acattagaag gtcaaagaaa gaacttcttg atgatcgatg ttcattgctt    3420
ttcagacaac ggttccgtgg tagctgagga agtaagtatg acggttcatg acagttcagt    3480
gcaagtaaag aaaacagaaa acttggttag ctccatgtta aagataaag aaaccaaatc      3540 agaggagaac aaaggagggt ttatgctgtt tggtgtaagg atcgaatgtc cttagggaat    3600
ttttctttaa aagtttctta cttcaactag aacttgtttt acttgtacct catgaatttt    3660
tattaacaaa attgttttac ttaactagag attggtttac taaatgattt tctcaatgct    3720
tcgttactgg tttagatttc gataaccatt atcaaagtga gctactcgca atgcataacc    3780
accaagattg ctagtttact catgacaagc tcagaagctt ttggccttat aagaagaaag    3840
acttaaccaa aaaatcttat caatagtatt tgttaactgg tcaattagtt tttat         3895
```

<210> SEQ ID NO 64
<211> LENGTH: 3859
<212> TYPE: DNA
<213> ORGANISM: Arabidopsis thaliana

<400> SEQUENCE: 64

```
ttaatgatgc tgagttgaaa ctcattgacg ctttgatcgg aattcaaggc cgtggcaaat      60
ctgcttctcc taaacagctc aatgtgtgta aaaactttaa actttcttta attttccgtc     120
gtgtttatga tttgagagat tctctgttgt aggatgttga atctgctgtg aaagttcttg     180
aaggtttaga aggcattcaa aatcctgtat gaaatgtttt cttgtgaatc cttttatctt     240
caaattacca aattctgtta tgttttgttc tttgactcat ttggttgtct ttgggggaat    300
gttgtttaaa tgtttagaca gattctgacc taatcgaagg tcgttggcga ttgatgttca    360
ccacaagacc tggaactgca tctccaatcc aagtcagttc ttctcacaca ttcatcatca     420
tatctccatt ttttctagat gattgtaatt tgtgtgtaag aagaagagca atggaaggat    480
ttgtctctgc agagaacatt tacaggagtt gatgtgttca ctgtgtttca agatgtatac    540
ttgaaggcaa caaacgatcc tcgtgtttca acattgttta attctctga tttcattgga     600 gagctgaaag ttgaggtgag tttcttcact aaagtctttg catcaaaaga ctggatgtt     660 tatactttga attgtttcat tttacaggca gttgcgtcga tcaaagatgg gaaacgagtt    720
```

-continued

```
ttattccgtt tgatagagc cgcttttgat ttgaagttcc ttcctttcaa agttccatat      780
ccagttcctt ttagacttct tggtgatgaa gcaaaaggtt ggctagatac tacttatttg    840
tcgccttcag gtaaccttag gatttctagg ggaaacaagg taaatgagtt tcttgattct    900 caaaagaaa  attaaagctt tatagcattt ttatccatga ggctgtatat ttgtagcgca    960
gggaacaacg tttgttcttc agaaagaaac cgtgcctagg cagaaattgt tagccaccat   1020
atctcaagac aaaggagtag ctgaggtaat gtgtcatgcc ttcaagaaat ctgaaaacaa   1080
tcgatagttt cggtttgaaa tggaaccaat ggatcgttta gtataaacac aggctatcga   1140
tgagtttctt gcgtctaatt ctaattccgc ggaagataat tatgagcttt tagaaggaag   1200
ttggcaaatg atttggagtt cacaggtcac ttctctgata actttagctt ttgtcttgaa   1260
caagcactta tattcgtttg ataagcgat  ttttcgggtt ttgtgtttgc agatgtatac   1320
agatagttgg attgaaaatg cagcaaatgg tcttatggga agacaggtaa acattttatt   1380
agaatgtctt aggtagtcta ttgttgcttc agctggcttc gtttagcgaa atcgagtatc   1440
ttattcagat cattgagaag gatgggagga taaagtttga agttaacatc attccggcat   1500
ttagattctc catgaaaggc aaattcatgt aagtctctgt cttttagatt agtcatttg    1560 ctaactttt  tgtgatcttg tttcttgact ggtctcatga atgatttgca gaaaatcaga   1620
aagcagtaca tatgacttga agatggacga cgcagcaatt ataggcggtg catttggata   1680
tccggtcgat ataacaaaca atatcgagct aaaaattctg taagatctct ctatcttctt   1740
cttctactac tttcacaaat cacaacatat aataatgcat ttgaattgct aatacagaga   1800
tgcttacttt aatgtttgta ggtacacaga tgagaagatg aggataagcc gaggattcga   1860
taacattatc tttgtgcaca tccgagaaat ttagctgcat tgttctatca gaacctctta   1920
tttgaacata tgaaaaaaa  tagtatgtaa gaaactgtca aatgttttac aacaatggaa   1980
ggtgatagtt taaattttct ctgttcatta gtttttttgg atgtaacagg aaccagaaaa   2040
aacaagaaac cacatgatat aattttcgct actaatgtct aaattaagac aaaattaaca   2100
ttaagaaaac ttactttttt gtcttaatct taaacaaatt cactgaatat ttcttctac    2160 aaagaaaata cgaatatctc actaacaaag gaaacttacc actaacagct tctggtggca   2220
ttaattactc tgtaaattgc cattttttca ccgagagaaa actagaaaaa caaaacaaaa   2280
catggaaact gtaacattct aaaagattca ttgttaacaa accaacaga  gaaacataat   2340 actgattttc caggatttac tccctcaaat ctctccttca aatactcttc ctaatctctt   2400
ctgttttcat tttgcttgtt ccctgcgaac atctctctct cttcctctgt ttcttgtttt   2460
tttgtccttt tcttgatttt tgtatttttt tgttatggat atggacgaga tgagcaatgt   2520
agccaagaca acgacagaga cttcaggctt aactgactct gtcttgagcc tcacgaaacg   2580
catgaaacct actgaggtta cgaccaccac aaaacctgcc ttgtccaaca cgacgaaatt   2640
caaaggagtt gttcagcaac agaacggtca ttggggtgct cagatttacg cagaccatcg   2700
aaggatttgg cttggaactt tcaaatccgc tcatgaagcc gctgctgctt acgatagcgc   2760
atcgattaag cttcgaagct ttgatgctaa ctcgcaccgg aacttccctt ggtctgattt   2820
taccctccat gaaccggact ttcaagagtg ctacacgaca gaagctgtgt tgaacatgat   2880
cagagacggt tcttatcaac acaagttcag agattttctc agaatccggt ctcagattgt   2940
tgcgaatatc aacatcgtgg gatcaaaaca agtcttagga ggaggagaag gtggtcaaga   3000
atcgaacaag tgtttctcgt gcacgcagct ttttcagaaa gaactgacac cgagcgatgt   3060
agggaaactg aataggcttg tgatacctaa gaagtatgca gtgaagtata tgcctttcat   3120
```

-continued

```
aagcgatgat caaagcgaga agagacgag tgaaggagta aagatgtgg aggttgtctt      3180 ttacgacaga gcaatgagac aatggaagtt taggtattgt tactggagaa gtagccagag   3240
ctttgtcttc accagaggat ggaatggttt cgtgaaggag aagaatctca aggagaaaga   3300
tattattgtc ttttacactt gcgatgtccc caacaatgtg aagacattag aaggccaaag   3360
caagaccttc ttgatgattg atgttcatca cttttcaggc aacggtttcg tggttcccga   3420
ggaagtaaac aagacggttc atgagatttc tgatgaagag atgaaaacag aaaccctctt   3480
tacctcgaag gtagaagaag aaaccaaatc agaggagaaa aaggagggt ttatgctgtt    3540 tggtgttagg atccaatagc tagctacttg gttcttaggt tttttatatt ataacttaat   3600
tagagtatgg ttttttatttg cttttgtatt acatagtttt tttatttaca aactcgatgc   3660
ttcgattttg atatctaaca ttaattagat aaattgtctc tcttgagtag atcaaaaaaa   3720
aaagaagaag aaaaaccaaa agaggcttta aattcttctt cttttaagag ttaagacaaa   3780
agccacttaa ctgctacaaa ctacaacgaa ctaaacaatc ctaacaaaga catttagtta   3840
atgtcacaaa atgaaatag                                                 3859
```

<210> SEQ ID NO 65
<211> LENGTH: 361
<212> TYPE: PRT
<213> ORGANISM: Arabidopsis thaliana

<400> SEQUENCE: 65

```
Met Glu Tyr Ser Cys Val Asp Asp Ser Ser Thr Thr Ser Glu Ser Leu
  1               5                  10                  15

Ser Ile Ser Thr Thr Pro Lys Pro Thr Thr Thr Glu Lys Lys Leu
             20                  25                  30

Ser Ser Pro Pro Ala Thr Ser Met Arg Leu Tyr Arg Met Gly Ser Gly
         35                  40                  45

Gly Ser Ser Val Val Leu Asp Ser Glu Asn Gly Val Glu Thr Glu Ser
     50                  55                  60

Arg Lys Leu Pro Ser Ser Lys Tyr Lys Gly Val Val Pro Gln Pro Asn
 65                  70                  75                  80

Gly Arg Trp Gly Ala Gln Ile Tyr Glu Lys His Gln Arg Val Trp Leu
                 85                  90                  95

Gly Thr Phe Asn Glu Glu Glu Glu Ala Ala Ser Ser Tyr Asp Ile Ala
            100                 105                 110

Val Arg Arg Phe Arg Gly Arg Asp Ala Val Thr Asn Phe Lys Ser Gln
        115                 120                 125

Val Asp Gly Asn Asp Ala Glu Ser Ala Phe Leu Asp Ala His Ser Lys
    130                 135                 140

Ala Glu Ile Val Asp Met Leu Arg Lys His Thr Tyr Ala Asp Glu Phe
145                 150                 155                 160

Glu Gln Ser Arg Arg Lys Phe Val Asn Gly Asp Lys Arg Ser Gly
                165                 170                 175

Leu Glu Thr Ala Thr Tyr Gly Asn Asp Ala Val Leu Arg Ala Arg Glu
            180                 185                 190

Val Leu Phe Glu Lys Thr Val Thr Pro Ser Asp Val Gly Lys Leu Asn
        195                 200                 205

Arg Leu Val Ile Pro Lys Gln His Ala Glu Lys His Phe Pro Leu Pro
    210                 215                 220

Ala Met Thr Thr Ala Met Gly Met Asn Pro Ser Pro Thr Lys Gly Val
225                 230                 235                 240
```

```
Leu Ile Asn Leu Glu Asp Arg Thr Gly Lys Val Trp Arg Phe Arg Tyr
                245                 250                 255

Ser Tyr Trp Asn Ser Ser Gln Ser Tyr Val Leu Thr Lys Gly Trp Ser
            260                 265                 270

Arg Phe Val Lys Glu Lys Asn Leu Arg Ala Gly Asp Val Val Cys Phe
        275                 280                 285

Glu Arg Ser Thr Gly Pro Asp Arg Gln Leu Tyr Ile His Trp Lys Val
    290                 295                 300

Arg Ser Ser Pro Val Gln Thr Val Val Arg Leu Phe Gly Val Asn Ile
305                 310                 315                 320

Phe Asn Val Ser Asn Glu Lys Pro Asn Asp Val Ala Val Glu Cys Val
                325                 330                 335

Gly Lys Lys Arg Ser Arg Glu Asp Leu Phe Ser Leu Gly Cys Ser
            340                 345                 350

Lys Lys Gln Ala Ile Ile Asn Ile Leu
            355                 360

<210> SEQ ID NO 66
<211> LENGTH: 352
<212> TYPE: PRT
<213> ORGANISM: Arabidopsis thaliana

<400> SEQUENCE: 66

Met Asp Ser Ser Cys Ile Asp Glu Ile Ser Ser Thr Ser Glu Ser
 1               5                  10                  15

Phe Ser Ala Thr Thr Ala Lys Lys Leu Ser Pro Pro Ala Ala Ala
            20                  25                  30

Leu Arg Leu Tyr Arg Met Gly Ser Gly Ser Ser Val Val Leu Asp
        35                  40                  45

Pro Glu Asn Gly Leu Glu Thr Glu Ser Arg Lys Leu Pro Ser Ser Lys
    50                  55                  60

Tyr Lys Gly Val Val Pro Gln Pro Asn Gly Arg Trp Gly Ala Gln Ile
65                  70                  75                  80

Tyr Glu Lys His Gln Arg Val Trp Leu Gly Thr Phe Asn Glu Gln Glu
                85                  90                  95

Glu Ala Ala Arg Ser Tyr Asp Ile Ala Ala Cys Arg Phe Arg Gly Arg
            100                 105                 110

Asp Ala Val Val Asn Phe Lys Asn Val Leu Glu Asp Gly Asp Leu Ala
        115                 120                 125

Phe Leu Glu Ala His Ser Lys Ala Glu Ile Val Asp Met Leu Arg Lys
    130                 135                 140

His Thr Tyr Ala Asp Glu Leu Glu Gln Asn Asn Lys Arg Gln Leu Phe
145                 150                 155                 160

Leu Ser Val Asp Ala Asn Gly Lys Arg Asn Gly Ser Ser Thr Thr Gln
                165                 170                 175

Asn Asp Lys Val Leu Lys Thr Arg Glu Val Leu Phe Glu Lys Ala Val
            180                 185                 190

Thr Pro Ser Asp Val Gly Lys Leu Asn Arg Leu Val Ile Pro Lys Gln
        195                 200                 205

His Ala Glu Lys His Phe Pro Leu Pro Ser Ser Pro Ala Val Thr
    210                 215                 220

Lys Gly Val Leu Ile Asn Phe Glu Asp Val Asn Gly Lys Val Trp Arg
225                 230                 235                 240

Phe Arg Tyr Ser Tyr Trp Asn Ser Ser Gln Ser Tyr Val Leu Thr Lys
```

```
                     245                 250                 255
Gly Trp Ser Arg Phe Val Lys Glu Lys Asn Leu Arg Ala Gly Asp Val
                260                 265                 270

Val Thr Phe Glu Arg Ser Thr Gly Leu Glu Arg Gln Leu Tyr Ile Asp
            275                 280                 285

Trp Lys Val Arg Ser Gly Pro Arg Glu Asn Pro Val Gln Val Val Val
        290                 295                 300

Arg Leu Phe Gly Val Asp Ile Phe Asn Val Thr Val Lys Pro Asn
305                 310                 315                 320

Asp Val Val Ala Val Cys Gly Lys Arg Ser Arg Asp Val Asp Asp
                325                 330                 335

Met Phe Ala Leu Arg Cys Ser Lys Lys Gln Ala Ile Ile Asn Ala Leu
                340                 345                 350

<210> SEQ ID NO 67
<211> LENGTH: 333
<212> TYPE: PRT
<213> ORGANISM: Arabidopsis thaliana

<400> SEQUENCE: 67

Met Asp Ala Met Ser Ser Val Asp Glu Ser Thr Thr Thr Asp Ser
1               5                   10                  15

Ile Pro Ala Arg Lys Ser Ser Pro Ala Ser Leu Leu Tyr Arg Met
            20                  25                  30

Gly Ser Gly Thr Ser Val Val Leu Asp Ser Glu Asn Gly Val Glu Val
        35                  40                  45

Glu Val Glu Ala Glu Ser Arg Lys Leu Pro Ser Ser Arg Phe Lys Gly
    50                  55                  60

Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Ala His Arg Phe Arg Gly Arg Asp Ala Val
            100                 105                 110

Thr Asn Phe Lys Asp Thr Thr Phe Glu Glu Glu Val Glu Phe Leu Asn
        115                 120                 125

Ala His Ser Lys Ser Glu Ile Val Asp Met Leu Arg Lys His Thr Tyr
    130                 135                 140

Lys Glu Glu Leu Asp Gln Arg Lys Arg Asn Arg Asp Gly Asn Gly Lys
145                 150                 155                 160

Glu Thr Thr Ala Phe Ala Leu Ala Ser Met Val Val Met Thr Gly Phe
                165                 170                 175

Lys Thr Ala Glu Leu Leu Phe Glu Lys Thr Val Thr Pro Ser Asp Val
            180                 185                 190

Gly Lys Leu Asn Arg Leu Val Ile Pro Lys His Gln Ala Glu Lys His
        195                 200                 205

Phe Pro Leu Pro Leu Gly Asn Asn Val Ser Val Lys Gly Met Leu
    210                 215                 220

Leu Asn Phe Glu Asp Val Asn Gly Lys Val Trp Arg Phe Arg Tyr Ser
225                 230                 235                 240

Tyr Trp Asn Ser Ser Gln Ser Tyr Val Leu Thr Lys Gly Trp Ser Arg
                245                 250                 255

Phe Val Lys Glu Lys Arg Leu Cys Ala Gly Asp Leu Ile Ser Phe Lys
            260                 265                 270
```

```
Arg Ser Asn Asp Gln Asp Gln Lys Phe Phe Ile Gly Trp Lys Ser Lys
        275                 280                 285

Ser Gly Leu Asp Leu Glu Thr Gly Arg Val Met Arg Leu Phe Gly Val
    290                 295                 300

Asp Ile Ser Leu Asn Ala Val Val Val Lys Glu Thr Thr Glu Val
305                 310                 315                 320

Leu Met Ser Ser Leu Arg Cys Lys Lys Gln Arg Val Leu
                325                 330

<210> SEQ ID NO 68
<211> LENGTH: 344
<212> TYPE: PRT
<213> ORGANISM: Arabidopsis thaliana

<400> SEQUENCE: 68

Met Glu Ser Ser Ser Val Asp Glu Ser Thr Thr Ser Thr Gly Ser Ile
1               5                   10                  15

Cys Glu Thr Pro Ala Ile Thr Pro Ala Lys Lys Ser Ser Val Gly Asn
                20                  25                  30

Leu Tyr Arg Met Gly Ser Gly Ser Ser Val Val Leu Asp Ser Glu Asn
            35                  40                  45

Gly Val Glu Ala Glu Ser Arg Lys Leu Pro Ser Ser Lys Tyr Lys Gly
    50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Val His Arg Phe Arg Arg Arg Asp Ala Val
            100                 105                 110

Thr Asn Phe Lys Asp Val Lys Met Asp Glu Asp Glu Val Asp Phe Leu
        115                 120                 125

Asn Ser His Ser Lys Ser Glu Ile Val Asp Met Leu Arg Lys His Thr
    130                 135                 140

Tyr Asn Glu Glu Leu Glu Gln Ser Lys Arg Arg Arg Asn Gly Asn Gly
145                 150                 155                 160

Asn Met Thr Arg Thr Leu Leu Thr Ser Gly Leu Ser Asn Asp Gly Val
                165                 170                 175

Ser Thr Thr Gly Phe Arg Ser Ala Glu Ala Leu Phe Glu Lys Ala Val
            180                 185                 190

Thr Pro Ser Asp Val Gly Lys Leu Asn Arg Leu Val Ile Pro Lys His
        195                 200                 205

His Ala Glu Lys His Phe Pro Leu Pro Ser Ser Asn Val Ser Val Lys
    210                 215                 220

Gly Val Leu Leu Asn Phe Glu Asp Val Asn Gly Lys Val Trp Arg Phe
225                 230                 235                 240

Arg Tyr Ser Tyr Trp Asn Ser Ser Gln Ser Tyr Val Leu Thr Lys Gly
                245                 250                 255

Trp Ser Arg Phe Val Lys Glu Lys Asn Leu Arg Ala Gly Asp Val Val
            260                 265                 270

Ser Phe Ser Arg Ser Asn Gly Gln Asp Gln Gln Leu Tyr Ile Gly Trp
        275                 280                 285

Lys Ser Arg Ser Gly Ser Asp Leu Asp Ala Gly Arg Val Leu Arg Leu
    290                 295                 300

Phe Gly Val Asn Ile Ser Pro Glu Ser Ser Arg Asn Asp Val Val Gly
305                 310                 315                 320
```

Asn Lys Arg Val Asn Asp Thr Glu Met Leu Ser Leu Val Cys Ser Lys
                325                 330                 335

Lys Gln Arg Ile Phe His Ala Ser
            340

<210> SEQ ID NO 69
<211> LENGTH: 364
<212> TYPE: PRT
<213> ORGANISM: Arabidopsis thaliana

<400> SEQUENCE: 69

Met Asn Asn Ile Asp Asp Ala Lys Thr Glu Thr Ser Val Ser Ser Gly
1               5                   10                  15

Ser Ser Asp Ser Phe Leu Pro Leu Lys Lys Arg Met Arg Leu Asp Asp
            20                  25                  30

Glu Pro Glu Asn Ala Leu Val Val Ser Ser Pro Lys Thr Val Val
        35                  40                  45

Ala Ser Gly Asn Val Lys Tyr Lys Gly Val Val Gln Gln Gln Asn Gly
    50                  55                  60

His Trp Gly Ala Gln Ile Tyr Ala Asp His Lys Arg Ile Trp Leu Gly
65                  70                  75                  80

Thr Phe Lys Ser Ala Asp Glu Ala Ala Thr Ala Tyr Asp Ser Ala Ser
                85                  90                  95

Ile Lys Leu Arg Ser Phe Asp Ala Asn Ser His Arg Asn Phe Pro Trp
            100                 105                 110

Ser Thr Ile Thr Leu Asn Glu Pro Asp Phe Gln Asn Cys Tyr Thr Thr
        115                 120                 125

Glu Thr Val Leu Asn Met Ile Arg Asp Gly Ser Tyr Gln His Lys Phe
    130                 135                 140

Arg Asp Phe Leu Arg Ile Arg Ser Gln Ile Val Ala Ser Ile Asn Ile
145                 150                 155                 160

Gly Gly Pro Lys Gln Ala Arg Gly Glu Val Asn Gln Glu Ser Asp Lys
                165                 170                 175

Cys Phe Ser Cys Thr Gln Leu Phe Gln Lys Glu Leu Thr Pro Ser Asp
            180                 185                 190

Val Gly Lys Leu Asn Arg Leu Val Ile Pro Lys Lys Tyr Ala Val Lys
        195                 200                 205

Tyr Met Pro Phe Ile Ser Ala Asp Gln Ser Glu Lys Glu Gly Glu
    210                 215                 220

Ile Val Gly Ser Val Glu Asp Val Glu Val Val Phe Tyr Asp Arg Ala
225                 230                 235                 240

Met Arg Gln Trp Lys Phe Arg Tyr Cys Tyr Trp Lys Ser Ser Gln Ser
                245                 250                 255

Phe Val Phe Thr Arg Gly Trp Asn Ser Phe Val Lys Glu Lys Asn Leu
            260                 265                 270

Lys Glu Lys Asp Val Ile Ala Phe Tyr Thr Cys Asp Val Pro Asn Asn
        275                 280                 285

Val Lys Thr Leu Glu Gly Gln Arg Lys Asn Phe Leu Met Ile Asp Val
    290                 295                 300

His Cys Phe Ser Asp Asn Gly Ser Val Val Ala Glu Val Ser Met
305                 310                 315                 320

Thr Val His Asp Ser Ser Val Gln Val Lys Thr Glu Asn Leu Val
                325                 330                 335

Ser Ser Met Leu Glu Asp Lys Glu Thr Lys Ser Glu Glu Asn Lys Gly

```
                    340                 345                 350
Gly Phe Met Leu Phe Gly Val Arg Ile Glu Cys Pro
                355                 360

<210> SEQ ID NO 70
<211> LENGTH: 354
<212> TYPE: PRT
<213> ORGANISM: Arabidopsis thaliana

<400> SEQUENCE: 70

Met Asp Met Asp Glu Met Ser Asn Val Ala Lys Thr Thr Glu Thr
 1               5                  10                  15

Ser Gly Leu Thr Asp Ser Val Leu Ser Leu Thr Lys Arg Met Lys Pro
                20                  25                  30

Thr Glu Val Thr Thr Thr Lys Pro Ala Leu Ser Asn Thr Thr Lys
                35                  40                  45

Phe Lys Gly Val Val Gln Gln Gln Asn Gly His Trp Gly Ala Gln Ile
     50                  55                  60

Tyr Ala Asp His Arg Arg Ile Trp Leu Gly Thr Phe Lys Ser Ala His
65                  70                  75                  80

Glu Ala Ala Ala Ala Tyr Asp Ser Ala Ser Ile Lys Leu Arg Ser Phe
                85                  90                  95

Asp Ala Asn Ser His Arg Asn Phe Pro Trp Ser Asp Phe Thr Leu His
                100                 105                 110

Glu Pro Asp Phe Gln Glu Cys Tyr Thr Thr Glu Ala Val Leu Asn Met
                115                 120                 125

Ile Arg Asp Gly Ser Tyr Gln His Lys Phe Arg Asp Phe Leu Arg Ile
     130                 135                 140

Arg Ser Gln Ile Val Ala Asn Ile Asn Ile Val Gly Ser Lys Gln Val
145                 150                 155                 160

Leu Gly Gly Gly Glu Gly Gly Gln Glu Ser Asn Lys Cys Phe Ser Cys
                165                 170                 175

Thr Gln Leu Phe Gln Lys Glu Leu Thr Pro Ser Asp Val Gly Lys Leu
                180                 185                 190

Asn Arg Leu Val Ile Pro Lys Lys Tyr Ala Val Lys Tyr Met Pro Phe
                195                 200                 205

Ile Ser Asp Asp Gln Ser Glu Lys Glu Thr Ser Glu Gly Val Glu Asp
     210                 215                 220

Val Glu Val Val Phe Tyr Asp Arg Ala Met Arg Gln Trp Lys Phe Arg
225                 230                 235                 240

Tyr Cys Tyr Trp Arg Ser Ser Gln Ser Phe Val Phe Thr Arg Gly Trp
                245                 250                 255

Asn Gly Phe Val Lys Glu Lys Asn Leu Lys Glu Lys Asp Ile Ile Val
                260                 265                 270

Phe Tyr Thr Cys Asp Val Pro Asn Asn Val Lys Thr Leu Glu Gly Gln
                275                 280                 285

Ser Lys Thr Phe Leu Met Ile Asp Val His His Phe Ser Gly Asn Gly
                290                 295                 300

Phe Val Val Pro Glu Glu Val Asn Lys Thr Val His Glu Ile Ser Asp
305                 310                 315                 320

Glu Glu Met Lys Thr Glu Thr Leu Phe Thr Ser Lys Val Glu Glu Glu
                325                 330                 335

Thr Lys Ser Glu Glu Lys Lys Gly Gly Phe Met Leu Phe Gly Val Arg
                340                 345                 350
```

Ile Gln

<210> SEQ ID NO 71
<211> LENGTH: 14
<212> TYPE: DNA
<213> ORGANISM: Artificial Sequence
<220> FEATURE:
<223> OTHER INFORMATION: EBS Consensus Sequence

<400> SEQUENCE: 71 agggggatg aact                                                            14